United States Patent
Shen et al.

(10) Patent No.: US 11,419,887 B2
(45) Date of Patent: Aug. 23, 2022

(54) VEHICLE FOR DELIVERING A COMPOUND TO A MUCOUS MEMBRANE AND RELATED COMPOSITIONS, METHODS AND SYSTEMS

(71) Applicant: California Institute of Technology, Pasadena, CA (US)

(72) Inventors: Yue Shen, Pasadena, CA (US); Sarkis K. Mazmanian, Porter Ranch, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 16/386,522

(22) Filed: Apr. 17, 2019

(65) Prior Publication Data

US 2019/0314400 A1  Oct. 17, 2019

Related U.S. Application Data

(63) Continuation of application No. 14/803,598, filed on Jul. 20, 2015, now abandoned, which is a continuation of application No. 13/082,183, filed on Apr. 7, 2011, now abandoned.

(Continued)

(51) Int. Cl.
*A61K 31/715* (2006.01)
*G01N 33/50* (2006.01)
(Continued)

(52) U.S. Cl.
CPC ............ *A61K 31/715* (2013.01); *A23L 33/10* (2016.08); *A61K 9/10* (2013.01); *A61K 39/0216* (2013.01);
(Continued)

(58) Field of Classification Search
CPC .............. A61K 31/715; A61K 47/6901; A61K 39/0216; A61K 9/10; A61K 9/0065;
(Continued)

(56) References Cited

U.S. PATENT DOCUMENTS 4,775,626 A  10/1988  Armenta et al.
5,571,900 A  11/1996  Wiegand et al.
(Continued)

FOREIGN PATENT DOCUMENTS

CA  2800174  11/2011
CN  1818061 A  8/2006
(Continued)

OTHER PUBLICATIONS

Chen et al., "Delivery of foreign antigens by engineered outer membrane vesicle vaccines", Proc Natl Acad Sci USA, Feb. 16, 2010, pp. 3099-3104, 107 (7), National Academy of Sciences, Washington, D.C.

(Continued)

*Primary Examiner* — Gollamudi S Kishore
(74) *Attorney, Agent, or Firm* — Sheppard, Mullin, Richter & Hampton LLP

(57) ABSTRACT

PSA is delivered to the host by outer membrane vesicles (OMVs), secretion structures that target bacterial molecules to host cells. Purified OMVs direct the in vitro differentiation of functional Tregs with potent suppressive activity in a PSA dependent manner. Treatment of animals with OMVs containing PSA prevents experimental colitis and suppresses pro-inflammatory cytokine responses in the gut, and indicate that compositions, medicaments, and methods useful for the treatment of inflammation, and more particularly, inflammatory bowel diseases.

12 Claims, 25 Drawing Sheets

Specification includes a Sequence Listing.

Related U.S. Application Data

(60) Provisional application No. 61/345,039, filed on May 14, 2010, provisional application No. 61/321,527, filed on Apr. 7, 2010.

(51) Int. Cl.
| | |
|---|---|
| *C08B 37/00* | (2006.01) |
| *A61K 39/02* | (2006.01) |
| *A23L 33/10* | (2016.01) |
| *A61K 47/69* | (2017.01) |
| *A61K 9/10* | (2006.01) |
| *C12N 5/0783* | (2010.01) |
| *A61K 39/00* | (2006.01) |
| *A61K 9/00* | (2006.01) |

(52) U.S. Cl.
CPC ........ *A61K 47/6901* (2017.08); *C08B 37/006* (2013.01); *C12N 5/0637* (2013.01); *G01N 33/505* (2013.01); *A61K 9/0065* (2013.01); *A61K 2039/542* (2013.01); *A61K 2039/55555* (2013.01); *A61K 2039/55583* (2013.01); *A61K 2039/57* (2013.01); *A61K 2039/58* (2013.01); *G01N 2333/5428* (2013.01)

(58) Field of Classification Search
CPC .......... A61K 2039/542; A61K 2039/58; A61K 2039/57; A61K 2039/55583; A61K 2039/55555; A23L 33/10; C08B 37/006; C12N 5/0637; G01N 33/505; G01N 2333/5428; A61P 43/00; A61P 37/06; A61P 37/02; A61P 35/00; A61P 29/00; A61P 1/04; A61P 1/00
See application file for complete search history.

(56) References Cited

U.S. PATENT DOCUMENTS

| | | | |
|---|---|---|---|
| 5,679,654 A | 10/1997 | Tzianabos et al. |
| 5,700,787 A | 12/1997 | Tzianabos et al. |
| 6,358,939 B1 | 3/2002 | Hayes et al. |
| 7,026,283 B2 | 4/2006 | Fleming et al. |
| 7,026,285 B2 | 4/2006 | Tzianabos et al. |
| 7,083,777 B1 | 8/2006 | Tzianabos et al. |
| 7,384,645 B2 | 6/2008 | Foster et al. |
| 7,629,330 B2 | 12/2009 | Wang et al. |
| 8,206,726 B2 | 6/2012 | Kasper et al. |
| 9,057,070 B2 | 6/2015 | Mazmanian et al. |
| 9,265,790 B2 | 2/2016 | Tzianabos et al. |
| 9,452,189 B2 | 9/2016 | Mazmanian et al. |
| 9,539,281 B2 | 1/2017 | Kasper et al. |
| 2002/0146396 A1 | 10/2002 | Albert et al. |
| 2003/0044425 A1 | 3/2003 | Burt et al. |
| 2003/0059462 A1 | 3/2003 | Barenholz et al. |
| 2003/0147865 A1 | 8/2003 | Salomon et al. |
| 2003/0147922 A1 | 8/2003 | Capiau et al. |
| 2003/0219413 A1 | 11/2003 | Comstock et al. |
| 2004/0063685 A1 | 4/2004 | Ilzawa et al. |
| 2004/0092433 A1 | 5/2004 | Wang et al. |
| 2004/0219160 A1 | 11/2004 | Tzianabos et al. |
| 2005/0013831 A1 | 1/2005 | Foster et al. |
| 2005/0020515 A1 | 1/2005 | Graff et al. |
| 2005/0048587 A1 | 3/2005 | Rao et al. |
| 2005/0063979 A1 | 3/2005 | Pickl et al. |
| 2005/0119164 A1 | 6/2005 | Taylor et al. |
| 2005/0147624 A1 | 7/2005 | Jennings et al. |
| 2005/0181021 A1 | 8/2005 | Jennings et al. |
| 2006/0029662 A1 | 2/2006 | Calias et al. |
| 2006/0110412 A1 | 5/2006 | Desmons et al. |
| 2006/0127387 A1 | 6/2006 | Zikria et al. |
| 2006/0257852 A1 | 11/2006 | Rappuoli et al. |
| 2006/0275752 A1 | 12/2006 | Sindhi |
| 2006/0276378 A1 | 12/2006 | Wilson |
| 2007/0041986 A1 | 2/2007 | Blaszczak et al. |
| 2007/0154991 A1 | 7/2007 | Comstock et al. |
| 2007/0207526 A1 | 9/2007 | Coit et al. |
| 2008/0057565 A1 | 3/2008 | Comstock et al. |
| 2008/0311140 A1 | 12/2008 | Lee et al. |
| 2009/0017472 A1 | 1/2009 | Stuhlmuller et al. |
| 2009/0124573 A1 | 5/2009 | Mazmanian et al. |
| 2009/0252708 A1 | 10/2009 | Fitzpatrick et al. |
| 2009/0317410 A1 | 12/2009 | Wang et al. |
| 2009/0317427 A1 | 12/2009 | Kasper et al. |
| 2010/0080760 A1 | 4/2010 | Hyde et al. |
| 2010/0221315 A1 | 9/2010 | Constantino et al. |
| 2010/0221755 A1 | 9/2010 | Lee et al. |
| 2010/0275282 A1 | 10/2010 | Round et al. |
| 2010/0311686 A1 | 12/2010 | Kasper et al. |
| 2010/0330166 A1 | 12/2010 | Ishida et al. |
| 2011/0002965 A1 | 1/2011 | Round |
| 2011/0251156 A1 | 10/2011 | Shen et al. |
| 2011/0287048 A1 | 11/2011 | Round et al. |
| 2012/0087895 A1 | 4/2012 | Mazmanian et al. |
| 2013/0039949 A1 | 2/2013 | Mazmanian |
| 2013/0064859 A1 | 3/2013 | Mazmanian et al. |
| 2013/0121966 A1 | 5/2013 | Mazmanian et al. |
| 2013/0195802 A1 | 8/2013 | Moore |
| 2014/0072534 A1 | 3/2014 | Mazmanian et al. |
| 2014/0335131 A1 | 11/2014 | Mazmanian et al. |
| 2016/0022727 A1 | 1/2016 | Round et al. |
| 2016/0030464 A1 | 2/2016 | Mazmanian et al. |
| 2016/0143940 A1 | 5/2016 | Shen et al. |
| 2016/0151408 A1 | 6/2016 | Mazmanian et al. |
| 2016/0361343 A1 | 12/2016 | Mazmanian et al. |
| 2017/0003274 A1 | 1/2017 | Round et al. |
| 2018/0264026 A1 | 9/2018 | Round et al. |
| 2019/0022128 A1 | 1/2019 | Mazmanian et al. |
| 2020/0197436 A1 | 6/2020 | Round et al. |

FOREIGN PATENT DOCUMENTS

| | | |
|---|---|---|
| DE | 3704389 | 8/1988 |
| EP | 371414 | 6/1990 |
| EP | 382576 | 8/1991 |
| EP | 497524 | 8/1992 |
| EP | 1358885 | 11/2003 |
| EP | 1459757 A1 | 9/2004 |
| EP | 2217250 | 8/2010 |
| EP | 2422200 | 8/2010 |
| EP | 2555753 | 10/2011 |
| EP | 2571982 | 11/2011 |
| EP | 2764090 | 8/2014 |
| EP | 2994161 | 3/2016 |
| GB | 2286193 | 8/1995 |
| HK | 1201291 | 8/2015 |
| JP | S56128721 | 10/1981 |
| JP | H10507746 | 7/1998 |
| JP | 2002540074 | 11/2002 |
| JP | 2002541113 | 12/2002 |
| JP | 2003204796 | 7/2003 |
| JP | 2004536028 | 12/2004 |
| JP | 2006-522135 A | 9/2006 |
| JP | 2010059201 | 3/2010 |
| JP | 2012-524910 A | 10/2012 |
| JP | 2016521284 | 7/2016 |
| JP | 6027961 | 11/2016 |
| JP | 6296367 | 3/2018 |
| JP | 6471888 | 2/2019 |
| JP | 6944965 | 10/2021 |
| WO | WO199531990 | 11/1995 |
| WO | WO199607427 | 3/1996 |
| WO | WO199632119 | 10/1996 |
| WO | WO199635433 | 11/1996 |
| WO | WO199842718 | 10/1998 |
| WO | WO199845335 | 10/1998 |
| WO | WO200001733 | 1/2000 |
| WO | WO2000059515 | 10/2000 |
| WO | WO200207741 | 1/2002 |
| WO | WO2002045708 | 6/2002 |
| WO | WO2003075953 | 9/2003 |
| WO | WO2003077863 | 9/2003 |
| WO | WO2003095606 | 11/2003 |

(56) References Cited

FOREIGN PATENT DOCUMENTS

| | | |
|---|---|---|
| WO | WO2004050909 | 6/2004 |
| WO | WO2004089407 | 10/2004 |
| WO | WO2005010215 | 2/2005 |
| WO | WO2005094571 | 10/2005 |
| WO | WO2007040446 | 4/2007 |
| WO | 2007092451 A2 | 8/2007 |
| WO | WO2008095141 | 8/2008 |
| WO | WO2009062132 | 5/2009 |
| WO | WO2009149149 | 12/2009 |
| WO | WO2010124256 | 10/2010 |
| WO | WO2011056703 | 5/2011 |
| WO | WO2011127302 | 10/2011 |
| WO | WO2011146910 | 11/2011 |
| WO | WO2011153226 | 12/2011 |
| WO | WO2012027032 | 3/2012 |
| WO | WO2012103532 | 8/2012 |
| WO | WO2013009945 | 1/2013 |
| WO | WO2013019896 | 2/2013 |
| WO | WO2013036290 | 3/2013 |
| WO | WO2013052099 | 4/2013 |
| WO | WO2014182966 | 11/2014 |

OTHER PUBLICATIONS

Braun et al., "Body traffic: ecology, genetics, and immunity in inflammatory bowel disease", Annu Rev Pathol., Feb. 28, 2007, pp. 401-429, vol. 2, Annual Reviews, Palo Alto, CA.

Coyne et al., "Polysaccharide biosynthesis locus required for virulence of Bacteroides fragilis". Infect. Immun., Jul. 2001, pp. 4342-4350, vol. 69, No. 7, American Society for Microbiology, Washington DC.

Horstman et al., "Enterotoxigenic *Escherichia coli* secretesactive heat-labile enterotoxin via outer membrane vesicles", J Bioi Chem., Apr. 28, 2000, pp. 12489-12496, 275, American Society for Biochemistry and Molecular Biology, Rockville, MD.

Kesty et al., "Incorporation of heterologous outer membraneand periplasmic proteins into *Escherichia coli* outer membrane vesicles", J Bioi Chem., Jan. 16, 2004, pp. 2069-2076, 279, American Society for Biochemistry and Molecular Biology, Rockville, MD.

Mazmanian et al., "A microbial symbiosis factor preventsintestinal inflammatory disease", Nature, May 29, 2008, pp. 620-625, 453, Macmillan Publishers Limited, Basingstoke, United Kingdom.

Mazmanian et al., "An Immunomodulatory Molecule of Symbiotic Bacteria Directs Maturation of the Host Immune System", Cell, Jul. 15, 2005, pp. 107-118, vol. 122, Issue 1, Elsevier, Amsterdam, Netherlands.

McKenna et al., "A comparison of the haemagglutinating and enzymic activities of Bacteroides fragilis whole cells and outer membrane vesicles", Microb Pathog., Apr. 1996, pp. 191-202, 20(4), Elsevier, Amsterdam, Netherlands.

Patrick et al., "A comparison of the haemagglutinating and enzymic activities ofBacteroides fragiliswhole cells and outer membrane vesicles", Apr. 1996, pp. 191-202, vol. 20, Issue 4, Elsevier, Amsterdam, Netherlands.

Patrick et al., "Separation of capsulate and non-capsulate Bacteroides fragilis on a discontinuous density gradient", J Med Microbial., 1983, pp. 239-241, 16(2), The Pathological Society of Great Britain and Ireland, London, United Kingdom.

PCT Application No. PCT/US2011/031606 Search Report and Written Opinion dated Dec. 15, 2011.

Round et al., Office Action in U.S. Appl. No. 13/112,725, filed May 30, 2013.

Round et al., "Inducible Foxp3+ regulatory T cell development by a commensal bacterium of the intestinal microbiota", PNAS, Jul. 6, 2010, pp. 12204-12209, vol. 107 No. 27, PNAS,Washington, DC.

Round et al., "The gut microbiota shapes intestinal immune responses during health and disease", Nat Rev Immunol., May 1, 2009, pp. 313-323, 9, Macmillan Publishers Limited, Basingstoke, United Kingdom.

Scheiffele et al., "Induction of TNBS colitis in mice", Current Protocols in Immunology, Aug. 1, 2002, Chapter 15, Unit 15.19, Wiley, Hoboken, NJ.

Stingele et al. "Zwitterionic polysaccharides stimulate T cells with no preferential Vbeta usage and promote anergy, resulting in protection against experimental abscess formation", The Journal of immunology, Feb. 1, 2004, pp. 1483-1490, vol. 172, Issue 3, he American Association of Immunologists, Inc., Rockville, MD.

Xavier et al. "Unravelling the pathogenesis of inflammatory bowel disease", Nature, Jul. 26, 2007, pp. 427-434, 448, Macmillan Publishers Limited, Basingstoke, United Kingdom.

Amidon et al., "Proposed New USP General Information Chapter, Excipient Performance <1059>", Pharmacopeial Forum, Nov.-Dec. 2007, pp. 1311-1323, vol. 33(6), The United States Pharmacopeia! Convention, Rockville, MD.

Davila et al., "Efficacy and Toxicity Management of 19-28z CAR T Cell Therapy in B Cell Acute Lymphoblastic Leukemia," Sci Transl Med 2014, 6(224), in 23 pages.

Final Office Action dated Feb. 9, 2021 in U.S. Appl. No. 16/562,358.

Final Office Action dated Jan. 25, 2021 in U.S. Appl. No. 16/151,793.

Head & Jurenka, "Inflammatory Bowel Disease Part I: Ulcerative Colitis—Pathophysiology and Conventional and Alternative Treatment Options," Alternative Medicine Review 2003, 8(3), 247-283.

Notification of Reasons for Refusal for Japanese Patent Application No. 2019-061261 dated Jan. 26, 2021, in 7 pages.

"Asthma" from the Centers for Disease Control and Prevention, [retrieved Nov. 13, 2012]. Retrieved from the Internet www.cdc.gov/asth ma/aag/2010/overview.html.

"Ulcerative Colitis" from the National Institutes of Health [online], [retrieved Nov. 9, 2012]. Retrieved from the Internet www.digestive.niddk.nih.gov/ddiseases/pubs/colitis/UlcerativeColitis508.pdf.

[No Author Listed] "MS the Disease". National Multiple Sclerosis Society. Downloaded from the internet at http://www.nationalmssociety.org/About-the-Society/Press-Room/MS-the-Disease on Dec. 19, 2016, 4 pages (website copyright 2014).

[No Author Listed] Drug Absorption, Bioavailability, and Routes of Administration. Goodman & Oilman's The Pharmacological Basis of Therapeutics, Tenth Edition, McGraw-Hill Medical Publishing Edition, New York, 2001, pp. 5-8.

[No Author Listed] Progress in Autoimmune Diseases Research. National Institutes of Health. The Autoimmune Diseases Coordinating Committee. Report to Congress. U.S. Department of Health and Human Service. Mar. 2005. 146 pages.

Abreu, M.T. et al. "Measurement of vitamin D levels in inflammatory bowel disease patients reveals a subset of Crohn's disease patients with elevated 1,25-dihydroxyvitamin D and low bone mineral density" Gut, 2004, 53(8) pp. 1129-1136.

"Abscess" from Wikipedia, dated May 9, 2015 (6 pages) https://en.wikipedia.org/Wiki/Abscess.

Adams JS, et al. (2008) Unexpected actions of vitamin D: new perspectives on the regulation of innate and adaptive immunity. Nat Clin Pract Endocrinol Metab 4:80-90.

Adams JS, et al. (2012) Extrarenal expression of the 25-hydroxyvitamin D-1-hydroxylase. Archives of biochemistry and biophysics 523: 95-102.

Adkins et al., "Exclusive Th2 Primary Effector Function in Spleens but Mixed Th1/Th2Function in Lymph Nodes of Murine Neonates" Journal Immunol, Mar. 1, 2000, pp. 2347-2353, 164(5).

Adkins et al.,"Early Block in Maturation Is Associated with Thymic Involution in Mammary Tumor-Bearing Mice", J Immunology, Jun. 1, 2000, pp. 5635-5640, vol. 164, Issue 11.

Adkins, "T-cell function in newborn mice and humans", Review Immunology Today, Jul. 1, 1999, pp. 330-335, vol. 20, Issue 7.

Adkins, "Development of neonatal Th1/Th2 function", Int Rev Immunol, 2000; pp. 157-171, 19 (2-3), Taylor and Francis Group, Abingdon, United Kingdom.

Advisory Action for U.S. Appl. No. 13/112,725, filed May 20, 2011 on behalf of June L. Round, dated Mar. 4, 2014. 3 pages.

Afzali, "The role of T helper 17 (Th17) and regulatory T cells (Treg) in human organ transplantation and autoimmune disease", Clinical and Experimental Immunology, Apr. 2007, pp. 32-46, vol. 148, Issue 1.

(56) References Cited

OTHER PUBLICATIONS

Aharoni et al., Bystander suppression of experimental autoimmune encephalomyelitis by T cell lines and clones of the type induced by copolymer 1. J Neuroimmunol. Nov. 1998 2;91(1-2):135-46.
Aharoni et al., Copolymer 1 induces T cells of the T helper type 2 that crossreact with myelin basic protein and suppress experimental autoimmune encephalomyelitis. Proc Natl Acad Sci USA. Sep. 1997 30;94(20):10821-6.
Akbari et al., Antigen-specific regulatory T cells develop via the ICOS-ICOS-ligand pathway and inhibit allergen-induced airway hyperreactivity. Nat Med. Sep. 2002;8(9):1024-32. Epub Jul. 29, 2002.
Al-Bader et al. "Activation of Human Dendritic Cells Is Modulated by Components of the Outer Membranes of Neisseria meningitidis" Infection and Immunity. Oct. 2003; 71(10): 5590-5597).
Allen AC, et al. (2012) "A pilot study of the immunological effects of high-dose vitamin Din healthy volunteers". Multiple Sclerosis Journal; 2012; vol. 18; No. 12; pp. 1797-1800.
Amsen et al., "Instruction of distinct CD4 T helper cell fates by different notch ligands on antigen-presenting cells", Cell, May 14, 2004, pp. 515-526, vol. 117, Issue 4.
Anderson AC, et al. (2012) A transgenic model of central nervous system autoimmunity mediated by CD4+ and CD8+ T and B cells. Journal of immunology 188: 2084-2092.
Arnon et al., New insights into the mechanism of action of copolymer 1 in experimental allergic encephalomyelitis and multiple sclerosis. J Neural. Apr. 1996;243(4 Suppl I):S8-13. Review.
Asadullah et al., Interleukin-10 therapy-review of a new approach. Pharmacol Rev. Jun. 2003;55(2):241-69.
Ascherio A, et al. "Vitamin D and multiple sclerosis". Lancet Neurology; Jun. 2010; vol. 9: pp. 599-612.
Asseman et al., "An essential role for interleukin 10 in the function of regulatory T cells that inhibit intestinal inflammation", J Exp Med., Oct. 4, 1999, pp. 995-1004, 190 (7).
Atarashi et al., "ATP drives lamina propria TH17 cell differentiation", Nature, Oct. 9, 2008, pp. 808-812, vol. 455, Issue 7214.
Awasthi, "Interplay between effector Th17 and regulatory T cells", J Clin Immunol, Nov. 2008, pp. 660-670, 28(6), Springer International Publishing AG, Cham, Switzerland.
Azzawi et al., Identification of activated T lymphocytes and eosinophils in bronchial biopsies instable a topic asthma. Am Rev Respir Dis. Dec. 1990; 142(6 Pt 1):1407-13.
Bach, The effect of infections on susceptibility to autoimmune and allergic diseases, N Engl J Med., Sep. 19, 2002, pp. 911-920, vol. 347, No. 12.
Baecher-Allan CM, et al. (2011) CD2 costimulation reveals detective activity by human CD4+CD25(hi) regulatory cells in patients with multiple sclerosis. Journal of immunology 186: 3317-3326.
Banerjee et al. "Expansion of FOXP3 high regulatory T cells by human dendritic cells (DCs) in vitro and after injection of cytokine-matured DCs in myeloma patients" Blood. 2006; 108: 2655-2661.
Baranzini SE, et al. (2010) Genome, epigenome and RNA sequences of monozygotic twins discordant for multiple sclerosis. Nature 464: 1351-1356.
Barnes, M.J., et al. (2009). "Regulatory T cells reinforce intestinal homeostasis". Immunity 31, 401-411.
Bar-On L, et al. (2010) Defining in vivo dendritic cell functions using CD11c-DTR transgenic mice. Methods in molecular biology 595: 429-442.
Barrat FJ, et al. (2002) In vitro generation of interleukin 10-producing regulatory CD4(+) T cells is induced by immunosuppressive drugs and inhibited by T helper type 1 (Th1)- and Th2-inducing cytokines. J Exp Med 195: 603-616.
Barutca et al., Prevention of interleukin-2-induced severe bronchospasm with salbutamol. J Aerosol Med. 2003 Summer;16(2):183-4.
Basu et al., Synthesis and characterization of a peptide nucleic acid conjugated to a D-peptide analog of insulin-like growth factor 1 for increased cellular uptake. Bioconjug Chem. Jul.-Aug. 1997;8(4):481-8.

Batta et al., Conformational stabilization of the altruronic acid residue in the O-specific polysaccharide of Shigella sonnei/Plesiomonas shigelloides. Carbohydr Res. Dec. 1998;305(1):93-9.
Bayley DP et al. Analysis of cepA and other Bacteroides fragilis genes reveals a unique promoter structure. (2000) FEMS Microbial Lett 193:149-54.
Bazan et al., Unraveling the structure of IL-2. Science. Jul. 17, 1992;257(5068):410-3.
Becker et al., "TGF-Suppresses Tumor Progression in Colon Cancer by Inhibition of IL-6 transSignaling," Immunity, vol. 21, 491-501 (2004).
Becker KG, et al. (1998) Clustering of non-major histocompatibility complex susceptibility candidate loci in human autoimmune diseases. Proc Natl Acad Sci U S A 95: 9979-9984.
Belkaid et al., "Regulatory T cells in the control of host-microorganism interactions", Annu. Rev. Immunol., 2009. pp. 551-589, vol. 27.
Bell, "Function of CD4 T cell subsets in vivo: expression of CD45R isoforms", Semin Immune, Feb. 1, 1992, pp. 43-50, 14(1).
Berer et al., Commensal gut flora and brain autoimmunity: a love or hate affair? Acta Neuropathol. May 2012;123(5):639-51. doi: 10.1007/S00401-012-0949-9. Epub Feb. 10, 2012.
Berer et al., Commensal microbiota and myelin autoantigen cooperate to trigger autoimmune demyelination. Nature. Oct. 2, 20116;479(7374):538-41. doi: 10.1038/nature10554.
Berggren et al., Decreasing serum concentrations of all-trans, 13-cis retinoic acids and retinal during fasting and caloric restriction. J Intern Med. Mar. 2003;253(3):375-80.
Bernatowska-Matuszkiewicz et al., IgG subclasses and antibody response to pneumococcal capsular polysaccharides in children with severe sinopulmonary infections and asthma. Immunol Investi. 1991;20(2):173-185.
Bettelli E, et al. (2003) Myelin oligodendrocyte glycoprotein-specific T cell receptor transgenic mice develop spontaneous autoimmune optic neuritis. The Journal of experimental medicine 197: 1073-1081.
Bettelli, E. et al. "Reciprocal developmental pathways for the generation of pathogenic effector TH17 and regulatory T cells" Nature vol. 441 pp. 235-238 (2006).
Bhaduri et al., Simple and rapid method for disruption of bacteria for protein studies. Appl Environ Microbial. Oct. 1983;46(4):941-3.
Bhat R, et al. (2009) Innate and adaptive autoimmunity directed to the central nervous system. Neuron 64: 123-132.
Bilo et al., "Diagnosis of Hymenoptera venom allergy", Allergy, Nov. 2005, pp. 1339-1349, vol. 60, Issue 11.
Blander et al., Toll-dependent selection of microbial antigens for presentation by dendritic cells. Nature. Apr. 6, 2006;440(7085):808-12. Epub Feb. 19, 2006.
Blomfield et al. Lrp stimulates phase variation of type 1 fimbriation in E. coli K12. J. Bacteriology 175, 27-36, 1993.
Blumberg & Powrie, "Microbiota, Disease, and Back to Health: A Metastable Journey," Sci. Transl. Med., vol. 4, 137rv7 (2012).
Boguniewicz, "The autoimmune nature of chronic urticarial", Allergy and Asthma Proceedings, Sep.-Oct. 2008, pp. 433-438, vol. 29, No. 5.
Bollrath et al., "gp130-Mediated Stat3 Activation in Enterocytes Regulates Cell Survival and Cell-Cycle Progression during Colitis-Associated Tumorigenesis," Cancer Cell, vol. 15, 91-102 (2009).
Borsellino et al., Expression of ectonucleotidase CD39 by Foxp3+ Treg cells: hydrolysis of extracellular ATP and immune suppression. Blood. Aug. 15, 2007;110(4):1225-32. Epub Apr. 20, 2007.
Bouma et al., "The immunological and genetic basis of inflammatory bowel disease", Nat. Rev. Immunol., 2003, pp. 521-533, 3.
Bouskra, D., et al. (2008). Lymphoid tissue genesis induced by commensals through NOD1 regulates intestinal homeostasis. Nature 456, 507-510.
Braat et al., "A Phase I Trial With Transgenic Bacteria Expressing interleukin-10 in Crohn's Disease" Clinical Gastroenterology and Hepatology, Jun. 2006, pp. 754-759, vol. 4, Issue 6.
Bregenholt, "S. Cells and cytokines in the pathogenesis of inflammatory bowel disease: newinsights from mouse T Cell transfer models", Exp Clin Immunogenet, Jun. 2000, pp. 115-129, vol. 17, No. 3, S. Karger AG, Basel, Switzerland.

(56) References Cited

OTHER PUBLICATIONS

Brichford, Can You Prevent Multiple Sclerosis? Understanding factors that increase your risk of multiple sclerosis and what—if anything—you can do about them. EverydayHealth.com. Dec. 2008; 2 pages.
Brubaker et al., Mitogenic activity of purified capsular polysaccharide A from Bacteroides fragilis: differential stimulatory effect on mouse and rat lymphocytes in vitro. J Immunol. Feb. 15, 1999; 162(4):2235-42.
Bruce D, et al. (2011) Converging pathways lead to overproduction of IL-17 in the absence of vitamin D signaling. International immunology 23: 519-528.
Brunkow, M.E., et al., "Disruption of a new forkhead/winged-helix protein, scurfin, results in the fatal lymphoproliferative disorder of the scurfy mouse" Nat Genet 27, 68-73 (2001).
Budinger et al., Immunologic mechanisms in hypersensitivity reactions to metal ions: an overview. Allergy. Feb. 2000;55(2):108-15. Review.
Burgers et al., The challenges of HIV vaccine development and testing. Best Pract Res Clin Obstet Gynaecol. Apr. 2005;19(2):277-91.
Byers et al., "Mechanism of action of vitamin D and the vitamin D receptor in colorectal cancer prevention and treatment," Rev. Endocr. Metab. Disord, Mar. 2012, pp. 31-38, vol. 13, Issue 1, Springer, Berlin, Germany.
Cabrera R, et al. (2010) Influence of serum and soluble CD25 (sCD25) on regulatory and effector T-cell function in hepatocellular carcinoma. Scandinavian journal of immunology 72: 293-301.
Cahill et al., "Inflammatory bowel disease: an immunity-mediated condition triggered by bacterial infection with Helicobacter hepaticus", Infect Immun., Aug. 1997, pp. 3126-3131, vol. 65 No. 8.
Campbell et al. The vitamin D receptor as a therapeutic target in Expert Opinion Ther. Targets, 2006; vol. 10; pp. 735-748.
Cantorna et al. "Vitamin D status, 1,25-dihydroxyvitamin D3, and the immune system" (Am. J. Clin. Nutr. 80(suppl):1717S-20S, 2004).
Cantorna MT, et al. (1996) "1,25-Dihydroxyvitamin D3 reversibly blocks the progression of relapsing encephalomyelitis, a model of multiple sclerosis". Proceedings of the National Academy of Sciences of the United States of America 93: 7861-7864.
Catorna, M.T. et al. 1,25-Dihydroxycholecalciferol prevents and ameliorates symptoms of experimental murine inflammatory bowel disease. J. Nutr. 2000 130(11) oo.2648-52.
Cash, H.L., et al. (2006). Symbiotic bacteria direct expression of an intestinal bactericidal lectin. Science 313, 1126-1130.
Chambers E. et al. (2011) The impact of vitamin D on regulatory! cells. Curr. Allergy Asthma Rep 11: 29-36.
Chang JH, et al. (2010) "1,25-Dihydroxyvitamin D3 inhibits the differentiation and migration of T(H)17 cells to protect against experimental autoimmune encephalomyelitis." PLoS One 5: e12925. 12 pages.
Chatila et al., Role of regulatory Tcells in human diseases. J Allergy Clin Immunol. Nov. 2005;116(5):949-59; quiz 960.
Chen et al. "Pertussis loxin by Inducing IL-6 Promotes the Generation of IL-17-Producing CD4 Cells". Journal of Immunology, May 15, 2007, pp. 6123-6129, vol. 178, No. 10.
Chen J et al., DNA inversion on conjugative plasmid pVT745. J Bacteriol. Nov. 2002; 184(21):5926-34.
Cho et al., "Recent Insights Into the Genetics of Inflammatory Bowel Disease", Gastroenterology, May 2011, pp. 1704-1712, vol. 140.
Chow J, et al. (2009) Getting the bugs out of the immune system: do bacterial microbiota "fix" intestinal T cell responses? Cell Host Microbe 5: 8-12.
Clemente et al., "Infliximab modifies mesenteric adipose tissue alterations and intestinal inflammation in rats with INBS-induced colitis," Scand. J. Gastroenterol., vol. 47, 943-50 (2012).
Cobb et al., Zwitterionic capsular polysaccharides: the new MHCII-dependent antigens. Cell Microbial. Oct. 2005;7(10): 1398-403. Review.

Collison et al., The inhibitory cytokine IL-35 contributes to regulatory T-cell function. Nature. Nov. 22, 2007;450(7169):566-9.
Communication pursuant to Article 94(3) EPC for European Application No. 08847489.5 filed in the name of California Institute of Technology, dated Aug. 7, 2013.
Comstock et al. Analysis of a capsular polysaccharide biosynthesis locus of Bacteroides fragilis. (1999) Infect Immun 67:3525-32.
Comstock et al., Bacterial glycans: key mediators of diverse host immune responses. Cell. Sep. 8, 2006;126(5):847-50.
Comstock et al., Interstrain variation of the polysaccharide B biosynthesis locus of Bacteroides fragilis: characterization of the region from strain 638R. J Bacterial. Oct. 1999 ;181(19):6192-6.
Conesa et al., Interleukin-2 induces peroxide production by primed normodense eosinophils of patients with asthma. Allergy Asthma Proc. Jan.-Feb. 2003;24(1):27-33.
Coombes et al., "Regulatory T cells and intestinal homeostasis", Immunol. Rev., Apr. 2005, pp. 184-194, vol. 204, Issue 1.
Coombes JL, et al. (2007) Control of intestinal homeostasis by regulatory T cells and dendritic cells. Semin Immunol 19: 116-126.
Coombes, JL, et al. (2007). A functionally specialized population of mucosal CD103+ DCs induces Foxp3+ regulatory T cells via a TGF-beta and retinoic acid-dependent mechanism. J Exp Med 204, 1757-1764.
Correale J, et al. (2011) Vitamin D-mediated immune regulation in multiple sclerosis. Journal of the neurological sciences 311:23-31.
Couper et al. "IL-10: The Master Regulator of Immunity to Infection" Journal of Immunology. 2008; 180:5771-5777.
Coussens & Werb, "Inflammation and cancer," Nature, vol. 420, 860-867 (2002).
Coyne et al., "Mpi recombinase globally modulates the surface architecture of a human commensal bacterium", PNAS, Sep. 2, 2003, pp. 10446-10451, vol. 100 No. 18.
Crabb et al., T cell regulation of Bacteroides fragilis-induced intraabdominal abscesses. Rev Infect Dis. Jan.-Feb. 1990;12 Suppl 2:S1 78-84. Review.
Craig, Autologous hematopoietic stem cell transplantation for Crohn's disease. Autoimmun Rev. Aug. 2002;1(4):244-9. Review.
Dadley-Moore, The sweet side of maturation. Nature Rev Immunol. Sep. 2005;5:674.
Dahiyat BI. et al., De nova protein design: fully automated sequence selection. Science (1997) 278:82-87.
Daniel et al. Immune Modulatory Treatment of Trinitrobenzene Sulfonic Acid Colitis with Calcitriol is Associated with a Change of a T Helper (Th) 1 /1Th17 to a Th2 and Regulatory T Cell Profile, in J. Pharmacology and Expet. Therapeutics, 2008, vol. 324, pp. 23-33.
Decision on Rejection for JP2010-533311 dated Oct. 29, 2013 in the name of California Institute of Technology. (English Translation+ Japanese Original).
Decision of Refusal dated Feb. 26, 2016 in Japanese Patent Application No. 2013-503958.
Decision of Refusal dated Nov. 27, 2018 in Japanese Patent Application No. 2016-513092.
Definition of "prevention" from the Institute for International Medical Education [online], [Retrieved on Mar. 24, 2011]. Retrieved from the internet, www.iime.org/glossary.htm. Published Feb. 2002, p. 1, 2, 26, 27 and 39.
Deib, Treating multiple sclerosis with monoclonal antibodies: a 2013 update. Expert Rev Neurother. Mar. 2013;13(3):313-35. doi: 10.1586/ern.13.17.
Denning, T. et al. "Lamina propria macrophages and dendritic cells differentially induce regulatory and interleukin 17-producing T cell responses" Nature Immunology; vol. 8; No. 10; Oct. 1, 2007; pp. 1086-1094.
Deslongchamps et al., "Ozonolysis of Acetals. (1) Ester Synthesis, (2) THP Ether Cleavage, (3) Selective Oxidation of B-Glycoside, (4) Oxidative Removal of Benzylidene and Ethylidene Protecting Groups". Canadian J of Chem. 1971;49:2465-2467.
Deslongchamps et al., The Importance of Conformation in the Ozonolysis of Acetals. Canadian J Chem. 1972;50:3402-3404.
Deslongchamps et al., The Oxidation of Acetals by Ozone. Canadian J Chem. 1974;52:3651-3664.

(56) References Cited

OTHER PUBLICATIONS

Dethlefsen et al. "An ecological and evolutionary perspective on human-microbe mutualism and disease", Nature, Oct. 18, 2007, pp. 811-818, 449.
Dias et al., Antisense oligonucleotides: Basic concepts and mechanisms. Mol. Cancer Therap., 2002, vol. 1:347-355.
Difabio et al., Structure of the Capsular Polysaccharide Antigen of Type IV Group B *Streptococcus*; Can. J. Chem. 67:877 (1989).
Dohi et al., "Type 1 and 2 T helper cell-mediated colitis", Current Opinion in Gastroenterology, Nov. 2006, pp. 651-657, vol. 22—Issue 6, Lippincott Williams & Wilkins, Philadelphia, PA.
Doig et al., The efficacy of the heat killing of *Mycobacterium tuberculosis*. J Clin Pathol. Oct. 2002;55(10):778-9.
Dong, "Diversification of T-helper-cell lineages: finding the family root of IL-17-producing cells", Nat Rev Immunol, Mar. 17, 2006, pp. 329-334, vol. 6, Issue 4.
Dooms et al., Revisiting the role of IL-2 in autoimmunity. Eur J Immunol. Jun. 2010;40(6):1538-40. doi: 10.1002/eji.201040617.
Duerr, R.H et al. Science vol. 314; 2006; pp. 1461.
Eisenstein et al. Integration host factor is required for the DNA inversion that controls phase variation in *E. coli*. Proc Natl. Acad. Sci. 84, 6506-6510, 1987.
Elson et al., "Monoclonal anti-interleukin 23 reverses active colitis in a T cell-mediated model in mice", Jun. 2007, pp. 2359-2370, vol. 132, Issue 7.
Elson, "Commensal bacteria as targets in Crohn's disease" Gastroenterology Jul. 2000, pp. 254-257, vol. 119, Issue 1.
European Communication pursuant to Article 94(3) EPC dated Feb. 5, 2014 for European application 10767863.3 filed on Apr. 23, 2010 in the name of California Institute of Technology. 7 pages.
European Communication pursuant to Rules 70(2) and 70a(2) EPC dated Dec. 27, 2010 for European application 08847489.5 filed on Nov. 9, 2008 in the name of California Institute of Technology. 7 pages.
European Communication pursuant to Rules 70(2) and 70a(2) EPC dated Feb. 12, 2013 for European application 10767863.3 filed on Apr. 23, 2010 in the name of California Institute of Technology. 1 page.
Extended European Search Report for European Application No. 10767863.3 dated Jan. 24, 2013. 10 pages.
European Search Report dated Jan. 30, 2015 for European application 10767863.3 filed on Apr. 23, 2010 in the name of California Institute of Technology. 5 pages.
Extended European Search Report for the European Application No. 11784368.0, dated Dec. 2, 2013, 13 pages.
Examination Report dated May 5, 2017 in European Patent Application No. 08847489.
Examination Report for European patent application No. 11784368.0. dated Jul. 8, 2016. 7 pages.
Examination Report dated Jan. 24, 2018 in European Patent Application No. 147952048.
Examination Report dated Jan. 18, 2019 in European Patent Application No. 147952048.
Examination Report dated Sep. 23, 2014 in European Patent Application No. 11766746.9.
Examination Report dated Nov. 10, 2015 in European Patent Application No. 11766746.9.
Extended European Search Report dated Sep. 13, 2013 in European Application No. 11766746.9.
Extended European Search Report dated Dec. 8, 2018 in European Application No. 08847489.
Extended European Search Report for Application No. 12811896.5, dated Jun. 1, 2015. 11 pages.
Extended European Search Report for European Application No. 12837738.9 dated Mar. 18, 2015 8 pages.
Extended European Search Report for European Application No. 14795204.8, dated Dec. 8, 2016, 9 pages.
Falk, P.G., et al. (1998). Creating and maintaining the gastrointestinal ecosystem: what we know and need to know from gnotobiology. Microbiol Mol Biol Rev 62, 1157-1170.

Feuerer et al., "Foxp3+ regulatory T cells: differentiation, specification, subphenotypes", Nat Immunol., Jun. 18, 2009, pp. 689-695, vol. 10, Issue 7.
Final Office Action issued in U.S. Appl. No. 10/814,620, filed Mar. 31, 2004 in the name of Arthur O. Tzianabos, dated Oct. 7, 2009.
Final Office Action for U.S. Appl. No. 12/267,602, filed Nov. 9, 2008 on behalf of Sarkis K. Mazmanian et al, dated Feb. 6, 2012. 15 pages.
Final Office Action for U.S. Appl. No. 12/766,787, filed Apr. 23, 2010 on behalf of June L. Round et al, dated Aug. 4, 2015. 29 pages.
Final Office Action for U.S. Appl. No. 12/766,787, filed Apr. 23, 2010 on behalf of June L. Round et al, dated Nov. 26, 2012. 12 pages.
Final Office Action for U.S. Appl. No. 12/831,131, filed Jul. 6, 2010 on behalf of June L. Round et al, dated Jun. 10, 2013. 23 pages.
Final Office Action for U.S. Appl. No. 13/082,183, filed Apr. 7, 2011 on behalf of Yue Shen et al, dated Jan. 9, 2014. 9 pages.
Final Office Action for U.S. Appl. No. 13/112,725, filed May 20, 2011 on behalf of June L. Round, dated Jan. 7, 2015. 15 pages.
Final Office Action for U.S. Appl. No. 13/112,725, filed May 20, 2011 on behalf of June L. Round, dated Oct. 24, 2013. 8 pages.
Final Office Action for U.S. Appl. No. 13/112,725, filed May 20, 2011 on behalf of California Institute of Technology, dated Nov. 2, 2016. 29 Pages.
Final Office Action for U.S. Appl. No. 13/360,702, filed Jan. 28, 2012 on behalf of Sarkis K. Mazmanian et al, dated Dec. 3, 2013. 14 pages.
Final Office Action for U.S. Appl. No. 13/464,876, filed May 4, 2012 on behalf of Sarkis K. Mazmanian et al, dated Feb. 20, 2014. 20 pages.
Final Office Action for U.S. Appl. No. 13/573,695, filed Oct. 3, 2012 on behalf of Sarkis K. Mazmanian et al, dated Jan. 28, 2014. 12 pages.
Final Office Action dated Dec. 28, 2017 in U.S. Appl. No. 14/660,827.
Final Office Action dated Jun. 15, 2018 in U.S. Appl. No. 14/264,607.
Final Office Action dated Oct. 22, 2018 in U.S. Appl. No. 14/803,598.
Final Office Action dated Jun. 28, 2019 in U.S. Appl. No. 15/179,810.
Finberg et al., Decay-accelerating factor expression on either effector or target cells inhibits cytotoxicity by human natural killer cells. J Immunol. Sep. 15, 1992;149(6):2055-60.
Fink, et al. "Human antigen-presenting cells respond differently to gut-derived probiotic bacteria but mediate similar strain-dependent NK and T cell activation" FEMS Immunology and Medical Microbiology, 2007, vol. 51, No. 3; pp. 535-546.
Fontenot et al., "Regulatory T cell lineage specification by the forkhead transcription factorfoxp3", Immunity, Mar. 2005, pp. 329-341, vol. 22, Issue 3.
Fontenot, J.D., et al. (2003). Foxp3 programs the development and function of CD4+CD251 + regulatory Tcells. Nat Immunol 4, 330-336.
Fournier et al., Isolation of type 5 capsular polysaccharide from *Staphylococcus aureus*. Ann Inst Pasteur Microbial. Sep.-Oct. 1987;138(5):561-7.
Frank et al., "Molecular-phylogenetic characterization of microbial community imbalances in human inflammatory bowel diseases", Proc Natl Acad Sci USA, Aug. 21, 2007, pp. 13780-13785, vol. 104 No. 34.
Fridkis-Hareli et al., Binding motifs of copolymer 1 to multiple sclerosis- and rheumatoid arthritis-associated HLA-DR molecules. J Immunol. Apr. 15, 1999;162(8):4697-704.
Fridkis-Hareli et al., Binding of random copolymers of three amino acids to class 11 MHC molecules. Int Immunol. May 1999;11(5):635-41.
Fridkis-Hareli et al., Direct binding of myelin basic protein and synthetic copolymer 1 to class 11 major histocompatibility complex molecules on living antigen-presenting cells—specificity and promiscuity. Proc Natl Acad Sci USA. May 24, 1994;91(11):4872-6.
Fridkis-Hareli et al., Synthetic copolymer 1 and myelin basic protein do not require processing prior to binding to class 11 major histocompatibility complex molecules on living antigen-presenting cells. Cell Immunol. Jul. 1995;163(2):229-36.

(56) References Cited

OTHER PUBLICATIONS

Froicu, M. et al. "A crucial role for the vitamin D receptor in experimental inflammatory bowel diseases" Mol. Endocrinol, 2003. 17(12) oo.2386-2392.
Froicu, M., et al. Vitamin D receptor is required to control gastro-intestinal immunity in IL-10 knockout mice. Immunology, 2006. 117(3) p. 310-8.
Fujino et al., "Increased expression of interleukin 17 in inflammatory bowel disease", Gut, 2003; pp. 65-70, 52, BMJ Publishing Group, London, United Kingdom.
Gaboriau-Rauthiau et al., "The key role of segmented filamentous bacteria in the coordinated maturation of gut helper T cell responses", Immunity, Oct. 16, 2009, pp. 677-689, vol. 31, Issue 4.
Gallorini, et al., "Toll-like receptor 2 dependent immunogenicity of glycoconjugate vaccines containing chemically derived zwitterionic polysaccharides, "PNAS vol. 106: 17481-17486.Oct. 13, 2009. 6 Pages.
Gally DL et al. Environmental regulation of the fim switch controlling type 1 fimbrial phase variation in *Escherichia coli* K-12: effects of temperature and media. (1993) J Bacteriol 175:6186-93.
Garrett et al., "Colitis-Associated Colorectal Cancer Driven by T-bet Deficiency in Dendritic Cells," Cancer Cell, vol. 16, 208-19 (2009).
Garrett et al., "Enterobacteriaceae Act in Concert with the Gut Microbiota to Induce Spontaneous and Maternally Transmitted Colitis," Cell Host Microbe, vol. 8, 292-300 (2010).
Gelu-Simeon, et al., Evaluation and predictive factors of thyroid disorder due to interferon alpha in the treatment of hepatitis C. World J Gastroenterol 2009; 15(3):328-333.
GenBank Accession No. AJ277832; Hutloff Jan. 19, 2001.
GenBank Accession No. CAC06612; Hutloff Jan. 19, 2001.
GenBank Accession No. NM012092; Dec. 20, 2003.
GenBank Accession No. NP036224; Dec. 20, 2003.
Gerard et al., "Interleukin 10 reduces the release of tumor necrosis factor and prevents lethality in experimental endotoxemia", J. Exp. Med., Feb. 1, 1993, pp. 547-550,177 (2): 547.
Gibson 111 et al., The capsular polysaccharide complex of Bacteroides fragilis induces cytokine production from human and murine phagocytic cells. Infect Immun. Mar. 1996;64(3): pp. 1065-1069.
Gibson et al., "Chapter 5: trans-Galactooligosaccharides as Prebiotics". Handbook of Functional Dairy Products. Edited by Colette Shortt and John O'Brien. Published by CRC Press. 2004. 18 pages.
Gilbert et al., "Toward Effective Probiotics for Autism and other Neurodevelopmental Disorders", Cell, Dec. 19, 2013, pp. 1446-1448,vol. 155, Issue 7.
Gill et al., "Metagenomic analysis of the human distal gut microbiome", Science, Jun. 2, 2006, pp. 1355-1359, vol. 312, Issue 5778.
Glazebrook et al., A novel exopolysaccharide can function in place of the calcofluor-binding exopolysaccharide in nodulation of alfalfa by Rhizobium meliloti. Cell. Feb. 24, 1989;56(4):661-672.
Golgher et al., Galactofuranose-containing glycoconjugates of epimastigote and trypomastigote forms of Trypanosoma cruzi. Mol Biochem Parasitol. Aug. 1993;60(2):249-64.
Gondek, D.C., et al. (2005). Cutting edge: contact-mediated suppression by CD4+CD25+ regulatory cells involves a granzyme B-dependent, perforin-independent mechanism. J. Immunol.; vol. 174, 1783-1786.
Gonzalez-Hernandez et al., Peripheral blood CD161 + T cells from asthmatic patients are activated during asthma attack and predominantly produce IFN-gamma. Scand J Immunol. Apr. 2007;65(4):368-75.
Goverman J (2009) Autoimmune T cell responses in the central nervous system. Nat Rev Immunol 9: 393-407.
Goverman J, et al. (1993) Transgenic mice that express a myelin basic protein- specific T cell receptor develop spontaneous autoimmunity. Cell 72: 551-560.
Grabow, Bacteriophages: Update on application as models for viruses in water. Water SA 2001 ;27(2):251-268.
Greenberger, Drug allergy, J Allergy Clin Immunol, Feb. 2006, pages S464-S470, vol. 117, Issue 2, Supplement 2.

Grivennikov et al., "IL-6 and Stat3 Are Required for Survival of Intestinal Epithelial Cells and Development of Colitis-Associated Cancer," Cancer Cell, vol. 15, 103-113 (2009).
Groux et al., "A CD4+ T-cell subset inhibits antigen-specific T-cell responses and prevents colitis", Nature, Oct. 16, 1997, pp. 737-742, 389.
Groux et al., Type I T-regulatory cells: their role in the control of immune responses. Transplantation. May 15, 2003;75(9 Suppl):8S-12S.
Hafler et al., Anti-CD4 and anti-CD2 monoclonal antibody infusions in subjects with multiple sclerosis. Immunosuppressive effects and human anti-mouse responses. J Immunol. Jul. 1, 1988;141(1):131-8.
Hall, J.A., et al. (2008). Commensal DNA limits regulatory T cell conversion and is a natural adjuvant of intestinal immune responses. Immunity 29, 637-649.
Hamelmann et al., Noninvasive measurement of airway responsiveness in allergic mice using barometric plethysmography. Am J Respir Crit Care Med. Sep. 1997;156(3 Pt 1):766-75.
Hampe, J., et al. (2001 ). Association between insertion mutation in NOD2 gene and Crohn's disease in German and British populations. Lancet 357. 1925-1928.
Hampe, J., et al. (2007). A genome-wide association scan of nonsynonymous SNPs identifies a susceptibility variant for Crohn disease in ATG 16L 1. Nat Genet 39, 207-211.
Haregewoin et al., Human gamma delta+ T cells respond to mycobacterial heat-shock protein. Nature. Jul. 27, 1989;340(6231):309-12.
Harrington L. et al., "Interleukin 17-producing CD4+ effector T cells develop via a lineage distinct from the T helper type 1 and 2 lineages" i Nature Immunologyl , Nov. 2005, vol. 6, No. 11, pp. 1123-1132, 10 pages.
Harth et al. Treatment of mycobacterium tuberculosis with antisense oligonucleotides to glutamine synthetase mRNA inhibits glutamine synthetase activity, formation of poly-L glutamate/glutamine cell wall structure, and bacterial replication. Proc Natl. Acad. Sci. 97: 418-423, 2000.
He, B.,et al. (2007). Intestinal bacteria trigger T cell-independent immunoglobulin A(2) class switching by inducing epithelial-cell secretion of the cytokine April. Immunity 26, 812-826.
Hertl et al., T cell control in autoimmune bullous skin disorders. J Clin Investi. May 2006; 116(5): 1159-66. Review.
Hewison M, et al. (2003) Differential regulation of vitamin D receptor and its ligand in human monocyte-derived dendritic cells. J Immunol 170: 5382-5390.
Hirata et al., Cytokine synthesis of human monocytes stimulated by triple or single helical conformer of an antitumour (1->3)-beta-D-glucan preparation, sonifilan. Zentralbl Bakteriol. Nov. 1998;288(3):403-13.
Hodge et al., *Allium sativum* (garlic) suppresses leukocyte inflammatory cytokine production in vitro: potential therapeutic use in the treatment of inflammatory bowel disease. Cytometry. Aug. 1, 2002;48(4):209-15.
Hofstetter et al., Th17 Cells in MS and Experimental Autoimmune Encephalomyelitis. Int MS J. Apr. 2009;16(1):12-8.
Hooper, L.V. (2009). Do symbiotic bacteria subvert host immunity? Nat Rev Microbiol 7, 367-374.
Hooper, L.V. et al. (2001) Commensal host-bacterial relationships in the gut. Science 292, 1115-1118.
Hori, S et al. "Control of regulatory T cell development by the transcription factor Foxp3" Science vol. 299, No. 5609 pp. 1057-1061 (2003).
Hu et al., "Inflammation-induced tumorigenesis in the colon is regulated by caspase-1 and NLRC4," Proc. Natl. Acad. Sci., vol. 107, 21635-21640 (2010).
Hue et al., Interleukin-23 drives innate and T cell-mediated intestinal inflammation:, J Exp Med., Oct. 9, 2006, pp. 2473-2483, 203 (11).
Huibregtse et al.., Immunopathogenesis of IBD: insufficient suppressor function in the gut? Gut. Apr. 2007;56(4):584-92. Epub Oct. 17, 2006.
Hutloff et al., ICOS is an inducible T-cell co-stimulator structurally and functionally related to CD28. Nature. Jan. 21, 1999;397(6716):263-6.

(56) References Cited

OTHER PUBLICATIONS

International Preliminary Report on Patentability for Application No. PCT/US2008/082928, dated May 11, 2010, 6 pages.
International Preliminary Reporton Patentability for Application No. PCT/US2010/032300, dated Oct. 25, 2011, 6 pages.
International Preliminary Report on Patentability for Application No. PCT/US2012/023050, dated Jul. 30, 2013, 5 pages.
International Preliminary Report on Patentability for Application No. PCT/US2014/037392 dated Nov. 10, 2015.8 pages.
International Preliminary Report on Patentability for International Application No. PCT/US2016/037044 filed Jun. 10, 2016 on behalf of California Institute of Technology, dated Dec. 12, 2017. 9 pages (English Only).
International Search Report for International Application PCT/US2016/037044 filed Jun. 10, 2016 on behalf of California Institute of Technology, dated Sep. 22, 2016. 4 pages.
International Search Report and Written Opinion for Application No. PCT/US2011/037476, dated Aug. 26, 2011, 9 pages.
Isaksson et al., Conditional DC depletion does not affect priming of encephalitogenic Th cells in EAE. Eur J Immunol. Oct. 2012;42(10):2555-63. doi: 10.1002/eji.201142239. Epub Aug. 8, 2012.
Ishikawa, H. et al., "Effect of intestinal microbiota on the induction of regulatory CD25 CD4+ T+ cells" Clin Exp Immunol 153, 127-135 (2008).
Itokazu et al., Abscess formation as a complication caused by postoperative osteomyelitis of the femur. Arch Orthop Trauma Surg. 1998;118(1-2):99-102. Review.
Itzowitz & Harpaz, "Diagnosis and Management of Dysplasia in Patients With Inflammatory Bowel Diseases," Gastroenterology, vol. 126, 1634-1648 (2004).
Ivanov et al., "Induction of intestinal Th17 cells by segmented filamentous bacteria", Cell, Oct. 15, 2009, pp. 485-498, vol. 139, Issue 3, Elsevier Inc., Amsterdam, Netherlands.
Ivanov et al., "Specific microbiota direct the differentiation of IL-17-producing T-helper cells in the mucosa of the small intestine", Cell Host Microbe, Oct. 16, 2008, pp. 337-349, vol. 4, Issue 4.
Ivanov et al., "Transcriptional regulation of Th17 cell differentiation", Semin Immunol, Dec. 2007, pp. 409-417, vol. 19, Issue 6.
Ivanov, 11. et al. "The Orphan Nuclear Receptor RORyt Directs the Differentiation Program of Proinflammatory IL-17+ T Helper Cells" Cell 126; 1121-1133 (2006).
Izcue et al., "Regulatory T cells suppress systemic and mucosal immune activation to control intestinal inflammation", Immunol Rev., Aug. 2006, pp. 256-271, vol. 212, Issue 1.
Izcue, A., et al. (2009). Regulatory lymphocytes and intestinal inflammation. Annu Rev Immunol 27, 313-338.
Japanese Decision of Rejection dated Oct. 29, 2013 for Japanese application 2010-533311 filed on Apr. 23, 2010 in the name of California Institute of Technology.
Japanese Notice for Reasons for Rejection dated Mar. 24, 2015 for Japanese application 2014-038746 filed on Nov. 9, 2008 in the name of California Institute of Technology.
Japanese Notification of Reasons for Refusal dated Feb. 12, 2014 for Japanese application 2012-507451 filed on Apr. 23, 2010 in the name of California Institute of Technology.
Japanese Official Decision of Refusal dated Feb. 10, 2015 for Japanese application 2012-507451 filed on Apr. 23, 2010 in the name of California Institute of Technology.
Jawad et al., "Inflammatory Bowel Disease and Colon Cancer," Recent Results Cancer Rec., vol. 185, 99-115(2011).
Jeffery LE, et al. (2009) 1,25-Dihydroxyvitamin D3 and IL-2 combine to inhibit T cell production of inflammatory cytokines and promote development of regulatory T cells expressing CTLA-4 and FoxP3. J Immunol 183: 5458-5467.
Jennings et al., Immunochemistry of groups A, B, and C meningococcal polysaccharide-tetanus toxoid conjugates. J Immunol. Sep. 1981;127(3): 1011-8.

Jennings et al., Induction of meningococcal group B polysaccharide-specific IgG antibodies in mice by using an N-propionylated B polysaccharide-tetanus toxoid conjugate vaccine. J Immunol. Sep. 1, 1986;137(5):1708-13.
Jia et al., Gut microbiota: a potential new territory for drug targeting. Nat Rev Drug Discov. Feb. 2008;7(2):123-9. doi: 10.1038/nrd2505.
Johnson et al., Bacterial capsular polysaccharide prevents the onset of asthma through T-cell activation. Glycobiology. Apr. 2015;25(4):368-75. doi: 10.1093/glycob/cwul 17. Epub Oct. 27, 2014.
Jonuleit et al., Identification and functional characterization of human CD4(+)CD25(+) T cells with regulatory properties isolated from peripheral blood. J Exp Med. Jun. 4, 2001 ;193(11):1285-94.
Jonuleit et al., The regulatory T cell family: distinct subsets and their interrelations. J Immunol. Dec. 15, 2003;171(12):6323-7.
Joshi S, et al. (2011) 1,25-dihydroxyvitamin 0(3) ameliorates Th17 autoimmunity via transcriptional modulation of interleukin-17A. Molecular and cellular biology 31: 3653-3669.
Jotwani et al., Pathogenicity of Bacteroides fragilis group in rat intra-abdominal abscesses. Microbial Immunol. 1992;36(10):1041-9.
Jyonouchi, "Non-IgE Mediated Food Allergy", Inflammation & Allergy-Drug Targets, Sep. 2008, pp. 173-180. vol. 7, No. 3.
Kakalacheva K, et al. (2011) Environmental triggers of multiple sclerosis. FEBS letters 585: 3724-3729.
Kakalacheva K, et al. (2011) Viral triggers of multiple sclerosis. Biochimica et biophysica acta 1812: 132-140.
Kalka-Moll et al., "Effect of Molecular Size on the Ability of Zwitterionic Polysaccharides to Stimulate Cellular Immunity," J. Immunol., vol. 164, 719-24 (2000).
Kalka-Moll et al., "Zwitterionic Polysaccharides stimulate T cells by MHC class II-Dependent Interactions", The Journal of Immunology, Dec. 1, 2002, pp. 6149-6153, vol. 169, Issue 11.
Kalka-Moll et al., Bacteriodes Fragilis NCTC 9343 Capsular Polysaccharide PS A and the Effect of Chain Length of T cell Proliferation. Abstracts of the 98th Gen Mtg of the American Soc for Microbial. 1998;98:123. Abstract B-405.
Kalka-Moll et al., Immunochemical and biological characterization of three capsular polysaccharides from a single Bacteroides fragilis strain. Infect Immun. Apr. 2001:69(4):2339-44.
Kasper et al., Capsular polysaccharides and lipopolysaccharides from two Bacteroides fragilis reference strains: chemical and immunochemical characterization. J Bacterial. Feb. 1983;153(2):991-7.
Kasper et al., Protective efficacy of immunization with capsular antigen against experimental infection with Bacteroides fragilis. J Infect Dis. Nov. 1979;140(5):724-3 I.
Kasper et al., Surface antigens as virulence factors in infection with Bacteroides fragilis. Rev Infect Dis. Mar.-Apr. 1979;1(2):278-90.
Kasper et al., The polysaccharide capsule of Bacteroides fragilis subspecies fragilis: immunochemical and morphologic definition. J Infect Dis. Jan. 1976;133(1):79-87.
Kato et al., Interleukin 10 reduces mortality from severe peritonitis in mice. Antimicrob Agents Chemother. Jun. 1995;39(6):1336-40.
Kayama H. et al., "Regulation of intestinal homeostasis by innate and adaptive immunity" International Immunology, vol. 24, No. 11, pp. 673-680,Sep. 2012, 8 pages.
Kennedy et al., Prevention of experimental postoperative peritoneal adhesions by N,0-carboxymethyl chitosan. Surgery. Nov. 1996; 120(5):866-70.
Kernodle et al. Expression of an antisense hla fragment in *Staphylococcus aureus* reduces alphatoxin production in vitro and attenuates lethal activity in a murine model. Infection and Immunity 179-184. 1997.
Kidd, "Th1/Th2 Balance: The hypothesis, its limitations, and implications for health and disease", Alternative Medicine Review, 2003, pp. 223-246, vol. 8, No. 3, Thorne Research, Inc., Dover, ID.
Kim, J.M., et al. (2007). Regulatory T cells prevent catastrophic autoimmunity throughout the lifespan of mice. Nat Immunol 6, 191-197.
Kinoshita et al., Retinoic acid reduces autoimmune renal injury and increases survival in NZB/W FI mice. J Immunol. Jun. 1, 2003;170(11):5793-8.

(56) References Cited

OTHER PUBLICATIONS

Kirjavainen et al. "Healthy gut microflora and allergy: factors influencing development of the microbiota" Ann Med., 1999, pp. 288-292, vol. 31, Issue 4.
Knetsch et al., Polymers with tunable toxicity: a reference scale for cytotoxicity testing of biomaterial surfaces. J Biomed Mater Res A. Sep. 15, 2007;82(4):947-57.
Knirel et al., Somatic antigens of Pseudomonas aeruginosa. The structure of O-specific polysaccharide chains of lipopolysaccharides of P. aeruginosa O3 (Lanyi), O25 (Wokatsch) and Fisher immunotypes 3 and 7. Eur J Biochem. Sep. 15, 1987;167(3):549-61.
Knirel et al., The structure of O-specific polysaccharides and serological classification of Pseudomonas aeruginosa (a review). Acta Microbial Hung. 1988;35(1):3-24. Review.
Koch, M.A., et al. (2009). The transcription factor T-bet controls regulatory T cell homeostasis and function during type 1 inflammation. Nat Immunol 10, 595-602.
Kong, J., et al., Novel role of the vitamin D receptor in maintaining the integrity of the intestinal mucosal barrier. Am J Physiol Gastrointest Liver Physiol, 2008. 294(1): p. G208-16.
Kormelink et al., "Atopic and non-atopic allergic disorders: current insights into the possible involvement of free Immunoglobulin light chains", Clinical and Experimental Allergy, Jan. 2009, pp. 33-42, vol. 39, Issue 1.
Krause et al., An Inhibitor of Cell Proliferation Associated with Adhesion Formation Is Suppressed by N,0-Carboxymethyl Chitosan. J Investi Surg. 1988;11:105-113.
Krutzik SR, et al. (2008) "IL-15 links TLR2/1-induced macrophage differentiation to the vitamin D-dependent antimicrobial pathway". J Immunol 181: 7115-7120.
Kuehn, M.J et al. "Bacterial outer membrane vesicles and the host-pathogen interaction" Genes and Development vol. 19, No. 22 pp. 2645-2655 (2005).
Kuhn et al., "Interleukin-10 deficient mice develop chronic enterocolitis", Cell, Oct. 22, 1993, pp. 263-274, vol. 75, Issue 2.
Kulicke et al., Correlation between immunological activity, molar mass, and molecular structure of different (1->3)-beta-D-glucans. Carbohydr Res. Jan. 2, 1997;297(2):135-43.
Kullberg et al., "IL-23 plays a key role in Helicobacter hepaticus-induced T cell-dependent colitis", J Exp Med., Oct. 9, 2006, pp. 2485-2494, 203 (11): 2485.
Kullberg et al., "Bacteria-triggered CD4(+) T regulatory cells suppress Helicobacter hepaticus-induced colitis", J Exp Med., Aug. 19, 2002, pp. 505-515, 196 (4): 505.
Kullberg et al., "Helicobacter hepaticus Triggers Colitis in Specific-Pathogen-Free Interleukin-10 (IL-10)-Deficient Mice through an IL-12- and Gamma Interferon-Dependent Mechanism", Infection and Immunity Nov. 1998, pp. 5157-5166, vol. 66 No. 11.
Kullberg et al., "Induction of colitis by a CD4+ T cell clone specific for a bacterial epitope", Proc Natl Acad Sci USA, Dec. 23, 2003, pp. 15830-15835, vol. 100 No. 26.
Kuper et al., "Infections as a major preventable cause of human cancer," J. Intern. Med., vol. 248, 171-183(2000).
Kurup et al., Antibody response to low-molecular-weight antigens of Aspergillus fumigatus in allergic bronchopulmonary aspergillosis. J Clin Microbial. Jun. 1989;27(6):1312-6.
Lagishetty, V et al. "Vitamin D deficiency in mice impairs colonic antibacterial activity and predisposes to colitis." Endocrinology.; Jun. 2010; vol. 151(6) pp. 2423-2432.
Lee et al., "Bacterial colonization factors control specificity and stability of the gut microbiota," Nature, vol. 501, 426-429 (2013).
Lee et al., Clinical Chemistry and Laboratory Medicine, Jul. 1, 2008, pp. 997-1003, vol. 46, No. 7., Watler de Gruyter GmbH, Berlin, Germany.
Lee et al., Effects of In Vitro and In Vivo and Growth Conditions on Expression of Type 8 Capsular Polysaccharide by *Staphylococcus aureus*, Infection and Immunity, 61:1853-1858, 1993.
Lee S.A., et al., "Plasma Interleukin-1beta, -6, -8 and Tumor Necrosis Factor-alpha as Highly Informative Markers of Pelvic Inflammatory Disease," Clinical Chemistry and Laboratory Medicine, Jul. 2008, vol. 46 (7), 3 pages.
Lee YK, et al. (2010) Has the microbiota played a critical role in the evolution of the adaptive immune system? Science 330: 1768-1773.
Lee YK, et al. (2011) Proinflammatory T-cell responses to gut microbiota promote experimental autoimmune encephalomyelitis. Proc Natl Acad Sci U S A 108 Suppl 1:4615-4622.
Ley et al., "Ecological and evolutionary forces shaping microbial diversity in the human intestine", Cell, Feb. 24, 2006, pp. 837-848,vol. 124, Issue 4.
Ley et al., Evolution of mammals and their gut microbes. Science. Jun. 20, 2008;320(5883): 1647-51. doi: 10.1 126/science. 1155725. Epub May 22, 2008.
Lin et al., "Regulatory T cell development in the absence of functional Foxp3", Nat. Immunol., Mar. 2007, pp. 359-368, vol. 8, Issue 4, Nature Publishing, London, United Kingdom.
Lindberg et al., Virulence factors in infections with bacteroides fragilis: isolation and characterization of capsular polysaccharide and lipopolysaccharide. Scand J Infect Dis Suppl. 1982;35:45-52.
Liu et al., "Regulation of surface architecture by symbiotic bacteria mediates host colonization", Proc Natl Acad Sci USA, Mar. 11, 2008, pp. 3951-3956, vol. 105 No. 10.
Liu et al., "Toll-like receptor 2 signaling modulates the functions of CD4+ CD25+ regulatory T cells", Proc. Natl. Acad. Sci. USA, May 2, 2006, pp. 7048-7053, vol. 103 No. 18.
Liu P.T., et al., "Toll-like Receptor Triggering of a Vitamin D-mediated Human Antimicrobial Response," Science, Mar. 2006, vol. 311 (5768), 5 pages.
Liu, N. et al. "Altered endocrine and autocrine metabolism of vitamin D in a mouse model of gastrointestinal inflammation." Endocrinology, 2008; 149(10): pp. 4799-4808.
Liu et al., "Glucuronoxylomannan promotes the generation of antigen-specific T regulatory cell that suppresses the antigen-specific Th2 response upon activation,", J. Cell. Mol. Med. vol. 13:1765-1774.Online Nov. 2008. 10 Pages.
Lysnyansky et al. Juxtaposition of an active promoter to via genes via site-specific DNA inversions generates antigenic variation in Mycoplasma bovis. (2001) J Bacteriol 183:5698-5708.
MacPherson et al., IgA responses in the intestinal mucosa against pathogenic and nonpathogenic microorganisms. Microbes Infect. Oct. 2001;3(12):1021-35.
MacPherson et al., Interactions between commensal intestinal bacteria and the immune system. Nat Rev Immunol. Jun. 2004;4(6):478-85.
MacPherson et al., Mucosal antibodies in inflammatory bowel disease are directed against intestinal bacteria. Gut. Mar. 1996;38(3):365-75.
MacPherson, A.J. et al. (2004). Induction of protective IgA by intestinal dendritic cells carrying commensal bacteria. Science 303, 1662-1665.
Maier, B.R., et al. (1972). Experimental Shigella infections in laboratory animals. I. Antagonism by human normal flora components in gnotobiotic mice. Infect Immun 6, 168-173.
Makela et al., IL-10 is necessary for the expression of airway hyperresponsiveness but not pulmonary inflammation after allergic sensitization. Proc Natl Acad Sci USA. May 23, 2000;97(11 ):6007-12.
Maloy et al., "CD4+CD25+ T(R) cells suppress innate immune pathology through cytokine-dependent mechanisms", J Exp Med., Jan. 6, 2003, pp. 111-119, 197.
Mamessier et al., "Cytokines in atopic diseases: revisiting the Th2 dogma" Eur J Dermatol. Mar.-Apr. 2006;16(2):pp. 103-113.
Mantovani et al., "Cancer-related inflammation," Nature, vol. 454, 436-444 (2008).
Maynard CL, et al. (2009) Contrasting roles for all-trans retinoic acid in TGF-beta-mediated induction of Foxp3 and IL10 genes in developing regulatory T cells. The Journal of experimental medicine 206: 343-357.
Maynard et al., "Diversity in the contribution of interleukin-10 to T-cell-mediated immune regulation", Immunol. Rev., Dec. 2008 , pp. 219-233, vol. 226, Issue 1.

(56) References Cited

OTHER PUBLICATIONS

Maynard, C.L., et al. (2007). Regulatory T cells expressing interleukin 10 develop from Foxp3+ and Foxp3-precursor cells in the absence of interleukin 10. Nat Immunol 8, 931941.

Mayne CG, et al. (2011) "1,25-Dihydroxyvitamin D3 acts directly on theT lymphocyte vitamin D receptor to inhibit experimental autoimmune encephalomyelitis". European journal of immunology 41: 822-832.

Mazmanian et al., "Bacterial Immunomodulatory Regulation during Mammalian Health and Disease", Harvard Medical School, Brigham and Women's Hospital. (Oct. 11, 2005).

Mazmanian et al., "The Evolution of Symbiosis: From Bacteria to Commensal to Beneficial Microbe", Nature, May 29, 2008, pp. 620-625, 453.

Mazmanian et al., "The love-hate relationship between bacterial polysaccharides and the host immune system", Nature Reviews Immunology, Nov. 2006, pp. 849-858, vol. 6, No. 11.

Mazmanian et al., Capsular polysaccharides of symbiotic bacteria modulate immune responses during experimental colitis. J Pediatr Gasliventerol Nutr. Apr. 2008;46 Suppl 1:E11-2. doi: 10.1097/01.mpg.0000313824.70971.a7.

Mazmanian, S.K. Host-bacterial symbiosis prevents intestinal inflammatory disease. California Institute of Technology. Amgen (Jul. 2008).

McClain et al. Inversion-independent phase variation of type 1 fimbriae in *Escherichia coli*. (1993) J Bacteriol 175(14):4335-44.

McMurchy A.N., et al. (2012) Suppression assays with human T regulatory cells: a technical guide. European journal of immunology 42: 27-34.

Meisel-Mikolajczyk et al., Human T cell adhesion to endothelium stimulated by membrane components extracted from strains of Bacteroides vulgatus (member of B. fragilis group). Arch Immunol Ther Exp (Warsz). 1993;41 (2):129-31.

Meltzer, et al., "Pneumococcal Polysaccharides Interact with Human Dendritic Cell,". Infect. Immun. Vol. 74:1890-1895. Mar. 2006. 7 Pages.

Merriam-Webster. Hypothesize. 2013. Web http://www.merriam-webster.com/dictionary/hypothesize.

Merriam-Webster. Suggest. 2013. Web<http://www.merriam-websler.com/diclionary/suggesl>.

Mertens, J., et al., *Streptococcus pneumoniae* Serotype 1 Capsular Polysaccharide Induces CD8+CD28-Regulatory T Lymphocytes by TCR Crosslinking, PLOS Pathogens, (Sep. 2009) vol. 5, Issue 9, e1000596, p. 1-15.

Miller et al., Severe asthma and the omalizumab option. Clinical and Molecular Allergy 2008, 6:4.

Min, B., et al. (2007). Gut flora antigens are not important in the maintenance of regulatory T cell heterogeneity and homeostasis. Eur. J. Immunol. 37; pp. 1816-1923.

Mojtabavi et al., Long-lived Th2 memory in experimental allergic asthma. J Immunol. Nov. 1, 2002; 169(9):4 788-96.

Montz et al., Interleukin 10: ability to minimize postoperative intraperitoneal adhesion formation in a murine model. Fertil Steril. Jun. 1994;61(6):1136-40.

Moore, The List Goes On, New Additions to the Autoimmune Disease Raster. http://autoimmunedisease.suitelOI.com/blog.cfm/the list goes on. pp. 1-3. Aug. 7, 2007.

Moorman et al., National Surveillance of Asthma: United States, 2001 -2010. National Center for Health Statistics. Vital Health Stat. 2012;3(35) 67 pages.

Mor et al., Identification of aldolase as a target antigen in Alzheimer's disease. J Immunol. Sep. 1, 2005; 175(5):3439-45.

Mora et al., Generation of gut-homing IgA-secreting B cells by intestinal dendritic cells. Science. Nov. 17, 2006;314(5802):1157-60.

Mora et al., Selective imprinting of gut-homing T cells by Peyer's patch dendritic cells. Nature. Jul. 3, 2003;424(6944):88-93.

Morales-Tirado V, et al. (2011) 1 alpha,25-dihydroxyvitamin D3 (vitamin D3) catalyzes suppressive activity on human natural regulatory T cells, uniquely modulates cell cycle progression, and augments FOXP3. Clinical immunology 138: 212-221.

Motta, A.C. et al. (2006) T cells in asthma: Lessons from mouse models. Drug Discovery Today: Disease Models, vol. 3, No. 3; pp. 199-204.

Mulholland et al., Strategies for the control of pneumococcal diseases. Vaccine. Jul. 30, 1999;17 Suppl 1:S79-84. Review.

Nagaraj S. et al., "Reciprocal Relationship between Myeloid-Derived Suppressor Cells and T Cells" *Journal of Immunology*, Dec. 2013, pp. 17-23 8 pages.

Nakayama-Imaohji, H. et al. "Identification of the site-specific DNA invertase responsible for the phase variation of SusC/SusD family outer membrane proteins in Bacteroides fragilis" J. Bacterial.; 2009; vol. 191; No. 19; pp. 6003-6011.

Natori et al., Agelasphins, novel antitumor and immunostimulatory cerebrosides from the marine sponge Agelas mauritianus. Tetrahedron. 1994;50(9):2771-2784.

NCBI Sequence View "Toxin" [*Salmonella typhimurium* LT2], Retrieved Aug. 16, 2007 from http://www.ncbi.nim.nih.oov/entrez/viewer.fcoi?db=protein&id= 17233414, pp. 1-2.

Neurath et al., "TNBS-colilis", Int Rev Immunol., 2000, pp. 51-62, 19(1).

Nielsen et al., Applications of peptide nucleic acids. Curr Opin Biotechnol. Feb. 1999;10(1):71-5. Review.

Niess et al., "Commensal gut flora drives the expansion of proinflammatory CD4 T cells in the colonic lamina propria under normal and inflammatory conditions", J Immunol., Jan. 1, 2008, pp. 559-568, vol. 180, Issue 1.

No Author Listed, Acute Respiratory Disease Syndrome: What is acute respiratory disease syndrome? American Lung Association. 3 pages. http://www.lungusa.org/site/apps/nlnet/content3.aspz?c=dvLUK900E&b=2058817&content. Sep. 24, 2008.

No Author Listed, Excerpts from Immunobiology, in ed.. "Chapter 9. pp. 335-361; Chapter 1. pp. 2-9; Chapter 15. pp. 622-631" 2008.

No Author Listed, Lupus study. Meet A Lupus Researcher, www.lupusstudy.org/updates.php. Nov. 2005;1-2.

No Author Listed, Polyethylene Glycols (PEGs). Accessed Mar. 7, 2005. 1 page. http://www.mindfully.org/Plastic/Polymers/Polyethylene-Glycols-PEGs.htm.

No Author Listed, The Merck Index. Eleventh Edition 1989:734-735.

No Author Listed, VAXA, Systemic lupus erythematosus (SLE), damaging and unpredictable. http://www.vaxa.com/arthritis-systemic-lupus-erythematosus.cfm. 1 page. Accessed Apr. 3, 2008.

Non-Final Office Action for U.S. Appl. No. 12/267,602, filed Nov. 9, 2008 on behalf of Sarkis K. Mazmanian et al, dated Jul. 15, 2011. 12 pages.

Non-Final Office Action for U.S. Appl. No. 12/766,787, filed Apr. 23, 2010 on behalf of June L. Round et al, dated Jan. 20, 2015. 18 pages.

Non-Final Office Action for U.S. Appl. No. 12/766,787, filed Apr. 23, 2010 on behalf of June L. Round et al, dated May 8, 2012. 9 pages.

Non-Final Office Action for U.S. Appl. No. 12/766,787, filed Apr. 23, 2010 on behalf of June L. Round et al, dated Sep. 30, 2013. 19 pages.

Non-Final Office Action for U.S. Appl. No. 12/831,131, filed Jul. 6, 2010 on behalf of June L. Round et al, dated Aug. 26, 2014. 20 pages.

Non-Final Office Action for U.S. Appl. No. 12/831,131, filed Jul. 6, 2010 on behalf of June L. Round et al, dated Nov. 15, 2012. 22 pages.

Non-Final Office Action for U.S. Appl. No. 13/082,183, filed Apr. 7, 2011 on behalf of Yue Shen et al, dated Aug. 13, 2013. 7 pages.

Non-Final Office Action for U.S. Appl. No. 13/082,183, filed Apr. 7, 2011 on behalf of Yue Shen et al, dated Jan. 20, 2015. 7 pages.

Non-Final Office Action for U.S. Appl. No. 13/112,725, filed May 20, 2011 on behalf of June L. Round, dated Mar. 18, 2016. 11 pages.

Non-Final Office Action for U.S. Appl. No. 13/112,725, filed May 20, 2011 on behalf of June L. Round, dated May 8, 2014. 12 pages.

(56) References Cited

OTHER PUBLICATIONS

Non-Final Office Action for U.S. Appl. No. 13/360,702, filed Jan. 28, 2012 on behalf of Sarkis K. Mazmanian et al, dated Mar. 11, 2015. 13 pages.
Non-Final Office Action for U.S. Appl. No. 13/360,702, filed Jan. 28, 2012 on behalf of Sarkis K. Mazmanian et al, dated Mar. 18, 2013. 13 pages.
Non-Final Office Action for U.S. Appl. No. 13/464,876, filed May 4, 2012 on behalf of Sarkis K. Mazmanian et al, dated Jul. 9, 2013. 16 pages.
Non-Final Office Action for U.S. Appl. No. 13/573,695, filed Oct. 3, 2012 on behalf of Sarkis K. Mazmanian et al, dated Aug. 28, 2013.11 pages.
Non-Final Office Action for U.S. Appl. No. 14/015,769, filed Aug. 30, 2013 on behalf of Sarkis K. Mazmanian et al, dated Dec. 31, 2014. 7 pages.
Non-Final Office Action dated Aug. 9, 2017 in U.S. Appl. No. 14/264,607.
Non-Final Office Action dated Jan. 18, 2019 in U.S. Appl. No. 14/264,607.
Non-Final Office Action dated Mar. 16, 2017 in U.S. Appl. No. 14/631,760.
Non-Final Office Action dated Mar. 22, 2017 in U.S. Appl. No. 14/660,827.
Non-Final Office Action dated Dec. 27, 2018 in U.S. Appl. No. 14/660,827.
Non-Final Office Action dated May 11, 2018 in U.S. Appl. No. 14/803,598.
Non-Final Office Action for U.S. Appl. No. 15/011,151, filed Jan. 29, 2016 on behalf of California Institute of Technology dated Aug. 30, 2017 20 pages.
Non-Final Office Action dated Sep. 28, 2018 in U.S. Appl. No. 15/179,810.
Non-Final Office Action dated Oct. 14, 2020 in U.S. Appl. No. 15/179,810.
Non-Final Office Action dated Mar. 5, 2019 in U.S. Appl. No. 15/706,604.
Non-Final Office Action dated Nov. 17, 2019 in U.S. Appl. No. 16,514,796.
Non-Final Office Action dated Aug. 7, 2020 in U.S. Appl. No. 16/151,793.
Non-Final Office Action dated Sep. 1, 2020 in U.S. Appl. No. 16/562,358.
Norman; "Thyroiditis-Inflammation of the thyroid gland"; Endocrineweb 2009; www.endocrineweb.com/throiditis.html, 1-4. Downloaded Jul. 28, 2009.
Notice of Allowance for U.S. Appl. No. 13/573,695, filed Oct. 3, 2012 on behalf of Sarkis K. Mazmanian et al, dated Feb. 13, 2015. 9 pages.
Notice of Allowance for U.S. Appl. No. 13/573,695, dated May 15, 2015, 2 pages.
Notice of Allowance dated May 1, 2020 in U.S. Appl. No. 16/514,796.
Notice of Allowance dated Jul. 7, 2018 in European Patent Application No. 11766746.9.
Notice of Allowance dated Sep. 16, 2016 in Japanese Patent Application No. 2013-503958.
Notice of Allowance dated Jan. 9, 2018 in Japanese Patent Application No. 2016-126806.
Notice of Allowance dated Feb. 10, 2020 in Japanese Patent Application No. 2018-020819.
Notice of Reasons for Refusal dated Apr. 25, 2017 in Japanese Patent Application No. 2016-126806.
Notice of Reasons for Refusal dated Dec. 14, 2018 in Japanese Patent Application No. 2018-020819.
Notice of Reasons for Refusal dated Oct. 10, 2019 in Japanese Patent Application No. 2018-020819.
Notice of Reasons for Refusal dated Mar. 23, 2015 in Japanese Patent Application No. 2013-503958.
Notice of Reasons for Refusal dated Dec. 28, 2017 in Japanese Patent Application No. 2016-513092.
Notice of Reasons for Refusal dated Mar. 18, 2020 in Japanese Patent Application No. 2019-061261.
Notice of Reasons For Rejection for JP 2010-533311 dated May 14, 2013 in the name of California Institute of Technology. (English Translation).
Notification of Reason for Refusal for Japanese Patent Application No. 2013-511406, dated Apr. 12, 2016. 7 pages (Japanese original + English translation).
Notification of Reasons for Refusal for Japanese Patent Application No. 2013-511406, dated May 12, 2015. 6 pages (Japanese original+ English translation).
Noverr MC, et al. (2004) Does the microbiota regulate immune responses outside the gut? Trends Microbiol 12: 562-568.
Nylander A, et al. (2012) "Multiple sclerosis". The Journal of Clinical Investigation; vol. 122; DO. 1180-1188.
Ochoa-Reparaz J, et al. (2009) Role of gut commensal microflora in the development of experimental autoimmune encephalomyelitis. J Immunol 183: 6041-6050.
Ochoa-Reparaz J, et al. (2010) A polysaccharide from the human commensal Bacteroides fragilis protects against CNS demyelinating disease. Mucosal Immunol 3: 487-495.
Ochoa-Reparaz J, et al. (2010) Central nervous system demyelinating disease protection by the human commensal Bacteroides fragilis depends on polysaccharide A expression. J Immunol 185: 4101-4108.
Ochoa-Reparaz, J. et al. "The role of subcellular fractions of commensal Bacteroides fragilis in the control of experimental autoimmune encephalomyelitis" Multiple Sclerosis; Sep. 2009; vol. 15; (Abstract Only).
O'Connor et al., Translational mini-review series on Th17 cells: CD4 T helper cells: functional plasticity and differential sensitivity to regulatory T cell-mediated regulation. Clin Exp Immunol. Feb. 2010;159(2):137-47. doi: 10.1111/j.1365-2249.2009.04040.x. Epub Nov. 11, 2009.
Oda et al., A comprehensive map of the toll-like receptor signaling network. Mol Syst Biol. 2006:2:2006.0015. Epub Apr. 18, 2006.
Office Action for Japanese patent application No. JP2015-116494, dated Jul. 12, 2016. 8 pages (Japanese original + English translation).
O'Garra et al., "IL-10-producing and naturally occurring CD4+ Tregs: limiting collateral damage", J Clin Invest, Nov. 15, 2004, pp. 1372-1378, 114(10), National Center for Biotechnology Information, Bethesda MD.
Oh et al., CD4 T-helper cells engineered to produce IL-10 prevent allergen-induced airway hyperreactivity and inflammation. J Allergy Clin Immunol. Sep. 2002;110(3):460-8.
O'Hara et al., "The gut flora as a forgotten organ", EMBO, Jul. 1, 2006, pp. 688-693,vol. 7, Issue 7, EMBO, Heidelberg, Germany.
Ohno et al., Comparison of the immunopharmacological activities of triple and single-helical schizophyllan in mice. Biol Pharm Bull. Sep. 1995;18(9):1242-7.
Ohno et al., Enhancement of LPS triggered TNF-alpha (tumor necrosis factor-alpha) production by (1 ->3)-beta-D-glucans in mice. Biol Pharm Bull. Jan. 1995;18(1):126-33.
Onderdonk et al., The capsular polysaccharide of Bacteroides fragilis as a virulence factor: comparison of the pathogenic potential of encapsulated and unencapsulated strains. J Infect Dis. Jul. 1977;136(1):82-9.
Onderdonk, A. et al., Evidence for T Cell-dependent Immunity to Bacteroides fragilis in an Intraabdominal Abscess Model; J. Clin Investi. 69:9-16 (1982).
Ostman et al., "Impaired regulatory T cell function in germ-free mice", European Journal of Immunology, Sep. 2006 , pp. 233-246, vol. 36, Issue 9.
Ozenci et al., Multiple sclerosis: levels of interleukin-10-secreting blood mononuclear cells are low in untreated patients but augmented during interferon-beta-1 b treatment. Scand J Immunol. May 1999;49(5):554-61.
Palmer et al., "Development of the Human Infant Intestinal Microbiola", PLoS Bioi., Jun. 26, 2007, pp. 1556-1573. vol. 5, Issue 7, e177, PLOS, San Francisco, CA.

(56) References Cited

OTHER PUBLICATIONS

Palmer MT, et al. (2011) Lineage-specific effects of 1,25-dihydroxyvitamin D(3) on the development of effector CD4 T cells. The Journal of biological chemistry 286: 997-1004.
Pamer, "Immune responses to commensal and environmental microbes", Nat Immunol., Oct. 19, 2007, pp. 1173-1178, 8.
Pantosti et al., Bacteroides fragilis strains express multiple capsular polysaccharides. J Clin Microbial. Jul. 1993;31(7):1850-5.
Paoletti et al., Effects of chain length on the immunogenicity in rabbits of group B *Streptococcus* type 111 oligosaccharide-tetanus toxoid conjugates. J Clin Investi. Jan. 1992;89(1):203-9.
Paoletti et al., Neonatal Mouse Protection against Infection with Multiple Group B Streptococcal (GBS) Serotypes by Maternal Immunization with a Tetravalent GBS Polysaccharide-Tetanus Toxoid Conjugate Vaccine, Infection and Immunity, 62:3236-3243, 1994.
Park et al., Interleukin-2 and soluble interleukin-2 receptor in bronchoalveolar lavage fluid from patients with bronchial asthma. Chest. Aug. 1994;106(2):400-6.
Patrick et al. "Mutational analysis of genes implicated in LPS and capsular polysaccharide biosynthesis in the opportunistic pathogen Bacteroides fragilis" Microbiology. Apr. 2009;155(Pt 4):1039-49.
Pavliak et al., Structural elucidation of the capsular polysaccharide of Bacteroides fragilis strain 23745MI. Carbohydr Res. Oct. 2, 1995;275(2):333-41.
PCT International Search Report and Written Opinion for International Patent Application No. PCT/US2012/023050, dated May 21, 2012. 7 pages.
PCT International Search Report and Written Opinion for PCT Application No. PCT/US2014/037392 filed May 8, 2014 on behalf of California Institute of Technology, dated Sep. 19, 2014. 28 pages.
PCT Search Report for PCT/US2008/082928 in the name of California Institute of Technology filed on Nov. 9, 2008.
PCT Written Opinion dated Jun. 30, 2009 for PCT/US2008/082928 filed on Nov. 9, 2008 in the name of California Institute of Technology.
PCT International Search Report for PCT/US2010/032300 filed Apr. 23, 2010 on behalf of California Institute of Technology et al, dated Jan. 31, 2011. 5 pages.
PCT Written Opinion for PCT/US2010/032300 filed Apr. 23, 2010 on behalf of California Institute of Technology et al, dated Jan. 31, 2011. 5 pages.
Pedersen LB, et al. (2007) 1,25-dihydroxyvitamin D3 reverses experimental autoimmune encephalomyelitis by inhibiting chemokine synthesis and monocyte trafficking. J Neurosci Res 85: 2480-2490.
Perumal et al., Protective effect of interleukin-2 on experimental intra-abdominal abscess development due to Bacteriodes Fragilis. Clinical Research. 1990;38(2):550A.
Pierrot-Deseilligny C, et al. Is hypovitaminosis Done of the environmental risk factors for multiple sclerosis? Brain; 2010; 133:1869-1888.
Pillay J. et al., "Immune suppression by neutrophils and granulocytic myeloid-derived suppressor cells: similarities and differences" Cellular and Molecular Life Sciences, Feb. 2013, pp. 3813-3827 15 pages.
Poonawalla et al., "Urticaria—A Review", Am J Clin Dermalol., 2009, pp. 9-21, vol. 10, No. 1, Springer, Berlin, Germany.
Popivanova et al., "Blocking TNF-a in mice reduces colorectal carcinogenesis associated with chronic colitis," J. Clin. Invest., vol. 118, 560-570 (2008).
Popovic et al., Inhibition of autoimmune encephalomyelitis by a tetracycline. Ann Neural. Feb. 2002;51(2):215-23.
Power C, et al. (2010) The human microbiome in multiple sclerosis: pathogenic or protective constituents? The Canadian journal of neurological sciences Le journal canadien des sciences neurologiques 37 Suppl 2: S24-33.
Powrie et al., "Immunology. Regulating the regulators", Science, Feb. 14, 2003, pp. 1030-1031, 299(5609), AAAS, Washington, DC.
Poxton et al., Mucosa-associated bacterial flora of the human colon. J Med Microbial. Jan. 1997; 46(1):85-91.

Pragani & Seeberger, "Total Synthesis of the Bacteroides fragilis Zwitterionic Polysaccharide A 1 Repeating Unit," JACS 2011, 133, 102-107.
Prieto et al., A new ganglioside in human meconium detected by antiserum against the human milk sialyloligosaccharide, LS-tetrasaccharide b, Archives of Biochemistry and Biophysics, 241:281-289, 1985.
Prucha et al., "Presence of Hypogammaglobulinemia—A Risk Factor of Mortality in Patients with Severe Sepsis, Septic Shock, and SIRS," Prague Medical Report 2013, 114(4), 246-257.
Rabe et al., Pharmacological treatment of asthma today. Eur Respir J Suppl. 2001; 34:34s-40s.
Raetz et al., Lipopolysaccharide endotoxins. Annu Rev Biochem. 2002,71 :635-700. Epub Nov. 9, 2001.
Raghuwanshi, A et al. "Vitamin D and Multiple Sclerosis" Journal of Cellular Biochemistry; 2008; vol. 105; pp. 338-343.
Rakoff-Nahoum et al., "Recognition of commensal microflora by loll-like receptors is required for Intestinal homeostasis", Cell, Jul. 23, 2004, pp. 229-241, vol. 118, Issue 2.
Raman et al. Vitamin D and gastrointestinal diseases: inflammatory bowel disease and colorectal cancer in Ther Adv. Gastroenterology, Jan. 10, 2011 (Jan. 10, 2011) vol. 4, pp. 49-62.
Ranua et al., Serum IgA, IgG, and IgM concentrations in patients with epilepsy and matched controls: a cohort-based cross-sectional study. Epilepsy Behav. Mar. 2005;6(2):191-5.
Reid, R.R., et al., "Endotoxin shock in antibody-deficient mice: unraveling the role of natural antibody and complement in the clearance of lipopolysaccharide," *Journal of immunology*, 1997. 159(2): p. 970-5. Abstract Only.
Rescigno, M. et al., "Dendritic cells express tight junction proteins and penetrate gut epithelial monolayers to sample bacteria" Nat Immunol 2, 361 (2001).
Restriction Requirement for U.S. Appl. No. 12/766,787, filed Apr. 23, 2010 on behalf of June L. Round et al, dated Mar. 15, 2012. 9 pages.
Restriction Requirement for U.S. Appl. No. 13/082,183, filed Apr. 7, 2011 on behalf of Yue Shen et al, dated May 31, 2013. 7 pages.
Restriction Requirement for U.S. Appl. No. 13/112,725, filed May 20, 2011 on behalf of June L. Round, dated Mar. 18, 2013. 7 pages.
Restriction Requirement for U.S. Appl. No. 13/360,702, filed Jan. 28, 2012 on behalf of Sarkis K. Mazmanian et al, dated Feb. 1, 2013. 6 pages.
Restriction Requirement for U.S. Appl. No. 13/573,695, filed Oct. 3, 2012 on behalf of Sarkis K. Mazmanian et al, dated May 23, 2013. 9 pages.
Restriction Requirement for U.S. Appl. No. 14/755,327, filed Jun. 30, 2015 on behalf of Sarkis K. Mazmanian et al, dated Aug. 11, 2016. 8 pages.
Restriction Requirement issued by the USPTO for U.S. Appl. No. 12/267,602 dated Mar. 17, 2011.
Restriction Requirement issued in U.S. Appl. No. 13/464,876, filed May 4, 2012 in the name of Sarkis Mazmanian, dated Feb. 20, 2013.
Restriction Requirement dated Jul. 11, 2012 for U.S. Appl. No. 12/831,131, filed Jul. 6, 2010 in the name of June L. Round.
Restriction Requirement dated Aug. 18, 2014 in U.S. Appl. No. 14/015,769.
Restriction Requirement dated Jan. 26, 2015 in U.S. Appl. No. 14/274,607.
Restriction Requirement for U.S. Appl. No. 14/803,598, filed Jul. 20, 2015 on behalf of California Institute of Technology dated Feb. 14, 2018. 7 pages.
Restriction Requirement for U.S. Appl. No. 15/499,805, filed Apr. 27, 2017 on behalf of California Institute of Technology dated May 3, 2019 7 pages.
Restriction Requirement dated May 4, 2018 in U.S. Appl. No. 15/178,810.
Riesenfeld et al., Biosynthesis of heparin. Assay and properties of the microsomal N-acetyl-D-glucosaminyl N-deacetylase. J Biol Chem. Feb. 10, 1980;255(3):922-8.
Rodgers et al., "Prescribing an antibiotic? Pair it with probiotics", The Journal of Family Practice, Mar. 2013, pp. 148-150, vol. 62, No. 3.

(56) References Cited

OTHER PUBLICATIONS

Roncarolo et al., Type IT regulatory cells. Immunol Rev. Aug. 2001; 182:68-79. Review.
Round JL, et al. (2009) Coordination of tolerogenic immune responses by the commensal microbiota. J Autoimmun.
Round JL, et al. (2011) The Toll-like receptor 2 pathway establishes colonization by a commensal of the human microbiota. Science 332: 974-977.
Rubtsov et al., "Regulatory T cell-derived interleukin-10 limits inflammation at environmental interfaces", Immunity, Apr. 11, 2008, pp. 546-558, vol. 28, Issue 4.
Ruiz-Perez et al., "Modulation of surgical fibrosis by microbial zwitterionic polysaccharides", PNAS, Nov. 15, 2005, pp. 16753-16758, vol. 102, No. 46.
Runia TF, et al. (2012) Lower serum vitamin D levels are associated with a higher relapse risk in multiple sclerosis. Neurology 79: 261-266.
Rutgeerts et al., "Infliximab for induction and maintenance therapy for ulcerative colitis", N Engl J Med., Dec. 8, 2005, pp. 2462-2476, 353.
Rypens et al., Percutaneous drainage of abdominal abscesses in pediatric Crohn's disease. AJR Am J Roentgenol. Feb. 2007;188(2):579-85.
Sakaguchi S, et al. (2008) Regulatory T cells and immune tolerance. Cell 133: 775-787.
Sakaguchi, S. et al. (2006) Foxp3+ CD25+ CD4+ natural regulatory T cells in dominant self-tolerance and autoimmune disease. Immunol. Rev. 212, pp. 8-27.
Salyers et al., Conjugative transposons: an unusual and diverse set of integrated gene transfer elements. Microbial Rev. Dec. 1995;59(4):579-90. Review.
Sartor., "Mechanisms of disease: pathogenesis of Crohn's disease and ulcerative colitis", Nat Clin Pract Gastroenterol Hepatol., Jul. 1, 2006, pp. 390-407, 3.
Sawada et al., "Leukocytapheresis in Ulcerative Colitis: Results of a Multicenter Double-Blind Prospective Case-Control Study with Sham Apheresis as Placebo Treatment", American Journal of Gastroenterology, Jun. 1, 2005, pp. 1362-1369, vol. 100.
Scheinin et al., "Validation of theinterleukin-10 knockout mouse model of colitis: antitumour necrosis factor antibodies suppress the progression of colitis", Clin Exp Immunol., Jul. 2003, pp. 38-43, vol. 133, Issue 1.
Schembri MA et al. Orientation-dependent enhancement by H-NS of the activity of the type 1 fimbrial phase switch promoter in *Escherichia coli*. (1998) Mol Gen Genet 259:336-44.
Schlegel et al., A synthetic random basic copolymer with promiscuous binding to class 11 major histocompatibility complex molecules inhibits T-cell proliferative responses to major and minor histocompatibility antigens in vitro and confers the capacity to prevent murine graft-versus-host disease in vivo. Proc Natl Acad Sci USA. May 14, 1996;93(10):5061-6. Erratum in: Proc Natl Acad Sci USA Aug. 6, 1996;93(16):8796.
Schneider et al., De nova design of molecular architectures by evolutionary assembly of drug derived building blocks. J Comput Aided Mol Des. Jul. 2000;14(5):487-94.
Segal et al., Severe insulin resistance secondary to insulin antibodies: successful treatment with the immunosuppressant MMF. Pediatr Diabetes. Jun. 2008;9(3 Pt 1):250-4.
Sellin et al., Conformational analysis of a toxic peptide from Trimeresurus wagleri which blocks the nicotinic acetylcholine receptor. Biophys J. Jan. 1996;70(1):3-13.
Sellon et al. "Resident enteric bacteria are necessary for development of spontaneous colitis and immune system activation in interleukin-10-deficient mice", Infect Immun., Nov. 1998, pp. 5224-5231, vol. 66 No. 11.
"Sepsis" from National Institute of General Medical Sciences, dated Jan. 2018 (3 pages).
Shaklee et al., Hydrazinolysis of heparin and other glycosaminoglycans. Biochem. J. (1984); 217: 187-197.

Shapiro et al., Cellular control of abscess formation: role of T cells in the regulation of abscesses formed in response to Bacteroides fragilis. J Immunol. Jul. 1, 1986;137(1):341-6.
Shapiro et al., Cellular immunity to Bacteroides fragilis capsular polysaccharide. J Exp Med. Apr. 1, 1982;155(4):1188-97.
Sharpe et al., The B7-CD28 superfamily. Nat Rev Immunol. Feb. 2002;2(2): 116-26. Review.
Shevach, CD4+ CD25+ suppressor T cells: more questions than answers. Nat Rev Immunol. Jun. 2002;2(6):389-400. Review.
Sigmundsdottir H, et al. (2007) DCs metabolize sunlight-induced vitamin D3 to 'program' T cell attraction to the epidermal chemokine CCL27. Nature immunology 8: 285-293.
Silvestro et al. "Effects of subinhibitory concentrations of clindamycin on the morphological, biochemical and genetic characteristics of Bacteroides fragilis" FEMS Microbiol. Lett. 2006; vol. 257; No. 2; pp. 189-194.
Simmons et al., Synthesis and membrane permeability of PNA-peptide conjugates. Bioorg Med Chem Lett. 1997;7(23):3001-6.
Slack, E., et al. (2009). Innate and adaptive immunity cooperate flexibly to maintain host-microbiota mutualism. Science 325, 617-620.
Smith et al. "Use of axenic animals in studying the adaptation of mammals to their commensal intestinal microbiota", Semin Immunol., Apr. 2007, pp. 59-69, vol. 19, Issue 2, Elsevier, Amsterdam, Netherlands.
Smith SG et al. Functional analysis of the FimE integrase of *Escherichia coli* K-12: isolation of mutant derivatives with altered DNA inversion preferences. (1999) Mol Microbiol 34:965-79.
Smits, H.H. et al. "Selective probiotic bacteria induce IL-10-producing regulatory T cells in vitro by modulating dendritic cell function through dendritic cell-specific intercellular adhesion molecule 3-grabbing nonintegrin" J Allergy Clin Immunol. (2005) pp. 1260-1267.
Solomon AJ, et al. "Multiple Sclerosis and Vitamin D: A Review and Recommendations" Curr. Neurol Neurosci Rep.; 2010; vol. 10; pp. 389-396.
Spach KM, et al. (2005) Vitamin D3 confers protection from autoimmune encephalomyelitis only in female mice. J Immunol 175: 4119-4126.
Spach KM, et al. (2004) Gene expression analysis suggests that 1,25-dihydroxyvitamin D3 reverses experimental autoimmune encephalomyelitis by stimulating inflammatory cell apoptosis. Physiol Genomics 18: 141-151.
Sprinz, H. et al. (1961) The response of the germfree guinea pig to oral bacterial challenge with *Escherichia coli* and Shigella flexneri. Am J. Pathol. 39, 681-695.
Stefanelli et al., "New insights into inflammatory bowel disease pathophysiology: paving the way for novel therapeutic targets", Current Drug Targets, May 2008, pp. 413-418, vol. 9, No. 5.
Stein et al., Thymus-independent and thymus-dependent responses to polysaccharide antigens. J Infect Dis. Jun. 1992;165 Suppl I:S49-52. Review.
Stenvinkel et al., "IL-10, IL-6, and TNF-a: central factors in the altered cytokine network of uremia-the good, the bad, and the ugly", Kidney International, Apr. 2005, pp. 1216-1233, vol. 67, Issue 4, Elsevier, New York City, NY.
Stephen et al. "Effect of 87-2 and CD40 Signals from Activated Antigen-Presenting Cells on the Ability of Zwitterionic Polysaccharides to Induce T-Cell Stimulation" 2005; Inf. Immun. Vol. 73; pp. 2184-2189.
Stewart N, et al. (2012) Interferon-beta and serum 25-hydroxyvitamin D interact to modulate relapse risk in MS. Neurology 79:254-260.
Stockinger et al., "Differentiation and function of Th17 T cells", Current Opinion in Immunology, Jun. 2007, pp. 281-286, vol. 19, Issue 3.
Strachan et al. "Hay fever, hygiene, and household size", BMJ, Nov. 18, 1989, pp. 1259-1260, 299 (6710).
Strauch et al., "Influence of intestinal bacteria on induction of regulatory T cells: lessons from a transfer model of colitis", Gut, Jun. 29, 2005, pp. 1546-1552, vol. 54, Issue 11.
Strober, "The multifaceted influence of the mucosal microflora on mucosal dendritic cell responses", Immunity, Sep. 18, 2009, pp. 377-388, vol. 31, Issue 3.

(56) References Cited

OTHER PUBLICATIONS

Stromnes IM, et al. (2006) Active induction of experimental allergic encephalomyelitis. Nat Protoc 1: 1810-1819.
Stromnes et al., Passive induction of experimental allergic encephalomyelitis. Nat Protoc. 2006; 1(4): 1952-60.
Stumhofer et al., "Interleukins 27 and 6 induce STAT3-mediated T cell production of interleukin 10", Nat Immunol, Nov. 11, 2007, pp. 1363-1371, 8.
Supplementary European Search Report for EP Application No. EP2217250, dated Dec. 8, 2010, 2 pages.
Suri-Payer et al., CD4+CD25+ T cells inhibit both the induction and effector function of autoreactive T cells and represent a unique lineage of immunoregulatory cells. J Immunol. Feb. 1, 1998; 160(3): 1212-8.
Sutmeuller et al., "Toll-like receptor 2 controls expansion and function of regulatory T cells", J. Clin. Invest., Feb. 1, 2006, pp. 485-494, vol. 116, Issue 2.
Szu et al., Relation between structure and immunologic properties of the Vi capsular polysaccharide. Infect Immun. Dec. 1991;59(12):4555-61.
Taconic, "Swiss Webster Outbred," Taconic Biosciences 2019, in 9 pages.
Takatori, N. "Probiotics, beneficial bacteria, and inflammatory bowel disease; What do we actually know?" Nutritional Bytes, 2009, vol. 13, pp. 1-6.
Tanaka, H et al. "Human monocyte-derived dendritic cells induce naive T cell differentiation into T helper cell type 2 (Th2) of Th1/Th2 effectors: role of stimulator/responder ratio" Journal of Experimental Medicine; vol. 192; No. 3; Aug. 7, 2000; pp. 405-411.
Tang et al., Th type 1 -stimulating activity of lung macrophages inhibits Th2-mediated allergic airway inflammation by an IFN-gamma-dependent mechanism. J Immunol. Feb. 1, 2001; 166(3): 1471-81.
Tang, et al. "In-vitro-expanded Antigen-specific Regulatory T cells suppress autoimmune diabetes" J. Exp. Med. Vol. 199; No. 11; Jun. 7, 2004; pp. 1455-1465.
Taurog et al., "The germfree state prevents development of gut and joint inflammatory disease in HLA-B27 transgenic rats", J Exp Med., Dec. 1, 1994, pp. 2359-2364, 180 (6).
Taylor et al., Stoichiometric depolymerization of polyuronides and glycosaminoglycuronans to monosaccharides following reduction of their carbodiimide-activated carboxyl groups. Biochemistry. Apr. 11, 1972;11 (8): 1383-8.
Teitelbaum et al., Immunomodulation of experimental autoimmune encephalomyelitis by oral administration of copolymer 1. Proc Natl Acad Sci USA. Mar. 30, 1999;96(7):3842-7.
Teitelbaum et al., Specific inhibition of the T-cell response to myelin basic protein by the synthetic copolymer Cop 1. Proc Natl Acad Sci USA. Dec. 1988;85(24):9724-8.
Teitelbaum et al., Synthetic copolymer 1 inhibits human T-cell lines specific for myelin basic protein. Proc Natl Acad Sci USA. Jan. 1, 1992 ;89(1):137-41.
Teitelbaum et al., Unprimed spleen cell populations recognize macrophage-bound antigen with opposite net electric charge. Proc Natl Acad Sci USA. Apr. 1977;74(4):1693-6.
Telesford, et al., "A commensal symbiotic factor derived from Bacteroides fragilis promotes human CD39+Foxp3+ T cells and Treg function," Gut Microbes, vol. 6: 234-242. Published online Jul. 31, 2015. 10 Pages.
The Language of Prevention, National Public Health Partnership, 2006, 9 pages.
Thomas et al., Randomised controlled trial of short bursts of a potent topical corticosteroid versus prolonged use of a mild preparation for children with mild or moderate atopic eczema. BMJ. 2002;324(7640):1-7.
Tong et al., "Mouse Models of Colorectal Cancer," Chin. J. Cancer, vol. 30, 450-62 (2011).

Torisu M., et al., "Significant Prolongation of Disease-Free Period Gained by Oral Polysaccharide K (PSK) Administration after Curative Surgical Operation of Colorectal Cancer," Cancer Immunology, Immunotherapy, vol. 31 (5), Sep. 1, 1990, 8 pages, XP055323922.
Tournoy et al., Endogenous interleukin-10 suppresses allergen-induced airway inflammation and nonspecific airway responsiveness. Clin Exp Allergy. Jun. 2000;30(6):775-83.
Toussirot, E., et al., Bacterial extract (OM-89) specific and non specific immunomodulation in rheumatoid arthritis patients, Autoimmunity 2006, 39: 299-306 Abstract Only.
Triantafillidis et al., "Colorectal Cancer and Inflammatory Bowel Disease: Epidemiology, Risk Factors, Mechanisms of Carcinogenesis and Prevention Strategies," Anticancer Res., vol. 29, 2727-37 (2009).
Troy, E. et al. "Beneficial effects of Bacteroides fragilis polysaccharides on the immune system." Front Biosci., Jan. 1, 2010, vol. 15; pp. 25-34.
Troy, E. et al., "Orientations of the Bacteroides fragilis capsular polysaccharide biosynthesis locus promoters during symbiosis and infection", Journal of Bacteriology, Nov. 2010, vol. 192, No. 21, pp. 5832-5836.
Turnbaugh et al., "An obesity-associated gut microbiome with increased capacity for energy harvest", Nature, Dec. 21, 2006, pp. 1027-1031, 444(7122).
Turnbaugh et al., "The human microbiome project: exploring the microbial part of ourselves in a changing world", Nature, Oct. 18, 2007, pp. 804-810. Vol. 449, Issue 7164.
Tzianabos et al., "The Capsular Polysaccharide of Bacteroides fragilis Comprises Two Ionically Linked Polysaccharide," J. Biol. Chem., vol. 267, 18230-5 (1992).
Tzianabos et al. "Structural Characteristics of Polysaccharides that Induce Protection Against IntraAbdominal Abscess Formation" Infection and Immunity, Nov. 1, 1994, pp. 4881-4886, vol. 62, No. 11.
Tzianabos et al. "T-Cells Activated by Zwitterionic Molecules prevent abscesses induced by pathogenic bacteria" J. Biol. Chem. 2000; vol. 275; No. 10; pp. 6733-6740.
Tzianabos et al., Bacterial structure and functional relation to abscess formation. Infect Agents Dis. Oct. 1994;3(5):256-65. Review.
Tzianabos et al., Characteristics of bacterial polysaccharides that activate T cells. The International Carbohydrate Symposium XVII. Jul. 21, 1994. 1 page.
Tzianabos et al., Effect of surgical adhesion reduction devices on the propagation of experimental intra-abdominal infection. Arch Surg. Nov. 1999;134(11):1254-9.
Tzianabos et al., IL-2 mediates protection against abscess formation in an experimental model of sepsis. J Immunol.Jul. 15, 1999;163(2):893-7.
Tzianabos et al., Protection against Experimental Iniraahdominal Sepsis by Two Polysaccharide Immunomodulators. J Infect Dis. Jul. 1998;178(1):200-6.
Tzianabos et al., Structure-function relationships for polysaccharide-induced intra- abdominal abscesses. Infect Immun. Aug. 1994;62(8):3590-3.
Tzianabos et al., T Cell Activation by Zwitterionic polysaccharides and peptide mimetics prevents intrabdominal abscess formation. Abstracts of the 99th General Meeting of the American Society for Microbiology. Chicago, US: May 30-Jun. 3, 1999. Jun. 28, 1999; 1 page.
Tzianabos, A.O., Polysaccharide Immunomodulators as Therapeutic Agents: Structural Aspects and Biologic Function, Clin. Microbial. Rev. 13(4):523-533 (2000).
Tzianabos, AO et al., Polysaccharide-mediated protection against abscess formation in experimental intra-abdominal sepsis. J Clin. Investi. (1995) 96:2727-31.
Tzianabos, et al., Structural rationale for the modulation of abscess formation by *Staphylococcus aureus* capsular polysaccharides. Proc Natl Acad Sci USA. Jul. 31, 2001 98(16):9365-70. Epub Jul. 24, 2001.
Uronis et al., "Modulation of the Intestinal Microbiota Alters Colitis-Associated Colorectal Cancer Susceptibility," PLoS ONE, vol. 4, e6026 (2009).

(56) References Cited

OTHER PUBLICATIONS

Van Maren et al., "Toll-like receptor signalling on Tregs: to suppress or not to suppress?", Immunology, Aug. 2008, pp. 445-452, vol. 124, Issue 4.

Van Scott et al., IL-10 reduces Th2 cytokine production and eosinophilia but augments airway reactivity in allergic mice. Am J Physiol Lung Cell Mol Physiol. Apr. 2000;2/8(4):L667-74.

Vann et al., The structure of the capsular polysaccharide (K5 antigen) of urinary-tract-infective *Escherichia coli* 010:K5:H4. A polymer similar to desulfo-heparin. Eur J Biochem. May 15, 1981; 116(2):359-64.

Vázquez et al., "Therapeutic drug monitoring of vacomycin in severe sepsis and septic shock," International Journal of Clinical Pharmacology and Therapeutics 2008, 46, 140-145.

Veldhoen, M. et al. "TGF beta in the context of an inflammatory cytokine milieu supports de novo differentiation of IL-17-producing T cells." Immunity; vol. 24; pp. 179-189.

Velez et al., Type I *Streptococcus pneumoniae* carbohydrate utilizes a nitric oxide and MGC 11-dependent pathway for antigen presentation. Immunol. 2008; 127:73-82.

Verdu et al., Oral administration of antigens from intestinal flora anaerobic bacteria reduces the severity of experimental acute colitis in BALB/c mice. Clin Exp Immunol. Apr. 2000;120(1):46-50.

Videla et al., "Role of intestinal microflora in chronic inflammation and ulceration of the rat colon", Gut, 1994, pp. 1090-1097, vol. 35, Issue 8.

Vignali, DA et al. "How regulatory T cells work." Nat. Rev. Immunol.; 2008; vol. 8; pp. 523-532.

Vinderola et al., Effects of the oral administration of the exopolysaccharide produced by Lactobacillus kefiranofaciens on the gut mucosal immunity. Cytokine. Dec. 2006;36(5-6):254-60. Epub Mar. 23, 2007.

Viret et al., Molecular cloning and characterization of the genetic determinants that express the complete Shigella serotype D (Shigella sonnei) lipopolysaccharide in heterologous live attenuated vaccine strains. Mol Microbial. Jan. 1993;7(2):239-52.

Wagner et al., Use of reporter cells to study endogenous retinoid sources in embryonic tissues. Methods Enzymol. 1997;282:98-107.

Wang et al., "A bacterial carbohydrate links innate and adaptive responses through Toll-like receptor 2," J. Exp. Med., vol. 203, 2853-63 (2006).

Wang et al., Lipopolysaccharide: Biosynthetic pathway and structure modification. Prog Lipid Res. Apr. 2010;49(2):97-107. doi: 10.1016/j.plipres.2009.06.002. Epub Oct. 6, 2009.

Wang et al., Ozonolysis for selectively depolymerizing polysaccharidescontaining p-d-aldosidic linkages. Proc Natl Acad Sci USA. Jun. 9, 1998; 95(12): 6584-6589.

Wang et al., Structural basis of the abscess-modulating polysaccharide A2 from Bacteroides fragilis. Proc Natl Acad Sci USA. Dec. 5, 2000;97(25): 13478-83.

Wang et al., Structure characterization of an abscessogenic capsular polysaccharide from Bacteriodes fragilis by NMR spectroscopy. XIX International Conference of NMR in Biological Systems. Florence, Italy Aug. 20-25, 2000. Abstract.

Ward et al., The nucleotide sequence of the tnpA gene of Tn21, Nucleic Acids Research, vol. 15(4), 1987, 1799-1806.

Wehr et al., Anti-low-density lipoprotein antibodies in alcoholics without and with liver disease and in social drinkers. Alcohol & Alcoholism Jan.-Feb. 1997;32(1):43-9.

Weinacht et al. Phase variation of the capsular polysaccharides of Bacteroides fragilis is dictated by site-specific recombinases. 2002 General Meeting of the American Society for Microbiology, May 19-23, 2002. Abstract.

Wen, L. et al. "Innate immunity and intestinal microbiota in the development of Type 1 diabetes" Nature; 2008; vol. 455; pp. 1109-1113.

Wessels et al., Structural Determination and Immunochemical Characterization of the Type V Group B *Streptococcus* Capsular Polysaccharide, The Journal of Biological Chemistry, 266:6714-6719, 1991.

Wessels et al., Structure and immunochemistry of an oligosaccharide repeating unit of the capsular polysaccharide of Type 111 group B *Streptococcus*. A revised structure for the type 111 group B streptococcal polysaccharide antigen. J Biol Chem. Jun. 15, 1987;262(17):8262-7.

Wexler, Bacteroides: the good, the bad, and the nitty-gritty. Clin Microbial Rev. Oct. 2007;20(4):593-621.

Whitfield, Biosynthesis and assembly of capsular polysaccharides in *Escherichia coli*. Annu Rev Biochem. 2006;75:39-68.

Wiegandt et al., Carbohydrate Components of Extraneuronal Gangliosides from Bovine and Human Spleen, and Bovine Kidney, European Journal of Biochemistry, 15:287-292, 1970.

Wilier CJ, et al. (2003) Twin concordance and sibling recurrence rates in multiple sclerosis. Proc Natl Acad Sci USA 100: 12877-12882.

Wingate K. et al., "25-Hydroxyvitamin D Concentrations in Children with Crohn's Disease Supplemented with Either 2000 or 400 IU Daily for 6 Months: A Randomized Controlled Study" The Journal of Pediatrics, vol. 164, No. 4,Apr. 2014, pp. 860-865 6 pages.

Wirtz et al., Mouse models of inflammatory bowel disease. Adv Drug Deliv Rev. Sep. 30, 2007;59(11):1073-83. Eoub Aug. 16, 2007.

Woessner et al., Long-term antibiotic treatment with roxithromycin in patients with multiple sclerosis. Infection. Dec. 2006;34(6):342-4.

Wong et al., "Activation of Peripheral Th17 Lymphocytes in Patients with Asthma", Immunological Investigations, Sep. 19, 2009, pp. 652-664, vol. 38, Issue 7.

Woodruff, et al., Sudden-onset severe acute asthma: Clinical features and response to therapy, Academic Emergency Med. 1998, 5: 695-701.

Written Opinion for International Application PCT/US2016/037044 filed Jun. 10, 2016 on behalf of California Institute of Technology, dated Sep. 22, 2016. 8 pages.

Wu HJ, et al. (2010) Gut-residing segmented filamentous bacteria drive autoimmune arthritis via T helper 17 cells. Immunity 32: 815-827.

Wujek et al., A carbohydrate polymer that effectively prevents epidural fibrosis at laminectomy sites in the rat. Exp Neural. Nov. 1991;114(2):237-45.

Xavier, R. & Podolsky, D. K. Commensal flora: wolf in sheep's clothing. Gastroenterology 128, 1122-6 (2005).

Xie & Itzkowitz, "Cancer in inflammatory bowel disease," World J. Gastroenterol., vol. 14, 378-89 (2008).

Xu Jet al., A genomic view of the human-Bacteroides thetaiotaomicron symbiosis. Science. Mar. 28, 2003;299(5615):2074-6.

Yamakazi et al. "Dendritic cells are specialized accessory cells along with TGF-beta for the differentiation of Foxp3+ CD4+ regulatory T cells from peripheral Foxp3- precursors" Blood. 2007; 110: 4293-4302.

Yamazaki, T. et al. "CCR6 regulates the migration of inflammatory and regulatory T cells" J. Immunology; 2008; vol. 181; pp. 8391-8401.

Yang J. et al., "Targeting Th17 cells in autoimmune diseases" Cell Press, vol. 35, No. 10,Oct. 2014, pp. 493-500 8 pages.

Yokoyama et al., Adhesion behavior of rat lymphocytes to poly(ether)-poly(amino acid) block and graft copolymers. J Biomed Mater Res. Sep. 1986;20(7):867-78.

Yoshii, Cytotoxic effects of acrylates and methacrylates: relationships of monomer structures and cytotoxicity. J Biomed Mater Res. Dec. 15, 1997;37(4):517-24.

Young et al., "In vitro and in vivo characterization of Helicobacter hepaticus cytolethal distending toxin mutants", Infect Immun., May 2004, pp. 2521-2527, vol. 72 No. 5.

Zabad et al., The clinical response to minocycline in multiple sclerosis is accompanied by beneficial immune changes: a pilot study. Mult Scler. May 2007;13(4):517-26. Epub Feb. 9, 2007.

Zaleznik et al., A soluble suppressor T cell factor protects against experimental intraabdominal abscesses. J Clin Investi. Mar. 1985;75(3):1023-7.

(56) References Cited

OTHER PUBLICATIONS

Zaph, C., et al. (2008). Commensal-dependent expression of IL-25 regulates the IL-23-IL-17 axis in the intestine. J Exp Med 205, 2191-2198.

Zehnder D, et al. (1999) Expression of 25-hydroxyvitamin D3-1 alpha-hydroxylase in the human kidney. J Am Soc Nephrol 10: 2465-2473.

Zehnder D, et al. (2001) Extrarenal expression of 25-hydroxyvitamin d(3)-1 alpha-hydroxylase. J Clin Endocrinol Metab 86: 888-894.

Zhang et al., Degradation of Wood Polysaccharide Model Compounds During Ozone Treatment. Journal of Pulp and Paper Science. Jan. 1997;23(1):J23-J27.

Zhang X., et al., "Calcium, Vitamin D and Colorectal Cancer Chemoprevention," Bailliere's Best Practice and Research, Clinical Gastroenterology, vol. 25(4), Jan. 1, 2011, 10 pages.

Zhang et al., IL-10 is involved in the suppression of experimental autoimmune encephalomyelitis by CD25+CD4+ regulatory T cells. Int Immunol. Feb. 2004;16(2):249-56.

Zhao H et al. In vivo phase variation of MR/P fimbrial gene expression in Proteus mirabilis infecting the urinary tract. (1997) Mol Micro biol 23: 1009-19.

Zhou, L. et al. "TGF-beta-induced Foxp3 inhibits T(H)17 cell differentiation by antagonizing RORgammat function" Nature; 2008; vol. 453; pp. 236-240.

Zhu et al., Oral administration of type-11 collagen peptide 250-270 suppresses specific cellular and humoral immune response in collagen-induced arthritis. Clin Immunol. Jan. 2007; 122(1):75-84. Epub Oct. 11, 2006.

Zouali, M. et al., "Marginal Zone B-Cells, A Gatekeeper of Innate Immunity", Frontiers in Immunology, vol. 2, Article 63, 10 pages, (2011).

Non-Final Office Action dated Aug. 19, 2021 in U.S. Appl. No. 16/151,793.

Non-Final Office Action dated Aug. 23, 2021 in U.S. Appl. No. 15/179,810.

Notice of Allowance dated Aug. 20, 2021 in Japanese Patent Application No. 2020-006703.

Notice of Allowance dated Aug. 27, 2021 in Japanese Patent Application No. 2019-061261.

Notification of Reasons for Refusal dated Aug. 13, 2021 in Japanese Patent Application No. 2020-006706.

Applicant-Initiated Interview Summary dated Nov. 17, 2021 in U.S. Appl. No. 15/179,810.

Applicant-Initiated Interview Summary dated Nov. 24, 2021 in U.S. Appl. No. 16/562,358.

Final Office Action dated Oct. 4, 2021 in U.S. Appl. No. 16/562,358.

Non-Final Office Action dated Dec. 10, 2021 in U.S. Appl. No. 16/562,358.

Notice of Allowance dated Oct. 25, 2021 in Japanese Patent Application No. 2020-006706.

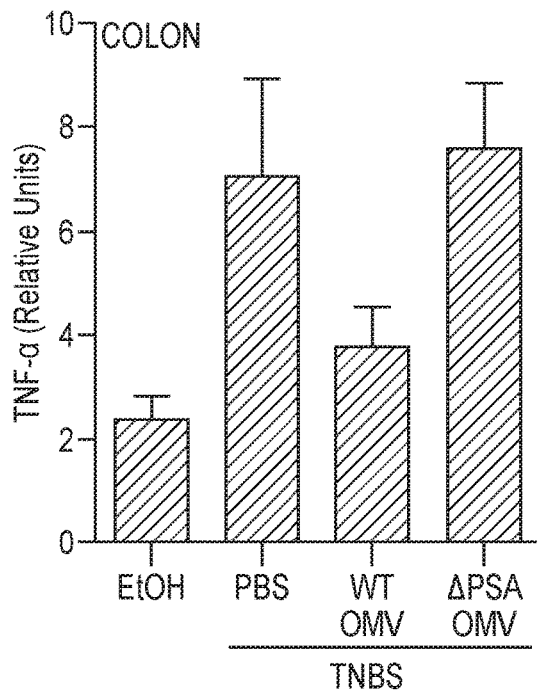
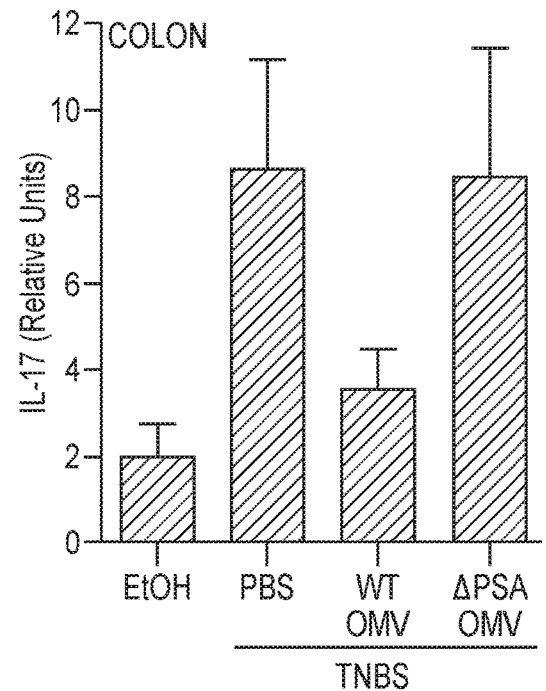
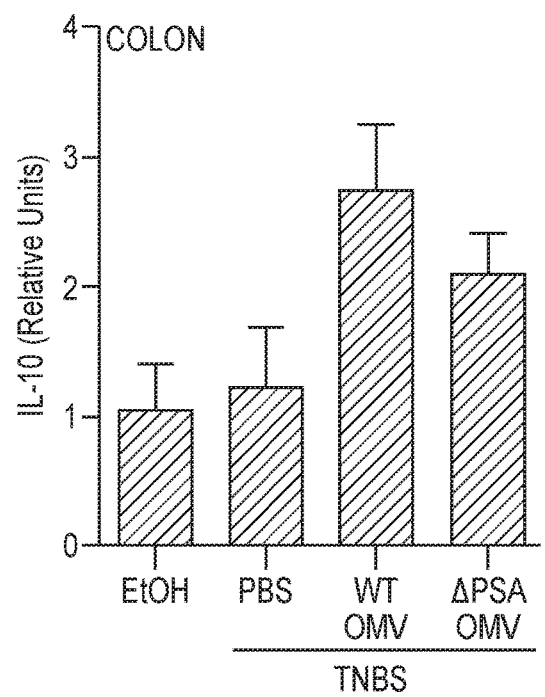
Figure 2E

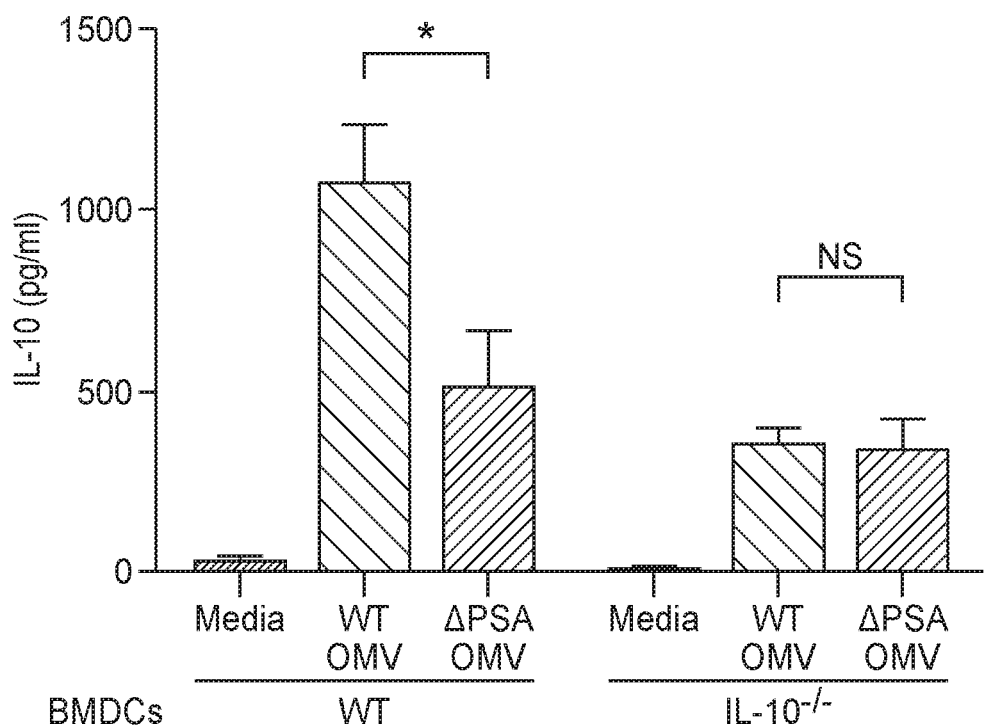
Figure 3D(i)
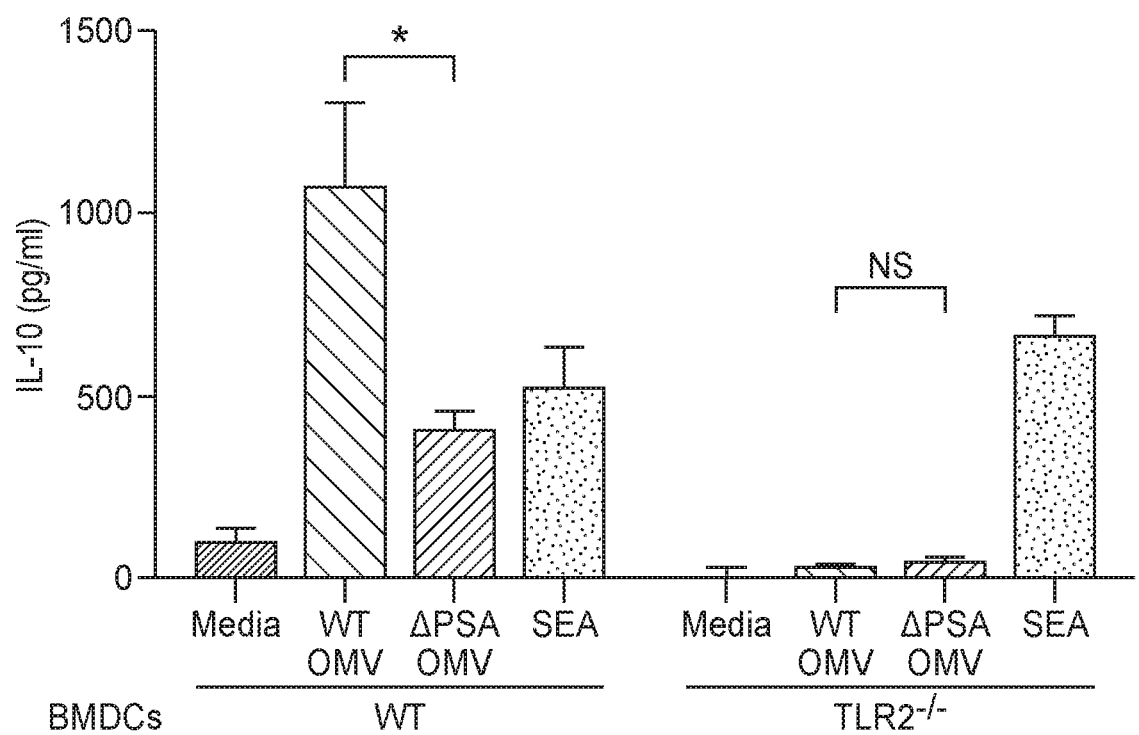
Figure 3D(ii)

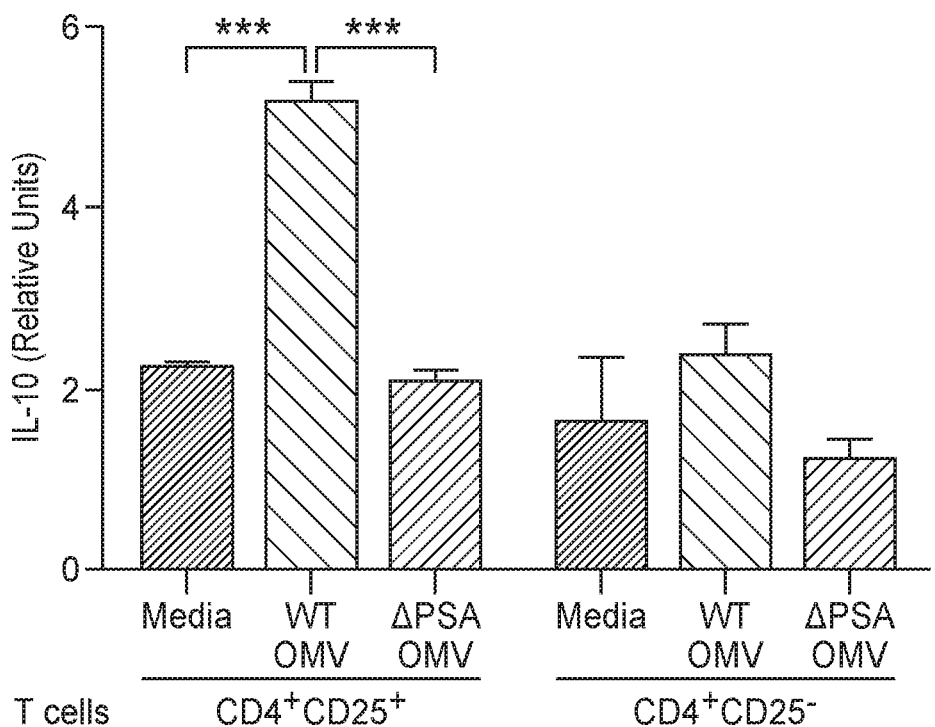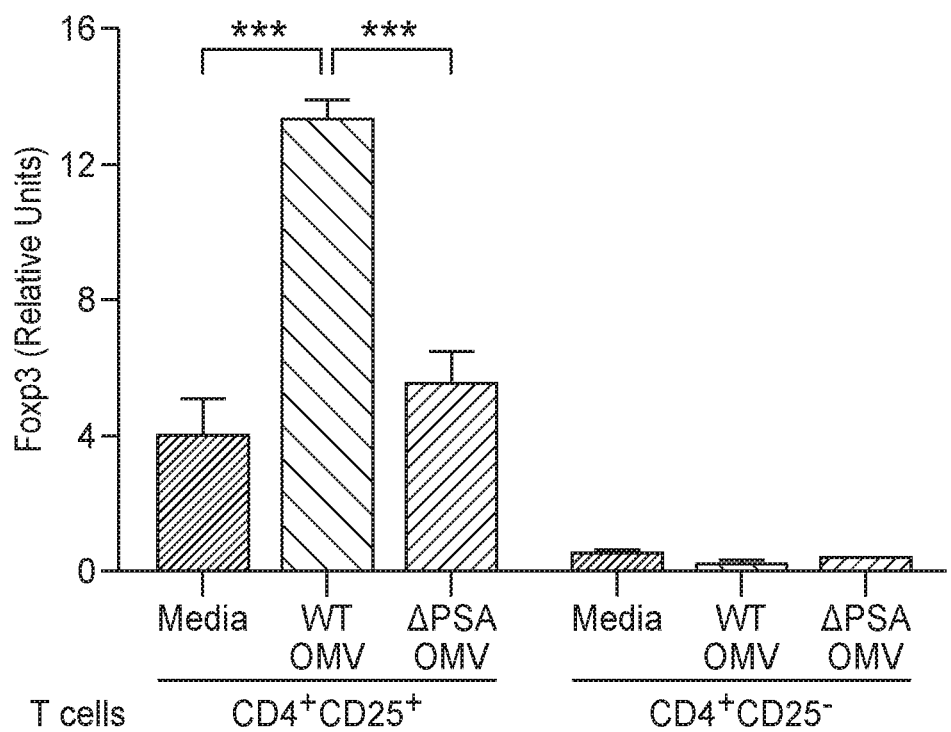
Figure 3E

| No. | Accession No. | Protein Name | WT-OMV | ΔPSZ-OMV | |
|---|---|---|---|---|---|
| BF3567 | gi\|60683022 | hypothetical protein | 864±58 | 452±65 | ** |
| BF2157 | gi\|60681636 | putative lipoprotein | 647±45 | 630±37 | NS |
| BF0595 | gi\|60680161 | hypothetical protein | 341±25 | 296±18 | NS |
| BF2161 | gi\|60681640 | hypothetical protein | 213±24 | 85±5 | ** |
| BF2706 | gi\|60682179 | putative lipoprotein | 178±18 | 128±12 | NS |
| BF1956 | gi\|60681445 | putative outer membrane protein | 161±41 | 129±9 | NS |
| BF0594 | gi\|60680160 | hypothetical protein | 142±12 | 202±8 | ** |
| BF1957 | gi\|60681446 | hypothetical protein | 134±10 | 157±17 | NS |
| BF3067 | gi\|60682536 | putative lipoprotein | 124±31 | 62±6 | NS |
| BF0589 | gi\|60680155 | hypothetical protein | 124±17 | 119±12 | NS |
| BF3432 | gi\|60682894 | hypothetical protein | 117±9 | 96±11 | NS |
| BF2023 | gi\|60681124 | putative ATP/GTP-binding protein | 117±13 | 74±1 | ** |
| BF1619 | gi\|60681115 | hypothetical protein | 117±9 | 147±14 | NS |
| BF3144 | gi\|60682613 | putative lipoprotein | 107±22 | 110±14 | NS |

Figure 7

VEHICLE FOR DELIVERING A COMPOUND TO A MUCOUS MEMBRANE AND RELATED COMPOSITIONS, METHODS AND SYSTEMS

CROSS REFERENCE TO RELATED APPLICATIONS

This application claims the benefit and is a Continuation of application Ser. No. 14/803,598 filed Jul. 20, 2015, which is a Continuation of application Ser. No. 13/082,183 filed Apr. 7, 2011, which claims benefit of U.S. Provisional Patent Application No. 61/345,039 filed on May 14, 2010, and U.S. Provisional Patent Application No. 61/321,527 filed on Apr. 7, 2010, all of which are incorporated by reference herein.

STATEMENT OF GOVERNMENT GRANT

This invention was made with Government support under Grant No. DK078938 awarded by the National Institutes of Health. The Government has certain rights in the invention.

FIELD OF THE INVENTION

The present disclosure relates to a vehicle for delivering a compound to a mucous membrane compositions, methods and systems. In particular, the present disclosure relates to vehicles for delivering a compound to a mucous membrane of the digestive tract.

BACKGROUND OF THE INVENTION

Effective delivery of a desired compound or substance to mucous membrane has been challenging in particular when referred to delivery to the digestive tract, and in particular to human gastrointestinal tract.

The human gastrointestinal tract harbors an extraordinary number of microbes (known as the gut microbiota) that have a profound effect on the development and function of the immune system. Of the innumerable species of bacteria that inhabit the gastrointestinal tract of mammals, Bacteroidetes are the most abundant Gram-negative bacterial phylum.

Identification of immunomodulatory microorganisms and compounds is of particular interest. In particular, Bacteroides fragilis is a human commensal microorganism that has been shown to have immunomodulatory properties. In particular, immunomodulatory properties of Bacteroides fragilis have been associated to Polysaccharide A (PSA) production by the bacterium.

Gram-negative bacteria have evolved intricate mechanisms to export bacterial products; type III secretion systems (T3SS), T4SS and T6SS, which assemble complex surface appendages that translocate bacterial effectors following direct contact with host cells. Another secretion strategy is outer membrane vesicles (OMVs) which are released from the surface of Gram-negative bacteria and deliver a suite of molecular cargo to distant target cells. Although many (if not all) Gram-negative bacteria appear to produce OMVs, genome sequences of human commensal bacteria reveal a universal absence of T3SS, T4SS and T6SS.

However, identification of the mechanism and/or molecular triggers by which B. fragilis (or any commensal bacteria) delivers beneficial microbial molecules to the immune system and performs the immunomodulatory properties has been challenging.

Inflammatory bowel diseases (IBD) such as Crohn's disease and ulcerative colitis represent serious disorders whereby uncontrolled intestinal inflammation leads to severe pathology of the digestive tract. IBD afflicts an estimated 1 million people in the United States. In addition to the medical and social burden of IBD, the incidences of disease are alarmingly increasing in 'Western' societies and current therapies are largely inadequate. Although the cause(s) for IBD remain enigmatic even after decades of research, defects in immune regulation toward intestinal bacteria appear to play an important role in disease'.

BRIEF SUMMARY OF THE INVENTION

The details of one or more embodiments of the disclosure are set forth in the accompanying drawings and the description below. Other features, objects, and advantages will be apparent from the description and drawings, and from the claims.

We reveal herein that PSA is delivered to the host by outer membrane vesicles (OMVs), secretion structures that target bacterial molecules to host cells. OMVs containing PSA are internalized by dendritic cells of the host immune system. Following uptake of OMVs, PSA programs dendritic cells to induce the differentiation of regulatory T cells (Treg) that express Foxp3 and the anti-inflammatory cytokine interleukin-10 (IL-10). Treg development by OMVs requires toll-like receptor 2 (TLR2) expression and IL-10 production by dendritic cells. Remarkably, purified OMVs direct the in vitro differentiation of functional Tregs with potent suppressive activity in a PSA dependent manner. Treatment of animals with OMVs containing PSA prevents experimental colitis and suppresses pro-inflammatory cytokine responses in the gut. These findings reveal that commensal bacteria provide beneficial microbial factors through vesicle secretion, a process that may be engineered into a novel approach for delivery of probiotic therapies for IBD.

In one embodiment, a pharmaceutical composition for delivering a compound to a mucous membrane is provided, comprising an outer membrane vesicle formed by a lipid membrane enclosing an aqueous environment, the vesicle comprising a PSA ligand; and a pharmaceutically appropriate carrier.

In another embodiment, a pharmaceutical composition for delivering a compound to a mucous membrane is provided, comprising an outer membrane vesicle formed by a lipid membrane enclosing an aqueous environment, the vesicle comprising a PSA ligand; and a pharmaceutically appropriate carrier, wherein the lipid membrane is derived from the outer membrane of B. fragilis.

In a more particular embodiment of the composition in paragraph [0012], the PSA ligand is L-PSA.

In yet another embodiment of the composition in paragraph [0012], the pharmaceutical composition further comprises one or more medicaments or treatments known to be useful in the treatment of inflammatory bowel disease.

In one embodiment, a method of treating an inflammatory disease or inflammation in an individual, comprising administering an effective amount of a composition comprising an outer membrane vesicle formed by a lipid membrane enclosing an aqueous environment, the vesicle comprising a PSA ligand.

In a particularized embodiment of the method in paragraph [0016], the inflammatory disease is inflammatory bowel disease.

In yet another embodiment, a vesicle for delivering a compound to a mucous membrane, comprising an outer membrane vesicle formed by a lipid membrane enclosing an aqueous environment, the vesicle comprising a PSA ligand.

In a more particularized embodiment of the vesicle in paragraph [0018], the vesicle further comprises a compound other than PSA.

In another embodiment, a method for directing the differentiation of functional Tregs with potent suppressive activity is provided, comprising an outer membrane vesicle formed by a lipid membrane enclosing an aqueous environment, the vesicle comprising a PSA ligand.

In a more particularized embodiment of the method in paragraph [0020], the Treg cells inhibit T cell proliferation and/or further suppresses immunity by reducing dendritic cell activation.

In another embodiment of the method in paragraph [0020], the method further comprises providing DCs for co-culture, wherein IL-10 is produced and production of IL-10 is dependent upon the presence of TLR2 expression on the DCs, in comparison to PSA activity alone (in the absence of OMVs) on the DC production of IL-10 where TLR2 expression on the DCs is not required.

In another embodiment, a method for identifying compounds that reduce inflammation or improve the symptoms of an inflammatory disease in vitro is provided, comprising providing a candidate compound and incubating the compound with Treg cells; further providing T cells, and then determining whether said Treg cells inhibit T cell activation.

In a more particularized embodiment of the method in paragraph [0023], the method further comprises dendritic cells and/or wherein the Treg cells express Foxp3.

In another embodiment, a bacterial substance for use as a medicament is provided comprising an outer membrane vesicle formed by a lipid membrane enclosing an aqueous environment, the vesicle comprising a PSA ligand.

In a more particularized embodiment of the medicament in paragraph [0025], the bacterial substance further comprises an excipient and/or one or more medicaments known to be useful in the treatment of inflammatory bowel disease.

In another embodiment, a bacterial substance for use in the treatment of inflammatory disease or inflammation is provided comprising an outer membrane vesicle formed by a lipid membrane enclosing an aqueous environment, the vesicle comprising a PSA ligand.

In a more particularized embodiment of the bacterial substance in paragraph [0027], the inflammatory disease is inflammatory bowel diseases.

In another embodiment, a composition for directing the differentiation of functional Treg with potent suppressive activity, comprising an outer membrane vesicle formed by a lipid membrane enclosing an aqueous environment, the vesicle comprising a PSA ligand.

In a more particularized embodiment of the composition in paragraph [0029], the Treg inhibit T cell activation and/or wherein the Treg cells express Foxp3.

Also provided herein, are methods and systems for screening microorganisms and related substances having immunomodulatory and, in particular, anti-inflammatory properties. In particular, provided herein are methods and systems that in several embodiments allow identification of bacterial substances that are able to induce in an individual an immunomodulatory response comparable to the one of *Bacteroides fragilis*.

According to another embodiment, a method is described for identifying a bacterial substance having immunomodulatory ability. The method comprises contacting a candidate bacterial substance with a T cell alone or in presence of an antigen presenting cell, and detecting expression of at least one of one or more anti inflammatory biomarkers selected from the group consisting of IL-10, Foxp3, TGFα1,TGFβ2, Perforin and Granzyme B, and one or more inflammatory biomarkers selected from the group consisting of IFNγ, IFNα, IFNβ, IL-1, IL-4, IL-5, IL-6, IL-8, IL-9, IL-13, IL-21, IL-22, IL-23, IL-17, or TNFα. The method further comprises determining an anti-inflammatory ability of the candidate bacterial substance through detection of an increase of the expression of the one or more anti-inflammatory biomarkers or a decrease of the expression of the one or more inflammatory biomarkers following the contacting.

According to yet another embodiment, a method is described for identifying a bacterial substance having immunomodulatory ability. The method comprises contacting a candidate bacterial substance with an antigen presenting cell, and incubating the antigen presenting cell with a T cell following the contacting. The method further comprises detecting expression of at least one of one or more anti-inflammatory biomarker selected from the group consisting of IL-10, Foxp3, TGFβ1, TGFβ2, Perforin and Granzyme B, and one or more inflammatory biomarker selected from the group consisting of IFNγ, IFNα, IFNβ, IL-1, IL-4, IL-5, IL-6, IL-8, IL-9, IL-13, IL-21, IL-22, IL-23, IL-17 or TNFα. The method further comprises determining an anti inflammatory ability of the candidate bacterial substance through detection of an increase of the expression of the one or more anti-inflammatory biomarkers or a decrease of the expression of the one or more inflammatory biomarkers following the incubating.

According to another aspect, a method is described for identifying a bacterial substance having immunomodulatory ability in animals. The method comprises treating a transgenic marker non-human animal with a candidate bacterial substance, the transgenic marker non-human animal genetically modified to express at least one of one or more labeled anti-inflammatory biomarkers selected from the group consisting of IL-10, Foxp3, TGFβ1, TGFβ2, Perforin and Granzyme B, and one or more labeled inflammatory biomarker selected from the group consisting of IFNγ, IFNα, IFNβ, IL-1, IL-4, IL-5, IL-6, IL-8, IL-9, IL-13, IL-21, IL-22, IL-23, IL-17 or TNFα. The method further comprises detecting expression in the transgenic marker non-human animal of at least one of the one or more anti-inflammatory biomarkers or at least one of the inflammatory biomarkers following the treating and determining an anti-inflammatory ability of the candidate bacterial substance through detection of an increase of the expression of the one or more anti-inflammatory biomarkers or a decrease of the expression of the one or more inflammatory biomarkers following the treating.

According to another aspect a system for screening a bacterial substance is described. The system comprises at least two of a T cell, an antigen presenting cell and reagents for detection of at least one of one or more anti-inflammatory biomarkers selected from the group consisting of IL-10, Foxp3, TGFβ1, TGFβ2, Perforin and Granzyme B and one or more labeled inflammatory biomarker selected from the group consisting of IFNγ, IFNα, IFNβ, IL-1, IL-4, IL-5, IL-6, IL-8, IL-9, IL-13, IL-21, IL-22, IL-23, IL-17 or TNFα, for simultaneous, combined or sequential use in a method to identify an anti-inflammatory bacterial substance herein described.

The methods and systems herein described can be used in connection with medical, pharmaceutical, veterinary applications as well as fundamental biological studies and various applications, identifiable by a skilled person upon reading of the present disclosure, wherein investigating immunomodulatory ability and in particular anti-inflammatory ability of a substance is desirable.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A shows OMVs produced by wild-type *B. fragilis* and *B. fragilis* ΔPSA that were detected by transmission electron microscopy of EDL (electron dense layer)-enriched *B. fragilis*. FIG. 1B shows an immunoblot analysis of whole cell (WC) and outer membrane vesicles (OMV) extracts from wild-type and SA-mutant bacteria. FIG. 1C shows immunogold labeling of purified OMVs, stained with anti-PSA and anti-IgG-colloidal gold conjugate (5 nm), analyzed by electron microscopy. FIG. 1D shows a glycoprotein staining of capsular polysaccharide preparations from whole cells and OMVs.

FIGS. 2A-2F illustrates exemplary results showing that OMVs protect animals from experimental colitis and intestinal inflammation in a PSA-dependent manner. FIG. 2A shows a diagram reporting weight loss in animal groups following the induction of TNBS colitis (day 0) measured as reduction from initial weight until day of sacrifice (day 4). All groups contained at least 4 animals, with error bars indicating standard error of the mean (SEM). Results are representative of 3 independent trials. p values determined by one-way ANOVA: * p<0.05; * p<0.001. FIG. 2B shows images of unmanipulated colons immediately following resection and quantification of length (graph) from vehicle treated (EtOH) and TNBS groups (n=4 animals/group). Error bars indicate SEM. Results are shown from 3 combined experiments performed independently. p values determined by one-way ANOVA: * p<0.001. NS: not significant. FIG. 2C shows images from hematoxylin and eosin (H & E) stained colon sections representative of each treatment group. FIG. 2D shows colitis scores from animals assigned by a blinded pathologist (G.W.L) according to a standard scoring system (ONLINE METHODS) (Scheiffele and Fuss. (2001) Induction of TNBS colitis in mice. Current Protocols in Immunology. 1.19.1-15.19.14) Each symbol represents an individual animal. Results are shown from 3 combined experiments performed independently. *** p<0.001. NS: not significant. FIGS. 2e and f show diagrams illustrating cytokine transcript analysis by qRT-PCR from RNA recovered from whole colons (FIG. 2E) or purified CD4+ T cell from mesenteric lymph nodes (FIG. 2F). Error bars indicate SEM from 4 animals/group. Results are representative of 3 independent trials.

FIGS. 3A-3F shows results indicating that PSA containing OMVs induce IL-10 production and Foxp3 expression from T cells co-cultured with treated DCs. FIG. 3A shows flow cytometry (FC) analysis of OMV internalization by DCs. OMVs were labeled with FITC (Fluorescein isothiocyanate) and incubated with cultured DCs for various times (as indicated). Cells were stained with anti-CD11c. Percentages show CD11C+OMV+ populations. FIG. 3B shows FC plots of DCs incubated with WT-OMVs and ΔPSA-OMVs for various times (as indicated) and stained with anti-CD11c and anti-MHCII. Percentages show MHCII+ populations among CD11c+ cells. FIG. 3C shows ELISA analysis for IL-10 of culture supernatants from DCs or DC-T cell co-cultures, where DCs were pulsed with OMVs for 18 hours, washed and incubated with primary CD4+ T cells or not. Supernatants were collected at day 4 of culture. Media samples indicate DCs that were not pulsed with OMVs, but otherwise treated identically. Anti-CD3 was added to some samples to augment T cell responses. Error bars indicate SEM from triplicate samples. Results are representative of over 5 independent trials. * p<0.05; ** p<0.01. FIG. 3D(i) shows ELISA analysis similar to FIG. 3c, but also including DCs differentiated from IL-10−/− animals. Error bars indicate SEM from triplicate samples. Results are representative of 3 independent trials. * p<0.05. NS: not significant. FIG. 3D(ii) shows ELISA analysis similar to FIG. 3c, but also including DCs differentiated from TLR2−/− animals. SEA: staphylococcal enterotoxin A. Error bars indicate SEM from triplicate samples. Results are representative of 3 independent trials. * p<0.05. NS: not significant. FIG. 3E shows transcript levels of IL-10 (left) and Foxp3 (right) as determined by qRT-PCR of RNA received from purified T cell subsets following in vitro culture with DCs. Co-cultures were set up as in (c-e); on day 4, CD4+CD25+ and CD4+CD25-T cell were purified by magnetic bead separation (>95% purity) and RNA extracted with RNeasy mini kit. Relative values were normalized to β-actin. Error bars indicate SEM from triplicate samples. Results are representative of 3 independent trials. * p<0.05; *** p<0.001. NS: not significant. FIG. 3F shows co-cultures set up as in (c-e), but using CD4+ T cells from Foxp3-GFP mice. Following 4 days of culture with OMV pulsed DCs, cells were stained with anti-CD4 and Foxp3 detected by GFP expression using FC. Results are representative of 2 independent trials.

FIG. 4A shows FC histograms of IL-10 expression by CD4+ T cell subsets following 4 day co-culture with DCs treated with OMVs. Splenic CD4+ T cell were purified from IL-10-GFP mice, stained with anti-CD4 and anti-CD25 following co-culture, and IL-10 expression measured by GFP expression. Percentages show IL-10+ populations among CD4+CD25+ and CD4+CD25-subsets. Results are representative of 3 independent trials. FIG. 4B shows in vitro suppression of naïve responder cells by purified CD4+CD25+ T cells following co-culture with DCs treated with media (control), WT-OMVs and ΔPSA-OMVs. Cell proliferation was measured by FC of CFSE dilution. Treg:Teff ratios are indicated, and percentages show total proliferating cells. No Treg: CD4+CD25-cells only. Results are representative of 2 independent trials. FIG. 4C shows the quantification of percentage of CD4+ T cells in each proliferating peak (as is labeled as 1, 2, 3, 4, 5 in FIG. 4b). Results are shown from 3 combined experiments performed independently. *** p<0.001; * p<0.05. NS: not significant.

FIG. 7 shows OMVs from wild-type or PSA deletional mutant B. fragilis show no significant difference in protein composition. Proteome mass spectrometry shows 100% overlap of the identified proteins (>1 unique peptide identified for each protein) between WT-OMVs and ΔPSA-OMVs. Among all of the identified proteins, we semi-quantitatively compared the amount of those relatively abundant proteins according to the number of unique peptides identified for each of them. Majority of them show no difference performed independently. Errors indicate SEM. p value determined by Student's t-test. **: $p<0.01$; *: $p<0.05$; NS: not significant.

DETAILED DESCRIPTION OF THE INVENTION

Figure 1A:
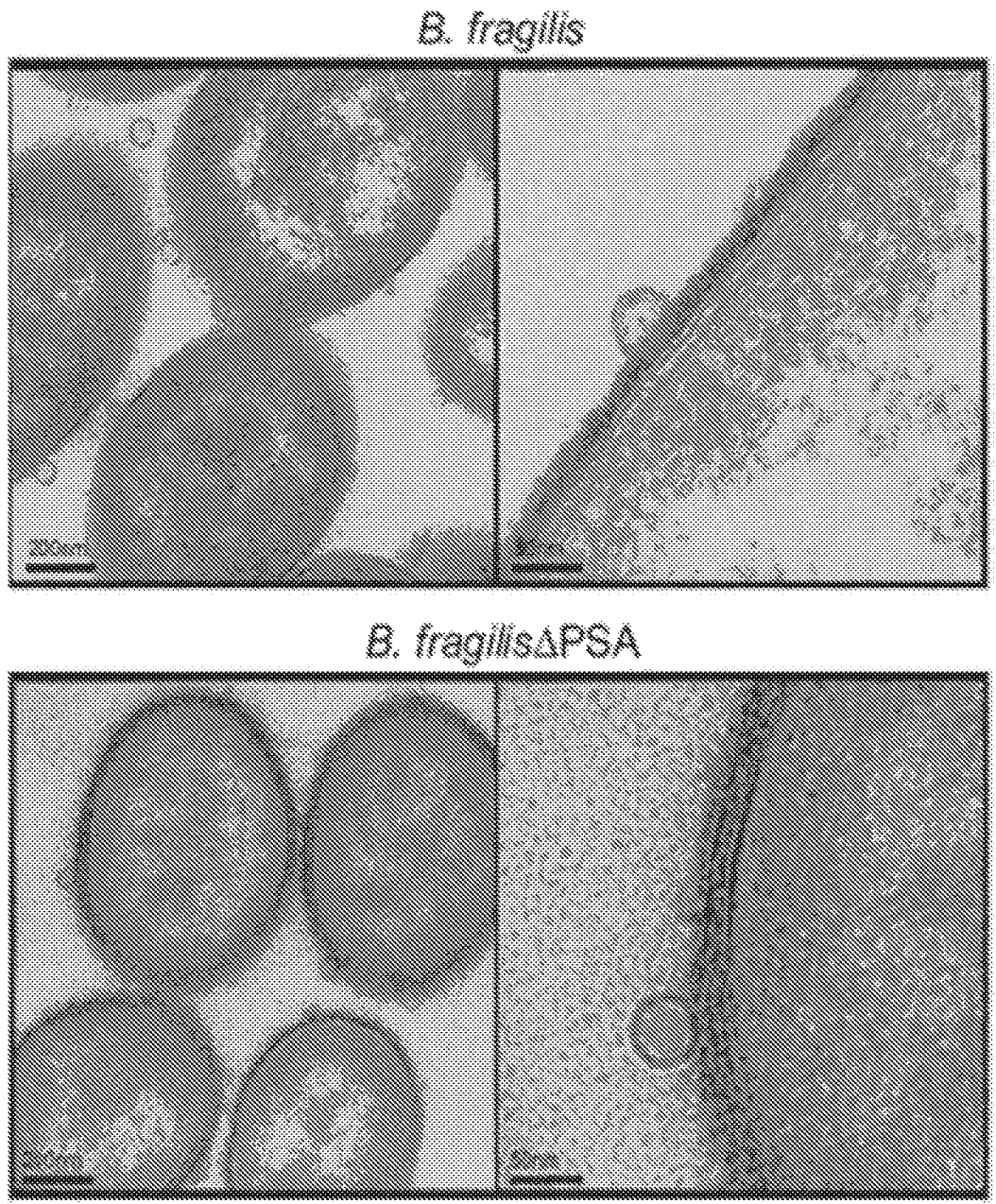
FIGS. 1A-1D shows that outer membrane vesicles (OMVs) from *Bacteroides fragilis* contain PSA.

Vehicles are herein described that are suitable for delivering a compound to a mucous membrane.

The terms "wild-type OMV", "PSA containing OMVs", and "PSA-OMV", are herein used interchangeably.

The term "vehicle" in the sense of the present disclosure indicates a medium in which a compound is administered, and in which the compound is comprised, expressed, and/or displayed. Exemplary vehicles comprise any of various media acting usually as solvents, carriers, or binders for active ingredients, with particular reference to drugs.

The term "deliver" and delivering" referred to a compound or substance in the sense of the present disclosure indicates passage of the compound or substance from an originating location to a target location, and in particular to a location formed by one or more cells, tissues, or organs of an individual. In particular, a compound is delivered in the sense of the present disclosure when the passage is performed so that at least one activity associated to the delivered compound can be exerted on the one or more cells, tissues or organs of the individual.

The term "compound" as used herein indicates any chemical substance comprised of one or more chemical elements and comprises various substances, molecules or component that include but are not limited to biomolecules and in particular drugs. The term "biomolecule" as used herein indicates a substance compound or component associated to a biological activity including but not limited to sugars, aminoacids, peptides proteins, oligonucleotides, polynucleotides, polypeptides, organic molecules, haptens, epitopes, biological cells, parts of biological cells, vitamins, hormones and the like. The term "drug" as used herein indicates substance that, when absorbed into the body of a living organism, alters normal bodily function. In particular, drugs in the sense of the present disclosure include a chemical substance used in the treatment, cure, prevention, or diagnosis of disease or used to otherwise enhance physical or mental well-being.

If PSA is for instance the above 'compound' then additional different compounds could also be delivered, in addition to PSA, by the vesicle.

The term "mucous membrane" in the sense of the present disclosure indicates a lining of mostly endodermal origin, covered in epithelium, which are involved in absorption and secretion. In an individual, mucous membranes line various body cavities that are exposed to the external environment and internal organs. Mucous membranes are at several places continuous with skin: at the nostrils, the mouth, the lips, the eyelids, the ears, the genital area, and the anus.

In the compositions, and related methods and systems herein described, the vehicle is formed by a vesicle comprising one or more compounds to be delivered.

A "vesicle" in the sense of the present disclosure is a supramolecular complex formed by a membrane forming lipid and additional molecules assembled in an aqueous environment. In particular, in vesicles herein described the membrane forming lipids are arranged in a lipid layer enclosing an internal aqueous environment herein also indicated as cytosol.

The term "membrane forming lipid" or "amphipatic lipid" as used herein indicates a lipid possessing both hydrophilic and hydrophobic properties that in an aqueous environment assemble in a lipid layer structure that consists of either one or two opposing layers of amphipatic molecules known as polar lipid. Each polar lipid has a hydrophilic moiety, i.e., a polar group such as, a derivatized phosphate or a saccharide group, and a hydrophobic moiety, i.e., a long hydrocarbon chain. Exemplary polar lipids include phospholipids, sphingolipids, glycolipids, ether lipids, sterols and alkylphosphocholins. Amphipatic lipids include but are not limited to membrane lipids, i.e. amphipatic lipids that are constituents of a biological membrane, such as phospholipids like dimyrisoylphosphatidylcholine (DMPC) or Dioleoylphosphoethanolamine (DOPE) or dioleoylphosphatidylcholine (DOPC). In an embodiment, the membrane of the vesicle is formed by a lipid bilayer mimicking a plasma membrane (a biological membrane separating the interior of a cell from the outside environment, and enclose an aqueous environment) and in particular the outer membrane of B. fragilis.

Vesicles herein described also comprise a lipopolysaccharide (LPS) either associated with the membrane of the vesicle or comprised in the aqueous environment of the vesicle. The term "lipopolysaccharide" as used herein indicates large molecules consisting of a lipid and a polysaccharide joined by a covalent bond; they are found in the outer membrane of Gram-negative bacteria, act as endotoxins and elicit strong immune responses in animals. In particular, vesicles herein described comprise one or more LPS of B. fragilis which are identifiable by a skilled person.

Vesicles herein described can also comprise a peptidoglycan either associated with the membrane of the vesicle or comprised in the aqueous environment of the vesicle. The term "peptidoglycan" as used herein indicates a polymer consisting of sugars and amino acids that forms a mesh-like layer outside the plasma membrane of bacteria (Eubacteria, not Archaebacteria), forming the cell wall. In particular, vesicles herein described comprise one or more peptidoglycans of *B. fragilis* which are identifiable by a skilled person.

Additional compounds that can be comprised in the vesicles, comprise membrane proteins, membrane lipids carbohydrates and nucleic acids, and in particular, membrane proteins, membrane lipids carbohydrates and nucleic acids of *B. fragilis*.

Exemplary vesicles in the sense of the present disclosure comprise small membrane-enclosed sacs that can store or transport substances. Vesicles can form naturally because of the properties of the membrane forming lipid, or they may be prepared from bacterial membranes. Most vesicles have specialized functions depending on what materials they contain on the membrane and/or the aqueous environment.

In an embodiment, the vesicles herein described are formed by portions of membranes of bacteria. In an embodiment, vesicles are formed by Outer Membrane Vesicles (OMVs) of the bacteria.

In an embodiment, the vesicles herein described are formed by portions of membranes of *B. fragilis* and in particular from the OMV of *B. fragilis* as exemplified in the Examples section.

In an embodiment, the delivered compound can be a drug, candidate drug, a supplement (a product taken orally that contains one or more ingredients (as vitamins or amino acids) that are intended to supplement one's diet and are not considered food) or any other compound whose delivery to the mucous membrane is desired. One or more of those compounds can be include in the vesicles herein described in a suitable dosage that can be determined by the skilled person in view of the specific compound to be delivered.

In an embodiment, the compound comprises one or more zwitterionic polysaccharide and in particular Polysaccharide A.

The term "zwitterionic polysaccharide" as used herein indicates synthetic or natural polymers comprising one or more monosaccharides joined together by glicosidic bonds, and including at least one positively charged moiety and at least one negatively charged moiety. Zwitterionic polysaccharides include but are not limited to polymers of any length, from a mono- or di-saccharide polymer to polymers including hundreds or thousands of monosaccharides. In some embodiments, a zwitterionic polysaccharide can include repeating units wherein each repeating unit includes from two to ten monosaccharides, a positively charged moiety (e.g. an free positively charged amino moiety) and a negatively charged moiety (such as sulfonate, sulfate, phosphate and phosphonate). In some embodiment ZPs can have a molecular weight comprised between 500 Da and 2,000,000 Da. In some embodiments, the ZPs can have a molecular weight comprised between 200 and 2500. Exemplary ZPS include but are not limited to PSA and PSB from *Bacteroides Fragilis*, CP5/CD8 from Staphylococcus aureus, and Sp1/CP1 from *Streptococcus* pneumonia. Zwitterionic polysaccharides can be isolated from natural sources, and in particular from bacterial sources, e.g. by purification. Zwitterionic polysaccharides can also be produced by chemical or biochemical methods, as well as by recombinant microorganism technologies all identifiable by a skilled person. Thus, those methods and technologies will not be further described herein in detail.

The wording "polysaccharide A" (or PSA, or PSA ligand) as used herein indicates a molecule produced by the PSA locus of *Bacteroides fragilis* and derivatives thereof which include but are not limited to polymers of the repeating unit {→3) α-d-AAT Galp(1→4)-[β-d-Galf(1→3)] α-d-GalpNAc (1→3)[4,6-pyruvate]-β-d-Galp(1→}, where AATGal is acetamido-amino-2,4,6-trideoxygalactose, and the galactopyranosyl residue is modified by a pyruvate substituent spanning 0-4 and 0-6. The term "derivative" as used herein with reference to a first polysaccharide (e.g., PSA), indicates a second polysaccharide that is structurally related to the first polysaccharide and is derivable from the first polysaccharide by a modification that introduces a feature that is not present in the first polysaccharide while retaining functional properties of the first polysaccharide. Accordingly, a derivative polysaccharide of PSA, usually differs from the original polysaccharide by modification of the repeating units or of the saccharidic component of one or more of the repeating units that might or might not be associated with an additional function not present in the original polysaccharide. A derivative polysaccharide of PSA retains however one or more functional activities that are herein described in connection with PSA in association with the anti-inflammatory activity of PSA.

In one embodiment, low molecular weight PSA (L-PSA) is from 70 kDa to 200 kDa and high molecular weight PSA (H-PSA) is above 200 kDa.

In an embodiment, the mucous membrane is a mucous membrane of the digestive tract of an individual, and in particular intestinal mucosa, gastric mucosa, esophageal mucosa, buccal mucosa, oral mucosa and/or buccal mucosa.

In an embodiment, the vesicles herein described can be used in connection with procedures and applications such as the ones described in U.S. Provisional Application Ser. No. 61/321,527 herein enclosed as Exhibit A which forms part of the present disclosure and is incorporated herein by reference in its entirety.

In an embodiment, the vesicles herein described can be used in connection with methods and systems such as the ones described in U.S. patent application Ser. No. 12/766,787 herein enclosed as Exhibit B which forms part of the present disclosure and is incorporated herein by reference in its entirety.

In an embodiment, vesicles herein described can be used in a method to deliver the compound to a mucous membrane of an individual. In particular, the method comprises contacting a vesicle comprising the compound with the mucous membrane for a time and under condition to allow contact of the substance with the membrane. In the method, the vesicle is formed by a lipid membrane enclosing an aqueous environment and the compound to be delivered is comprised in the aqueous environment of the vesicle.

In another embodiment, a composition or pharmaceutical composition comprising of the vesicle or OMV is contacted with the mucous membrane for a time and under condition to allow contact of the substance with the membrane.

The term "contacting" or "incubating" as used herein indicates actions directed to creation of a spatial relationship between two items provided for a time and under condition such that at least one of the reciprocal or non reciprocal action or influence between the two items can be exerted. In particular, incubation can be performed between a vesicle and a mucous membrane and can result in a direct contact and/or interaction between the vesicle and the mucous membrane or can result in a modification of the mucous membrane following an indirect action of the vesicle (e.g. following activation or modification of another substance which directly interacts with the membrane).

Suitable conditions for performing the contacting or incubation are identifiable by a skilled person upon reading of the present disclosure in view of the compound, the mucous membrane, and the experimental design.

In an embodiment, vesicles herein described can be comprised in a composition for delivering a compound to a mucous membrane. The composition comprises one or more vesicles herein described optionally in combination with an additional vehicle acting as a solvent, carrier, binder or diluents for the vesicles.

The term "condition"—when referring to the status of an animal or human—as used herein indicates a usually the physical status of the body of an individual, as a whole or of one or more of its parts, that does not conform to a physical status of the individual, as a whole or of one or more of its parts, that is associated with a state of complete physical, mental and possibly social well-being. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof.

In particular, in embodiments where the compound is used as an anti-inflammatory compound, the condition can be any condition associated to an inflammation or inflammatory response; or a condition described as an inflammatory disease itself. The wording "associated to" as used herein with reference to two items indicates a relation between the two items such that the occurrence of a first item is accompanied by the occurrence of the second item, which includes but is not limited to a cause-effect relation and sign/symptoms-disease relation.

Conditions associated with an inflammation (or inflammatory diseases) in humans include but are not limited to inflammatory bowel disease, including but not limited to Crohn's disease and ulcerative colitis, asthma, dermatitis, arthritis, myasthenia gravis, Grave's disease, multiple sclerosis (MS), and psoriasis. A person of skill in the art would be able to identify such subjects suffering from the aforementioned diseases using the appropriate clinical criteria.

In one embodiment, compositions, pharmaceutical composition comprising OMVs containing PSA can be used for the prevention of inflammatory diseases, such as, but not limited to, inflammatory bowel disease (including Crohn's disease and ulcerative colitis), asthma, dermatitis, arthritis, myasthenia gravis, Grave's disease, multiple sclerosis, and psoriasis.

The term "treatment" or "treated" as used herein indicates any activity whether part of a medical care, or not, for or deals with a condition medically or surgically in animals or humans. Such treatments can be administered by either medical or non-medical personnel.

In some embodiments, where the composition is to be administered to an individual the composition can be a pharmaceutical composition, and comprise one or more vesicles each comprising PSA. In a more particular embodiment, the pharmaceutical composition can comprise of one or more vesicles each comprising PSA and one or more of another compound, and/or a pharmaceutically acceptable or appropriate carrier/vehicle.

In another embodiment, the above pharmaceutical composition, comprising one or more vesicles each comprising PSA and one or more of another compound, and/or a pharmaceutically acceptable or appropriate carrier/vehicle, wherein an individual/subject with an inflammatory condition or inflammation given this composition shows an improvement.

In some embodiments, the vesicles herein described can be included in pharmaceutical compositions together with an excipient or diluent. In particular, in some embodiments, pharmaceutical compositions contain vesicles herein described, in combination with one or more compatible and pharmaceutically acceptable vehicle, and in particular with pharmaceutically acceptable diluents or excipients.

The term "excipient" as used herein indicates an inactive substance used as a pharmaceutically acceptable or appropriate carrier for the active ingredients of a medication. Suitable excipients for the pharmaceutical compositions herein disclosed include any substance that enhances the ability of the body of an individual to absorb vesicles herein described. Suitable excipients also include any substance that can be used to bulk up formulations with vesicles herein described to allow for convenient and accurate dosage. In addition to their use in the single-dosage quantity, excipients can be used in the manufacturing process to aid in the handling of vesicles herein described. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

Pharmaceutically acceptable or appropriate carriers can be, but not limited to, organic or inorganic, solid or liquid excipient which is suitable for the selected mode of application such as oral application or injection, and administered in the form of a conventional pharmaceutical preparation. Such preparation includes solid such as tablets, granules, powders, capsules, and liquid such as solution, emulsion, suspension and the like. Said carrier includes starch, lactose, glucose, sucrose, dextrine, cellulose, paraffin, fatty acid glyceride, water, alcohol, gum arabic and the like. If necessary, auxiliary, stabilizer, emulsifier, lubricant, binder, pH adjustor controller, isotonic agent and other conventional additives may be added.

The pharmaceutically acceptable or appropriate carrier may well include other compounds known to be beneficial to an impaired situation of the gut, (e.g., antioxidants, such as Vitamin C, Vitamin E, Selenium or Zinc); or a food composition. The food composition can be, but is not limited to, milk, yoghurt, curd, cheese, fermented milks, milk based fermented products, ice-creams, fermented cereal based products, milk based powders, infant formulae, tablets, liquid bacterial suspensions, dried oral supplement, or wet oral supplement.

The term "diluent" as used herein indicates a diluting agent which is issued to dilute or carry an active ingredient of a composition. Suitable diluent include any substance that can decrease the viscosity of a medicinal preparation.

In certain embodiments, compositions, compounds, and, in particular, pharmaceutical compositions can be formulated for enteral administration including, but not limited to, i) by mouth (orally) as tablets, capsules, or drops; ii) by gastric feeding tube, duodenal feeding tube, or gastrostomy; and enteral nutrition; and iii) rectally as a suppository.

In some embodiments, vesicles herein described comprising PSA can be used in a method of treating or preventing a condition in an individual.

The method comprises administering to the individual an effective amount of the composition or pharmaceutical composition. The term "individual" as used herein includes a single biological organism wherein inflammation can occur including but not limited to animals and in particular higher animals and in particular vertebrates such as mammals and in particular human beings.

The "effective amount", "amount effective to," or "amount of X effective to" refers to an amount of the compound, composition or pharmaceutical composition that is effective to treat, relieve, reduce, or improve to some extent one or more of the symptoms of the disease in need of treatment, or to retard initiation of clinical markers or symptoms of a disease in need of prevention, when the compound is administered. Thus, for example an effective amount refers to an amount of the compound/composition/pharmaceutical ingredient which exhibits the 'improved' effects, as noted below.

The "effective amount" may be empirically determined by experimenting with the compounds concerned in known in vivo and in vitro model systems for a disease in need of treatment. An effective amount will vary according to the weight, sex, age and medical history of the individual, as well as the severity of the patient's condition(s), the type of disease(s), mode of administration, and the like. An effective amount may be readily determined using routine experimentation, e.g., by titration (administration of increasing dosages until an effective dosage is found) and/or by reference to amounts that were effective for prior patients. Generally, the effective amount of the present invention will be administered in dosages ranging between about 0.1 mg/kg and about 20 mg/kg of the patient's body-weight.

As used herein, the phrase "prophylactically effective amount" includes the amount of the compound/composition/pharmaceutical composition which is sufficient to result in the prevention or reduction of the development, recurrence or onset of one or more symptoms associated with a disorder (or to enhance or improve the prophylactic effect(s) of another therapy (e.g., another prophylactic agent).

It is further contemplated that the compound/composition/pharmaceutical composition of the present invention can be used with one or more known medicaments known to be useful in the treatment or prevention of inflammatory diseases, either separately or in combination.

For example the compound/composition/pharmaceutical composition of the present invention can be combined with one or a combination of medicaments/treatments known to be useful in the treatment of IBD such as, but not limited to, sulfasalazine (Azulfadine), mesalamine (Asacol, Pentasa), immunosuppressants (Imuran, 6-MP, cyclosporine); methotrexate, TNF-alpha inhibitors (Remicade and Humira); and corticosteroids (Entocort and prednisone). Other treatments (experimental) for ulcerative colitis, include aloe vera, butyrate, boswellia, probiotics, antibiotics, immunosuppressive therapy, and nicotine.

For example the compound/composition/pharmaceutical composition of the present invention can be combined with one or a combination of medicaments/treatments known to be useful in the treatment of MS such as, but not limited to, Avonex®, Betaseron®, and Copaxone®. Rebif®; Extavia® Novantrone® (mitoxantrone); Tysabri® (natalizumab), and Gilenya® (fingolimod). Other drugs include intravenous immunoglobulin (IVIg) therapy, methotrexate, azathioprine (Imuran®), and cyclophosphamide (Cytoxan®); corticosteroids; cytoxan® (cyclophosphamide); Imuran® (azathioprine); methotrexate; plasma exchange; pulse solu-medrol® (IV methylprednisolone); prednisone; Decadron® (dexamethasone); Medrol® (oral methylprednisolone); Plasmapheresis (plasma exchange); intravenous immunoglobulin (IVIg) therapy.

In another embodiment, it is possible that these other medicaments could be expressed or delivered within the OMVs themselves.

As used herein, "improved," "improvement," and other grammatical variants, includes any beneficial change in the individual/subject resulting from a treatment. A beneficial change is any way in which a patient's condition is better than it would have been in the absence of the treatment. "Improved" includes, but is not limited to, prevention of an undesired condition, slowing the rate at which a condition worsens, delaying the development of an undesired condition, restoration to an essentially normal condition; causing the patient to go into remission more often or remain in remission for longer periods than without treatment (i.e. where the degree of inflammation in the patient is less (or absent); or the person usually is without symptoms); reduction in the number and/or severity of relapses; and reduction in the development of new areas of inflammation as seen on magnetic resonance imaging (MRI) scans.

More particularly, improvement in IBD encompasses a reduction in the severity or duration in any one or more clinical IBD symptoms, such as, but not limited to, Abdominal cramps and pain; Bloody stool; diarrhea; urgency to have a bowel movement; fever; loss of appetite; weight loss; mucus in the stool; ulceration of the large intestine; and anemia (due to blood loss). For example improvement in MS encompasses a reduction in the severity or duration in any one or more clinical MS symptoms, such as, but not limited to fatigue; visual disorders; numbness; dizziness/vertigo; bladder and bowel dysfunction; weakness; tremor; impaired mobility; sexual dysfunction; slurred speech; spasticity (leg stiffness); swallowing disorders; chronic aching pain; depression; mild cognitive and memory difficulties Moreover, improved," "improvement," and other grammatical variants includes any change resulting in the reduction in the severity, duration, and/or risk of developing complications of the inflammatory disease. For IBD, 'improved' could mean for example, a reduced risk of the IBD subject developing profuse bleeding from the ulcers; perforation (rupture) of the bowel; strictures and obstruction; fistulae (abnormal passage) and perianal disease; toxic megacolon (acute nonobstructive dilation of the colon); and malignancy (for example, colon cancer).

In an embodiment, at least two of the membrane forming lipid, vesicles, PSA and one or more additional compounds to be delivered can be comprised in a system possibly together with other reagents suitable to be used in the methods herein described.

The systems can be provided in the form of kits of parts. In a kit of parts, the membrane forming lipid, vesicles, PSA, addition compounds, medicaments, and other the reagents can be included in one or more compositions, or each lipid, vesicles, PSA, addition compounds, medicaments compound and reagent can be in a composition together with a suitable vehicle.

Additional components can include labeled molecules and in particular, labeled capture agents specific for an anti-inflammatory or an inflammatory biomarker or a molecule associated to the expression thereof, a microfluidic chip, reference standards, and additional components identifiable by a skilled person upon reading of the present disclosure.

The term "capture agent" as used herein indicates a compound that can specifically bind to a target. The wording "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc. By "stable complex" is meant a complex that is detectable and does not require any arbitrary level of stability, although greater stability is generally preferred. In some embodiments, the kit can comprise labeled polynucleotides or labeled antibodies.

The components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

The term "immunomodulatory" as used herein indicates the ability to promote a state associated with absence of an inflammatory response. Particular immunomodulatory properties comprise anti-inflammatory properties, wherein the term anti-inflammatory refers to the property of a substance or treatment that prevents or reduces inflammation.

The term "inflammation", "inflammatory state" or "inflammatory response" as used herein indicate the complex biological response of vascular tissues of an individual to harmful stimuli, such as pathogens, damaged cells, or irritants, and includes secretion of cytokines and more particularly of pro-inflammatory cytokine, i.e. cytokines which are produced predominantly by activated immune cells such as microglia and are involved in the amplification of inflammatory reactions. Exemplary pro-inflammatory cytokines include but are not limited to IL-1, IL-6, TNF-a, IL-17, IL21, and IL23. Exemplary inflammations include acute inflammation and chronic inflammation. The wording "acute inflammation" as used herein indicates a short-term process characterized by the classic signs of inflammation (swelling, redness, pain, heat, and loss of function) due to the infiltration of the tissues by plasma and leukocytes. An acute inflammation typically occurs as long as the injurious stimulus is present and ceases once the stimulus has been removed, broken down, or walled off by scarring (fibrosis). The wording "chronic inflammation" as used herein indicates a condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis.

The term "substance" as used herein indicates a matter of particular or definite chemical constitution. The term "bacterial substance" indicates matter of bacterial origin such as, a live bacteria, dead bacteria, and in particular heat-killed bacteria, bacterial extracts, purified molecules from bacteria, a combination of molecules purified from bacteria, or vesicles containing one molecule or a combination of molecules purified from bacteria or purified vesicles from bacteria. In particular, bacterial substance can be formed by, or comprises, the outer membrane vesicles (OMVs) which are vesicles released from the surface of bacteria and deliver a suite of molecular cargo to distant target cells. Even more particularly, the bacterial substance can be formed by, or comprises, the OMVs of *B. Fragilis*, and more particularly, such OMVs are further comprised of PSA.

Bacterial substance comprises substance derived from a same bacteria and substance derived from two or more different bacteria.

The term "bacteria" as used herein indicates large group of unicellular, prokaryote, microorganisms, typically of a few micrometers in length, and having a wide range of shapes. In particular, bacteria in the sense of the present disclosure comprise bacteria of the human flora, i.e. the assemblage of microorganisms that reside on the surface and in human tissues and bodily fluids such as deep layers of skin, in saliva, oral or vaginal mucosa, and in the gastrointestinal tracts. Bacterial flora comprises gut flora (bacteria detectable in the digestive tract of humans) vaginal flora (bacteria detectable in the fibromuscular tubular tract leading from the uterus to the exterior of the body in female humans) and skin flora (bacteria detectable in human skin). More specifically, bacteria in the sense of the present disclosure can be formed by one or more bacteroidetes of the gut flora and in particular one or more bacteroides, a genus of Gram-negative, non endospore forming anaerobes bacillus bacteria, symbiotic with humans and identifiable by a skilled person. A representative bacteroides is *B. fragilis*.

The term "transgenic marker non-human animal" as used herein refers to an animal that contains non-native, genetic material that has been transferred naturally or by any of a number of genetic engineering techniques. Such non-native, genetic material (or transgene) may act as a "biomarker" (as defined herein) and/or retain the ability to produce RNA or protein in the non-human animal.

The term "T cell" as used herein indicates a sub-group of lymphocytes (a type of white blood cell or leukocyte) including different cell types identifiable by a skilled person. T-helper cell according to the present disclosure and include effector $T_h$ cells (such as Th1, Th2 and Th17)—i.e. Th cells that secrete cytokines, proteins or peptides that stimulate or interact with other leukocytes, including $T_h$ cells—and suppressor Th cells (such as Treg) i.e. Th cells that suppress activation of the immune system and thereby maintain immune system homeostasis and tolerance to self-antigens.

The term "antigen presenting cell" as used herein indicates a cell that displays foreign antigen complex with major histocompatibility complex (MHC) on its surface. In particular, antigen presenting cell comprise dendritic cell, macrophage, B cells and additional cells identifiable by a skilled person.

The term "contacting" or "incubating" as used herein indicates actions directed to creation of a spatial relationship between two items provided for a time and under condition such that at least one of the reciprocal or non reciprocal action or influence between the two items can be exerted. In particular, incubation can be performed between a bacterial substance and a cell and can result in a direct contact and/or interaction between the bacterial substance and the cell or can result in a modification of the cell following an indirect action of the bacterial substance (e.g. following activation or modification of another substance which directly interacts with the cell).

The 'treating', or 'treatment' can be performed by administering the bacterial substance, compound, composition, or pharmaceutical composition by topical or systemic administration. Systemic administration includes enteral administration (e.g. oral administration, administration by gastric feeding tube, administration by duodenal feeding tube, gastrostomy, enteral nutrition, and rectal administration) and parenteral administration (e.g. intravenous administration, intra-arterial administration, intramuscular administration, subcutaneous administration, intradermal, administration, intraperitoneal administration, and intravesical infusion. Topical administration include but is not limited to epicutaneous administration, inhalational administration (e.g. in asthma medications), enema, eye drops (e.g. onto the conjunctiva), ear drops, intranasal route (e.g. decongestant nasal sprays), and vaginal administration.

Similarly, the amount of pharmaceutical composition given to individuals suffering from an inflammatory disease such as, but not limited to, Crohn's disease and ulcerative colitis, asthma, dermatitis, arthritis, myasthenia gravis, Grave's disease, multiple sclerosis, or psoriasis, can be determined by the skilled person experimentally.

Exemplary incubation of an antigen presenting cell with a T cell can be performed in vitro by mixing a cell culture comprising the antigen presenting cell with a cell culture comprising the T cell, by adding a purified antigen presenting cell to a culture of T cells, or by adding a purified T cell to a culture of antigen presenting cells. Additional exemplary incubation between a T cell and an antigen presenting cell in vivo comprise transplanting antigen presenting cell in a into a tissue of an individual, the tissue comprising T cell, or transplanting T cell into a tissue of an individual the tissue comprising antigen presenting cell. In an embodiment, the individual is a transgenic animal other than humans genetically modified to express a labeled inflammatory or an anti inflammatory biomarker.

Additional procedures and techniques suitable for performing contacting between a substance and a T cell or antigen presenting cell and incubation between an antigen presenting cell and a T cell in vitro or in vivo can be identified by a skilled person upon reading of the present disclosure.

In methods and systems herein described, detection of the expression of an inflammatory or an anti-inflammatory biomarker can be performed in vitro and in vivo by techniques identifiable by a skilled person which comprise use of labeled molecules, including labeled biomarkers or labeled molecule specific for the biomarker or molecule associated thereto.

The term "detect" or "detection" as used herein indicates the determination of the existence, presence or fact of an analyte or related signal in a limited portion of space, including but not limited to a sample, a reaction mixture, a molecular complex and a substrate. A detection is "quantitative" when it refers, relates to, or involves the measurement of quantity or amount of the analyte or related signal (also referred as quantitation), which includes but is not limited to any analysis designed to determine the amounts or proportions of the analyte or related signal. A detection is "qualitative" when it refers, relates to, or involves identification of a quality or kind of the analyte or related signal in terms of relative abundance to another analyte or related signal, which is not quantified.

The terms "label" and "labeled molecule" or a used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "signal" or "labeling signal" as used herein indicates the signal emitted from the label that allows detection of the label, including but not limited to radioactivity, fluorescence, chemiluminescence, production of a compound in outcome of an enzymatic reaction and the like.

Detection can be performed by detecting levels of expression of the biomarker, a precursor or analog thereof, and/or of an analyte associated thereto. The wording "associated to" as used herein with reference to two items indicates a relation between the two items such that the occurrence of a first item is accompanied by the occurrence of the second item, which includes but is not limited to a cause-effect relation and sign/symptoms-disease relation. In particular, the detection can be performed qualitatively or quantitatively and can involve detection of molecules such as RNA, protein, their precursors, differing types (i.e. mRNA, tRNA, and rRNA) and/or degradation products, and/or detection or measurable properties associated thereof. Techniques and procedures to perform detection are identifiable by a skilled person upon reading of the present disclosure.

Exemplary methods for detection of a biomarker expression comprise methods known to a skilled person including but not limited to ELISA, Q-PCR and intracellular cytokine staining detected by FACS. In some embodiments, expression of a biomarker can be detected via fluorescent based readouts on a cell culture performed using an antibody specific for the biomarker or molecule associated thereto, labeled with fluorophore, which includes, but not exhaustively, small molecular dyes, protein chromophores, quantum dots, and gold nanoparticles. In an embodiment expression of a biomarker can be detected by detecting expression of a label under the transcriptional control of a biomarker promoter in vivo (e.g., in an animal tissue) or in vitro (e.g. in a cell culture). In some of those embodiments the biomarker can be in particular IL-10 or Foxp3. Additional techniques are identifiable by a skilled person upon reading of the present disclosure and will not be further discussed in detail.

In methods and systems herein described an anti-inflammatory ability of the candidate bacterial substance can be determined through detection of an increase of expression of the one or more anti-inflammatory biomarkers or a decrease of the expression of the one or more inflammatory biomarkers following the contacting and/or the incubating. Determining increase and/or decrease of a biomarker expression can be performed by comparing the detected expression of the biomarker following the contacting and/or incubating, with a predetermined detected expression of the same biomarker in absence of contacting and/or incubating. Determining increase and/or decrease of a biomarker expression can be performed by comparing the detected expression marker with the detected expression of the same biomarker in a control cell in absence of contacting and/or incubating.

Reference is made to the Examples section wherein increase in expression of the anti-inflammatory biomarkers IL-10, Foxp3, TGFβ1, TGF-β2, perforin and granzyme B and decrease of expression in inflammatory biomarkers TNF-α r IL-17A are associated with the mechanism of action of *Bacteroides fragilis* supporting association between the above expression pattern and the biological activities of *Bacteroides fragilis*, with particular reference to anti-inflammatory abilities. The anti-inflammatory abilities of *Bacteroides* fragilis are identifiable by a skilled person and described in various publications and patent including but not limited to U.S. Pat. Nos. 5,679,654, 7,083,777, US2004092433, WO07092451 and WO2009062132, each of which is herein incorporated by reference in its entirety. A skilled person will understand that the specific anti-inflammatory ability of the candidate bacterial substance will be possibly determined based on further determination of the specific set of cytokines produced and cells activated by the candidate bacterial substance identified by methods herein described.

In an embodiment, detection of an increase in expression of the anti-inflammatory or detection of a decrease in expression of an inflammatory biomarker indicates the ability of a substance to induce anti-inflammatory molecules such as IL-10, Foxp3, TGFβ1 or TGF-β2, perforin and granzyme B or a combination thereof, or suppress inflammatory cytokines such as IFNγ, IFNα, IFNα, IL-1, IL-4, IL-5, IL-6, IL-8, IL-9, IL-13, IL-21, IL-22, IL-23, IL-17 or TNFα or a combination thereof.

In an embodiment, the method comprises contacting a candidate bacterial substance in vitro and/or in vivo with a T cell alone or in presence of an antigen presenting cell, and detecting expression of at least one anti inflammatory biomarker selected from the group consisting of IL-10, Foxp3, TGFβ1, TGFβ2, perforin and granzyme B, wherein an increase of the expression of the anti-inflammatory biomarker following the contacting indicates an anti inflammatory ability of the candidate bacterial substance. In particular, in some of those embodiments, expression of IL-10, TGFβ1, TGFβ2, perforin and/or granzyme B can be performed on Foxp3 expressing T cell, and more particularly Foxp3 expressing Treg cell.

In an embodiment, the method comprises contacting a candidate bacterial substance with an antigen presenting cell, and incubating the antigen presenting cell with a T cell following the contacting. The method further comprises detecting the expression of at least one anti-inflammatory biomarker selected from the group consisting of Foxp3, IL-10, TGFβ1, TGFβ2, TGFβ2, Perforin and Granzyme B, wherein detection of an increase of the biomarker expression following the incubating indicates an anti-inflammatory ability of the candidate substance. In particular, in some of those embodiments, expression of IL-10, perforin and/or granzyme B can be performed on Foxp3 expressing T cell, and more particularly Foxp3 expressing Treg cell.

In an embodiment, the method comprises contacting a candidate bacterial substance with a T cell alone or in presence of an antigen presenting cell, and detecting expression of at least one inflammatory biomarker selected from the group consisting of IL-17 and TNFα, wherein a decrease of the expression of the inflammatory biomarker following the contacting indicates an anti-inflammatory ability of the candidate bacterial substance.

In an embodiment, the method comprises contacting a candidate bacterial substance with an antigen presenting cell, and incubating the antigen presenting cell with a T cell following the contacting. The method further comprises detecting the expression of at least one inflammatory biomarker selected from the group consisting of IL-17 and TNFα, wherein a decrease of the expression of the inflammatory biomarker following the contacting indicates an anti-inflammatory ability of the candidate bacterial substance.

In an embodiment, the candidate bacterial substance comprises bacteria in a pure pool. In other embodiments, the candidate bacterial substance comprises bacteria in a mixed pool. The bacteria can be live bacteria, dead bacteria, extracts or products isolated from bacteria, or combinations of each. The bacteria may also be from laboratory strains, isolates from repositories such as ATCC, isolates from animals, isolates from humans, or combinations of each.

In an embodiment, the isolate from animals is isolated from feces. The isolate can also come from intestinal contents or combinations of feces and other intestinal contents. In one embodiment, the isolate from humans is isolated from feces. The isolate can also come from intestinal contents or combinations of feces and other intestinal contents.

In an embodiment, the method comprises treating a transgenic marker non-human animal and in particular a transgenic marker mammal such as a mouse or a rat, with a candidate substance, the transgenic non-human marker animal genetically modified to express a labeled anti-inflammatory or inflammatory biomarker selected from the group consisting of IL-10 and Foxp3 but also perforin and granzyme B, IL17 and TNFα; and detecting biomarker expression in the transgenic marker animal following the treating.

In particular, in one embodiment the aforementioned transgenic non-human animal models can be treated either orally or intravenously with the substance, or permanently colonized with live bacteria by oral gavage and the amount of biomarker expression Foxp3 or IL-10 expression will be monitored in the various compartments of the mouse including the spleen, mesenteric lymph nodes, small and large intestine, lungs, pancreas, and bone marrow as a measure of the immunomodulatory ability of the substance.

In one embodiment dendritic cells, T cells, T regulatory, B cells or macrophages can be purified or differentiated from mice where expression of IL-10 (or Foxp3 in the case of T cell analysis) is marked by the fluorophore Green fluorescent protein (GFP). In those embodiments, the candidate bacterial substance is contacted with one of the aforementioned cell types and the amount of GFP expression will be determined indicating the immunomodulatory ability of the substance being tested. Alternatively, dendritic cells or other antigen presenting cells can be incubated with the substance, the substance can be washed off and the dendritic cells can be subsequently incubated with T cells to determine the ability of the dendritic cells to elicit immunomodulatory activity from the T cell. GFP expression can be determined using fluorescent activated cell sorting (FACS) or a microplate reader.

In an embodiment, a T cell, antigen presenting cell, and reagents for detection of at least one of one or more anti-inflammatory biomarkers selected from the group consisting of IL-10, Foxp3, TGFβ2, Perforin and Granzyme B and one or more labeled inflammatory biomarker selected from the group consisting of IL-17 and TNFα, an be comprised in a system for identifying a bacterial substance having immunomodulatory ability according to methods herein described.

In an embodiment, the system comprises: dendritic cell, T cell, T regulatory, B cells and/or macrophages that, in some embodiments, can be purified or differentiated from mice where expression of IL-10 (or Foxp3 in the case of T cell analysis) is marked by the fluorophore Green fluorescent protein (GFP).

The systems can be provided in the form of kits of parts. In a kit of parts, the multi-ligand capture agent and other reagents to perform the method can be comprised in the kit independently. The antigen presenting cell, the T cell and the reagents can be included in one or more compositions, and each cell and reagent can be in a composition together with a suitable vehicle.

Additional components can include labeled molecules and in particular, labeled capture agents specific for an anti-inflammatory or an inflammatory biomarker or a molecule associated to the expression thereof, a microfluidic chip, reference standards, and additional components identifiable by a skilled person upon reading of the present disclosure.

Further details concerning the identification of the suitable carrier agent or auxiliary agent of the compositions, and generally manufacturing and packaging of the kit, can be identified by the person skilled in the art upon reading of the present disclosure.

EXAMPLES

The vesicles, compositions and related methods and systems herein described are further illustrated in the following examples, which are provided by way of illustration and are not intended to be limiting.

In particular, the following examples illustrate exemplary cell cultures, methods for contacting OMVs comprising PSA (or PSA ligand) with cells and detecting expression of a biomarker. A person skilled in the art will appreciate the applicability of the features described in detail for OMVs and PSA and *Bacteroides fragilis* for additional vesicles and delivery of substances additional to PSA in OMVs or other vesicles according to the present disclosure.

The following material and methods were used for all the methods and systems for detection of immunomodulatory substances exemplified herein.

Bacterial strains and culture conditions and mice *B. fragilis* strain NCTC 9343 was obtained from the American Type Culture Collection, its isogenic PSA deletion mutant and mpi44 mutant (produces only PSA but not other polysaccharides) has been described (M. J. Coyne, A. O. Tzianabos, B. C. Mallory, V. J. Carey, D. L. Kasper and L. E. Comstock, (2001) Polysaccharide biosynthesis locus required for virulence of *Bacteroides fragilis*, Infect. Immun. 69: 4342-4350.) Bacteria were grown either in a rich medium containing 37 g BHI (BD #237200), 0.5 µg/ml Hemin (Sigma H5533), and 0.5 µg/ml Vitamin K (Sigma V3501) in 1 L ddH2O or a customized minimum medium (MM), which contained 8 g Glucose, 1% FBS, 0.5 µg/ml Hemin, and 0.5 µg/ml Vitamin K in 1 L of RPMI (Invitrogen SKU#11835-030). SPF mice of strains C57BL/6 and Balb/c were purchased from Taconic Farms (Germantown, N.Y.). TLR2 knockout mice and IL-10 knockout mice were purchased from Jackson laboratories IL-10GFP mice were procured from the laboratory of Christopher Karp from Cinncinati Children's medical hospital, and, Foxp3GFP mice were a given by the laboratory of Talal Chatila from the University of California Los Angeles.

Isolation of EDL-enriched bacterial population. Percoll (GE Healthcare #17-0891-01) discontinuous density-gradient centrifugation was used for EDL isolation of both wild-type *B. fragilis* and *B. fragilis* ΔPSA (Patrick S, Reid R I. (1983) Separation of capsulate and non-capsulate *Bacteriodes fragilis* on a discontinuous density gradient. J Med Microbiol. 16(2): 239-41.) Briefly, a 20%, 40%, 60%, 80% Percoll gradient (diluted with PBS) was created in a 14 ml test tube (2 ml for each layer). Then *B. fragilis* culture resuspended in PBS was carefully added on top of the 20% Percoll layer. Subsequently, the gradient was centrifuged at 800 g for 20 min at RT. EDL-enriched bacteria can be recovered from the 40%-60% interface of the gradient after the separation.

OMV purification and labeling. This method is adapted from a previously described protocol for the preparation of OMVs from *E. coli* (Amanda L. Horstman and Meta J. Kuehn. (2000) Enterotoxigenic *Escherichia coli* secretes active heat-labile enterotoxin via outer membrane vesicles. J Biol Chem. 275: 12489-12496.) Briefly, EDL-enriched *B. fragilis* was grown in customized MM. OMVs were recovered from the bacteria-free supernatant of the culture by centrifugation at 40,000 g for 2 hrs at 4 C and further washed twice with PBS and filtered through 0.45 µm spin columns (Millipore #20-218). Total protein concentration of the purified OMVs was determined by Bradford assay (Biorad #500-0205). FITC-labeled OMVs were prepared as previously described (Nicole C. Kesty and Meta J. Keuhn. (2004) Incorporation of heterologous outer membrane and periplasmic proteins into *Escherichia coli* outer membrane vesicles. J Biol Chem. 279: 2069-2076). Briefly, OMVs were incubated in the staining buffer (1 mg/ml FITC (Thermo Scientific #46424), 100 mM NaCl, 50 mM Na2CO3, pH 9.2) for 1 hr at RT. Labeled OMVs were collected by centrifugation at 40,000 g for 30 min at 4 C and washed twice with PBS+200 mM NaCl.

Electron microscopy of bacterial ultrathin section. Ultrathin sections of EDL-enriched *B. fragilis* were prepared as previously described (Patrick S, McKenna J P, O'Hagan S, Dermott E. (1996) A comparison of the haemagglutinating and enzymic activities of *Bacteroides fragilis* whole cells and outer membrane vesicles. Microb Pathog. 20(4):191-202.) Briefly, samples were fixed in 2.5% (v/v) glutaraldehyde (Sigma, G5882) in cacodylate buffer overnight at 4° C., followed by further fixation in osmium tetroxide (1%, w/v) for 3 hrs at RT in the dark. Ruthenium Red (1 mg/ml, Sigma R2751) was included in both of the fixation processes. Then fixed samples were embedded in epoxy resin after dehydration in a graded series of alcohols. Ultrathin sections (100-200 nm) were cut and negatively stained with 2% uranyl acetate and lead citrate on formvar/carbon coated copper grids (EMS #FCF200-Cu) before visualization by TEM.

Immunogold labeling of purified OMVs. This method was adapted from a previously described protocol (Patrick S, McKenna JP, O'Hagan S, Dermott E. (1996) A comparison of the haemagglutinating and enzymic activities of *Bacteroides fragilis* whole cells and outer membrane vesicles. Microb Pathog. 20(4):191-202.) Briefly, a tiny drop of purified OMV was applied to formvar/carbon coated gold grids (EMS #FF200-Au) and air-dried. Immunogold labeling was performed at RT by floating these grids with "OMVs"-side down on a series of small drops of antibody and wash solutions. Particularly, samples were blocked in 10% FBS for 10 min after 5 min incubation in 0.12% glycine. After blocking, samples were further incubated with antibody against PSA diluted in 10% FBS for 20 min, followed by 5 washes×3 min with PBS. Subsequently, secondary antibody-IgG conjugated with 5 nm gold (kind gift from Dr. Paul Webster, House Ear Institute, Los Angeles) was applied to the samples for 20 min, followed again by 5 washes×4 min with PBS. After labeling, samples were fixed in 1% glutaraldehyde for 5 min and washed extensively by transferring grids to drops of PBS 4×1 min and H2O 4×1 min. Contrast staining was performed by placing the grids on drops of 3-5% uranyl acetate in 2% methylcellulose for 10 min on ice. Finally, grids were removed from the staining solution by a wire loop and air-dried. Samples covered by a thin film of methylcellulose were removed from loop and used for visualization by transmission electron microscopy (TEM).

Glycoprotein assay. PSA purified from whole cell extracts or OMVs (from *B. fragilis* mutant mpi44) were subjected to SDS-PAGE and the gel was stained subsequently by glycoprotein staining kit (G bioscience #786-254) to show the presence of PSA.

Chemical (TNBS)-induced experimental colitis. This protocol is adapted from a previously described method (Scheiffele and Fuss. (2001) Induction of TNBS colitis in mice. Current Protocols in Immunology.15.19.1-15.19.14.) Briefly, wild-type (Balb/c) male mice were orally treated with PBS, WT-OMV (5 µg) or ΔPSA-OMV (5 µg) every other day for a week before TNBS administration. The treated mice were anesthetized with isofluorene and rectal administration of 2% TNBS (in 50% EtOH, Sigma P2297) was applied through a 3.5 F catheter (Instech Solomon; SIL-C35). Oral treatment continued for another two times after TNBS administration and mice were analyzed 1-2 days after the last treatment.

In a prophetic example, the same mice may be treated with the TNBS—as indicated above—prior to orally treating the mice with PBS, WT-OMV (5 µg) or ΔPSA-OMV (5 µg) every other day for a week before TNBS administration. The treated mice would then be anesthetized with isofluorene and rectally administered with 2% TNBS (in 50% EtOH, Sigma P2297) as applied through a 3.5 F catheter (Instech Solomon; SIL-C35). Oral treatment would be continued for another two times after TNBS administration and then mice were analyzed 1-2 days after the last treatment. We expect that using this protocol, the degree of colitis in these mice would be improved, reduced or cured. This expectation is based on the fact that our previous studies using PSA alone (Round et al. 2010) both prior to and after TNBS treatment have both prevented and reduced colitis, respectively; and the fact that some of our present results show that our OMV effect on these mice is PSA dose dependent.

Tissue pathology analysis Mouse colons were fixed in neutral buffered 10% formalin (ScyTek Laboratories CAS#50-00-0) and processed by Pacific Pathology for H & E staining. Colitis scores for each colon section were evaluated in a blinded fashion by a pathologist (Dr. Gregory Lawson, David Geffen School of Medicine, UCLA, Los Angeles). Histology images were taken using light microscopy (Zeiss) at 20× magnification.

Quantitative real-time PCR RNA was collected either from mouse tissues using Trizol (Invitrogen #15596-018) or from purified cells using RNeasy Mini Kit (Qiagen #74104). iSCRIPT cDNA synthesis kit (BioRad #170-8890) was used for conversion of cDNA and IQ SYBR Green supermix (BioRad #172-8882) was used for real-time PCR. Primers used in this study are: TNF (F-5'ACG GCA TGG ATC TCA AAG AC 3' (SEQ ID NO:1); R-5' GTG GGT GAG GAG CAC GTA GT 3') (SEQ ID NO 2); IL-17 (F-5' TTA AGG TTC TCT CCT CTG AA 3'(SEQ ID NO:3); R-5' TAG GGA GCT AAA TTA TCC AA 3') (SEQ ID NO: 4) IL-10 (F-5' GGT TGC CAA GCC TTA TCG GA 3' (SEQ ID NO:5); R-5' ACC TGC TCC ACT GCT TGC T 3') (SEQ ID NO: 6) Foxp3 (F-5' GCA ATA GTT CCT TCC CAG AGT TCT 3'(SEQ ID NO: 7); R-5' GGA TGG CCC ATC GGA TAA G 3' (SEQ ID NO: 8)) actin (F-5' TTC GTT GCC GGT CCA CA 3'(SEQ ID NO:9); R-5' ACC AGC GCA GCG ATA TCG-3' (SEQ ID NO: 10)).

Fluorescent microscopy In vitro differentiated BMDCs were plated into Lab-Tek II 8-well chamber slide (Nunc #154534) at 50,000 cells/well. FITC labeled OMVs were added into the cell culture at 10 µg/ml. After 2 hrs incubation, cells were fixed in 4% PFA for 20 min at RT. After 3 washes×5 min with PBS, cell membrane was stained with 1 µg/ml tetramethylrhodamine conjugate of WGA (Invitrogen W849) for 1 hr at 4 C. And ProLong Gold anti-fade reagent (P36930) was applied to the sample after extensive washes following membrane staining. Fluorescent images were taken using LSM 510 microscope and Plan-Neofluar 63×/1.25 oil objective.

Flow cytometry and staining BMDCs from OMV uptake assay or activation assay were collected and blocked in 5% mouse serum for 30 min on ice. After blocking, cells were stained with anti-CD11c-APC, anti-MHCII-FITC or anti-CD86-PE (ebioscience) for 30 min on ice and washed 2× with FACS buffer (HBSS (no Ca2+/Mg2+), 1% FBS, 2 mM EDTA, 10 mM HEPES) at 4° C. before flow cytometry analysis. Similarly, cells from in vitro BMDC-T cell co-culture were blocked, and stained with anti-CD4-APC/anti-CD25-PE the same way except that the cells were re-stimulated using PMA/Ionomycin for 4-4.5 hrs before collecting. All flow cytometry was done with BD FACSCalibur and results were analyzed using FlowJo.

In vitro BMDC-T cell co-culture. Bone marrow was collected from different stains of mice and differentiated in vitro in the presence of 20 ng/ml GM-CSF (Miltenyi Biotec #9517571) for 8 days as described previously (Mazmanian, Liu, Tzianabos, and Kasper (2005) An Immunomodulatory Molecule of Symbiotic Bacteria Directs Maturation of the Host Immune System. Cell 122:1 107-118.). (Cell purity was >90%.) CD4+ splenic T cells were isolated by magnetic microbead purification (Miltenyi Biotec #130-090-860) (Cell Purity is >95%.) OMV-pulsed BMDCs (10 µl/ml OMVs, 100,000 cells/ml, 12 hrs-24 hrs) were washed with HBSS and then incubated with CD4+ T cells (1,000,000 cells/ml) in a round bottom 96 well plate with addition of 0.01 µl/ml anti-CD3 (day 0, FIG. 3c as indicated, 3d, e, f, FIG. 4a), 2 ng/ml TGFb (day 0, FIGS. 3c, d & f, FIG. 4a), and 5 ng/ml IL-2 (day 1 and day 3, all in vitro DC-T cell co-culture assays). After total 4 days of culture, supernatants were collected for ELISA (ebioscience #88-7104-77) or cells were harvested for staining and flow cytometry analysis.

In vitro suppression assay: CD4+CD25+ cells purified from BMDC (pulsed with WT-OMV or ΔPSA-OMV)-T cell co-culture were used as a source of Tregs (Miltenyi Biotec, #130-091-041). CD4 depleted mouse splenocytes treated with Mitomycin C (Sigma M4278) were used as APCs (100,000 cells/ml). CD4+CD25-T cells directly purified from mouse spleen were pulsed with CFSE for 10 min at 37° C., followed by first wash with PBS and a second wash with culture media, and used immediately (500,000 cells/ml) as responder cells (Teff). This assay was conducted in a round bottom 96 well plate with an addition of 5 µg/ml of anti-CD3 (ebioscience #16-0031-86) in 200 µl volume. Teff:Treg ratio was titrated and cells were collected after 2-3 days of culture for FACS analysis.

Statistical Analyses: Student T test and one-way ANOVA were applied for pair-wise comparisons and comparisons among >2 groups, respectively. Significant differences among groups detected by ANOVA were analyzed using Newman-Keuls test as the post-hoc test to identify groups exhibiting statistically significant differences. All error bars indicate SEM. NS: not significant; * $p<0.05$; * $p<0.01$; * $p<0.001$.

Example 1

Immunomodulatory Capsular Polysaccharide PSA is Actively Sorted Into OMVs of B. fragilis Ultrathin sections of EDL-enriched B. fragilis were prepared as described in materials and methods and imaged by transmission electron microscopy.

Figure 5:
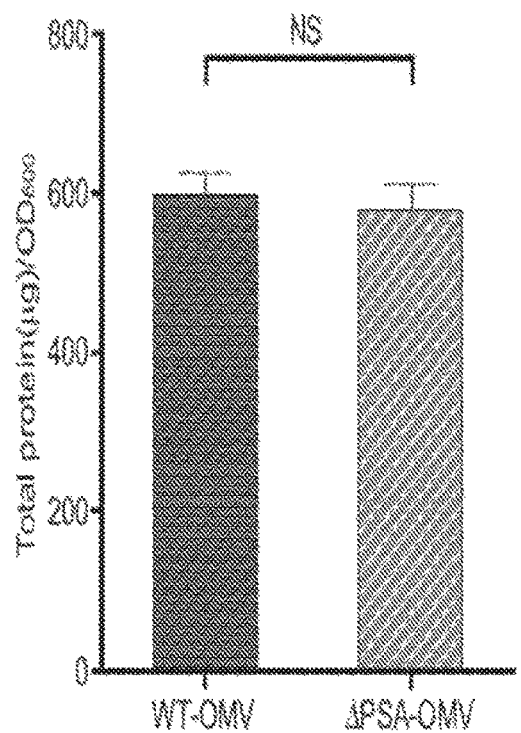
FIG. 5 shows wild-type *B. fragilis* and PSA deletional mutant *B. fragilis* produce similar amount of OMVs during in vitro culture. The amount of total protein recovered from each OMVs preparation normalized by OD600 of the culture at the time of harvest. Error bars indicate SEM. Result is shown from >10 combined experiments preformed independently. p value determined by Student's t-test. NS: not significant.

The results illustrated in FIG. 1a show that OMVs were abundantly produced by bacteria, and could be observed budding from the bacterial envelope (FIG. 1a, higher magnification). Applicants' previous studies have shown that deletion of PSA abrogates the immunomodulatory capacity of B. fragilis (Mazmanian, Liu, Tzianabos, and Kasper (2005) An Immunomodulatory Molecule of Symbiotic Bacteria Directs Maturation of the Host Immune System. Cell 122:1 107-118.) (Mazmanian, Round, and Kasper (2008) A microbial symbiosis factor prevents intestinal inflammatory disease. Nature. 453 (7195) 620-625. Electron micrographs of a PSA mutant strain (B. fragilis ΔPSA) illustrate no defect in OMV synthesis, and the size, shape and abundance of OMVs produced were indistinguishable from wild-type bacteria (FIG. 1a and FIG. 5). In particular, the results illustrated in FIG. 1a reveal that vesicles are actively budding from the surface of bacteria.

To determine if PSA is associated with OMVs of B. fragilis, purified vesicles from wild-type and ΔPSA bacteria were subjected to immunoblot analysis as described in the materials and methods section.

Figure 1B:
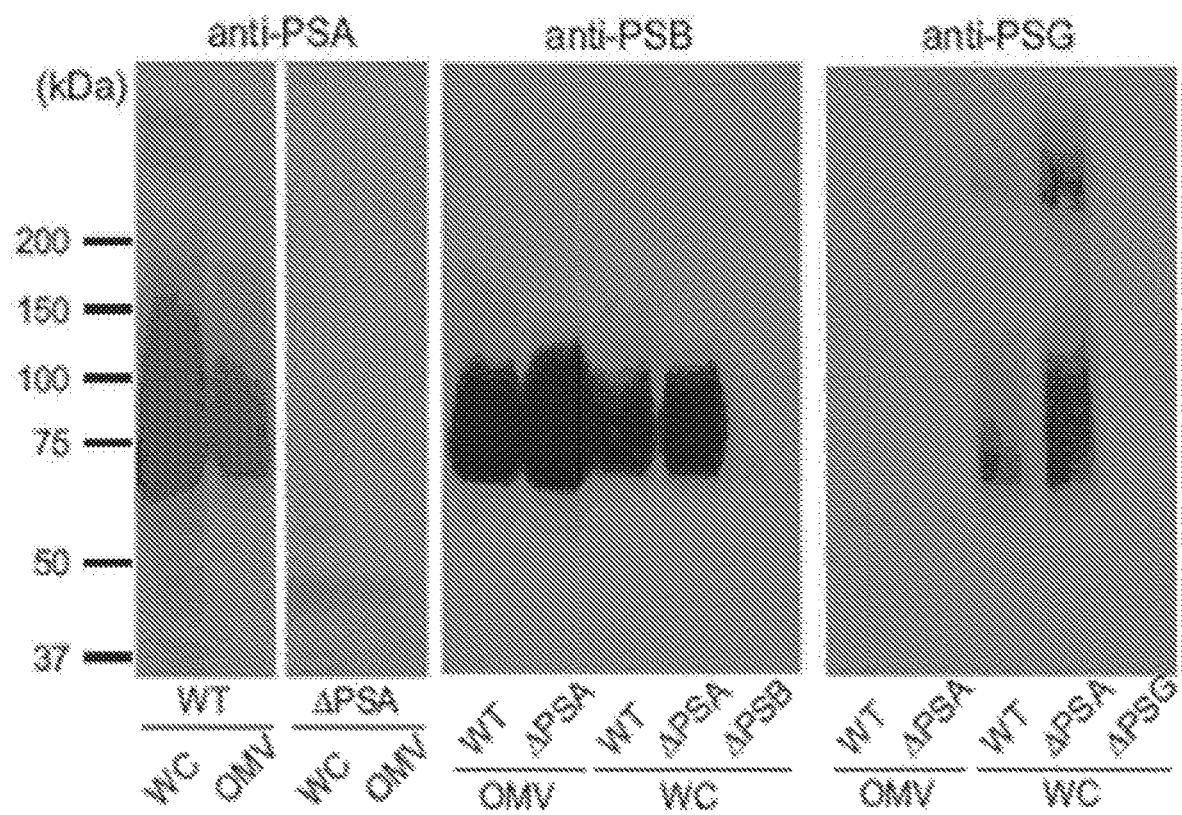

The results illustrated in FIG. 1b show that the vesicles from wild-type displayed immunoreactivity for PSA, unlike OMVs from B. fragilis ΔPSA. B. fragilis produces at least 8 distinct capsular polysaccharides which coat the surface of bacterial cells, named PSA, PSB, PSC, PSD, PSE, PSF, PSG, and PSH. While PSB was also detected in vesicle preparations, PSG was absent, demonstrating selectivity for certain polysaccharides to be packaged with OMVs (FIG. 1b). Accordingly, the results of FIG. 1b show that PSA and PSB are associated with vesicles, while PSG is only found on the bacterial surface. Deletion mutants for capsular polysaccharides confirm specificity of each anti-serum.

Figure 1C:
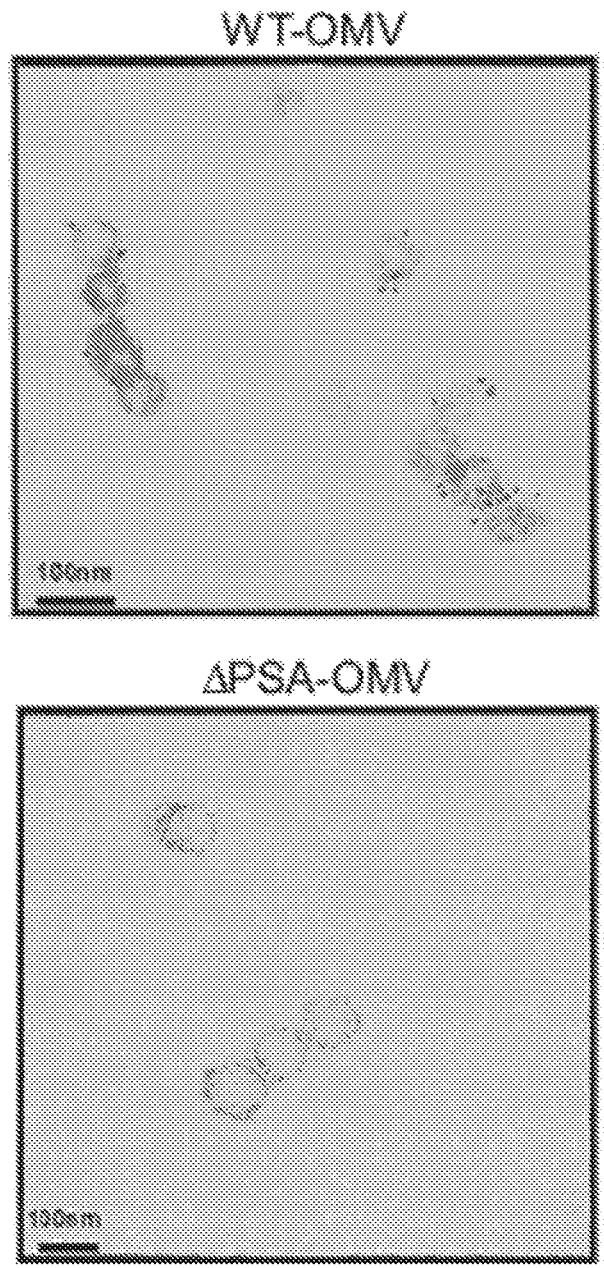
Figure 6:
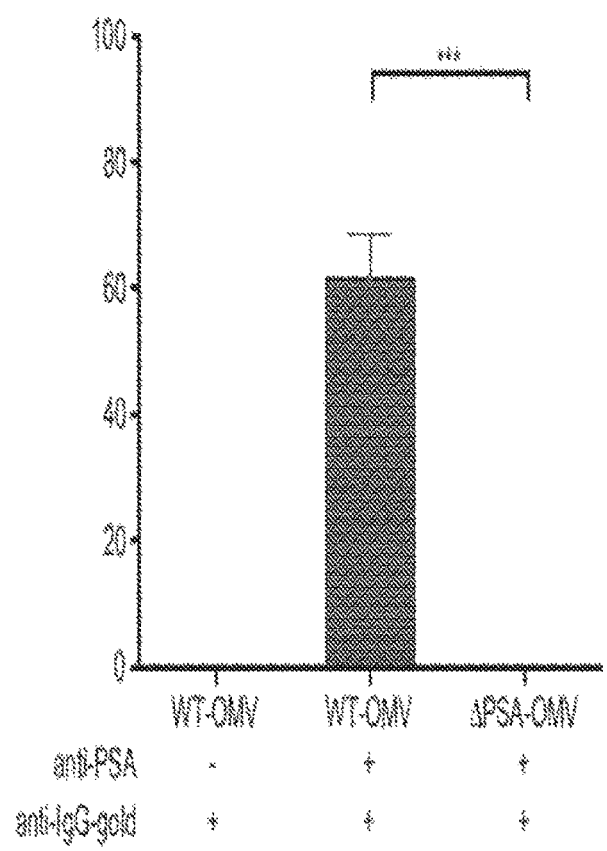
FIG. 6 shows Majority OMVs purified from wild-type *B. fragilis* contain PSA Immunogold labeling of PSA on purified OMVs shows ~60% of WT-OMVs observe among random sampling of 10 areas (1 μm×1 μm) of sample are associated with PSA, but none of ΔPSA-OMVs observed are stained positively for PSA. (Immunogold labeling of WT-OMVs with anti-IgG-gold only confirms the specificity of the labeling).

The results from immunoblot analysis were confirmed by experiments of immunogold labeling performed as described in the materials and methods section. The results of immunogold labeling of purified vesicles illustrated in FIG. 1c and confirm that PSA is physically associated with OMVs, and that the vast majority of OMVs from wild-type B. fragilis stain positively for PSA (FIG. 6). To verify that the absence of PSA did not alter the molecular composition of OMVs, a proteomic analysis was performed by mass spectrometry which revealed no major qualitative or quantitative differences in the protein composition between vesicles from wild-type or PSA-mutant bacteria (FIG. 7).

PSA is a heterogeneous polymer of repeating subunits. Size separation of PSA recovered from whole cell extracts by chromatography was performed as well as an immunoblot analysis with anti-PSA of capsular polysaccharide preparations from whole cells and purified OMVs as indicated in material and methods.

Figure 1D:
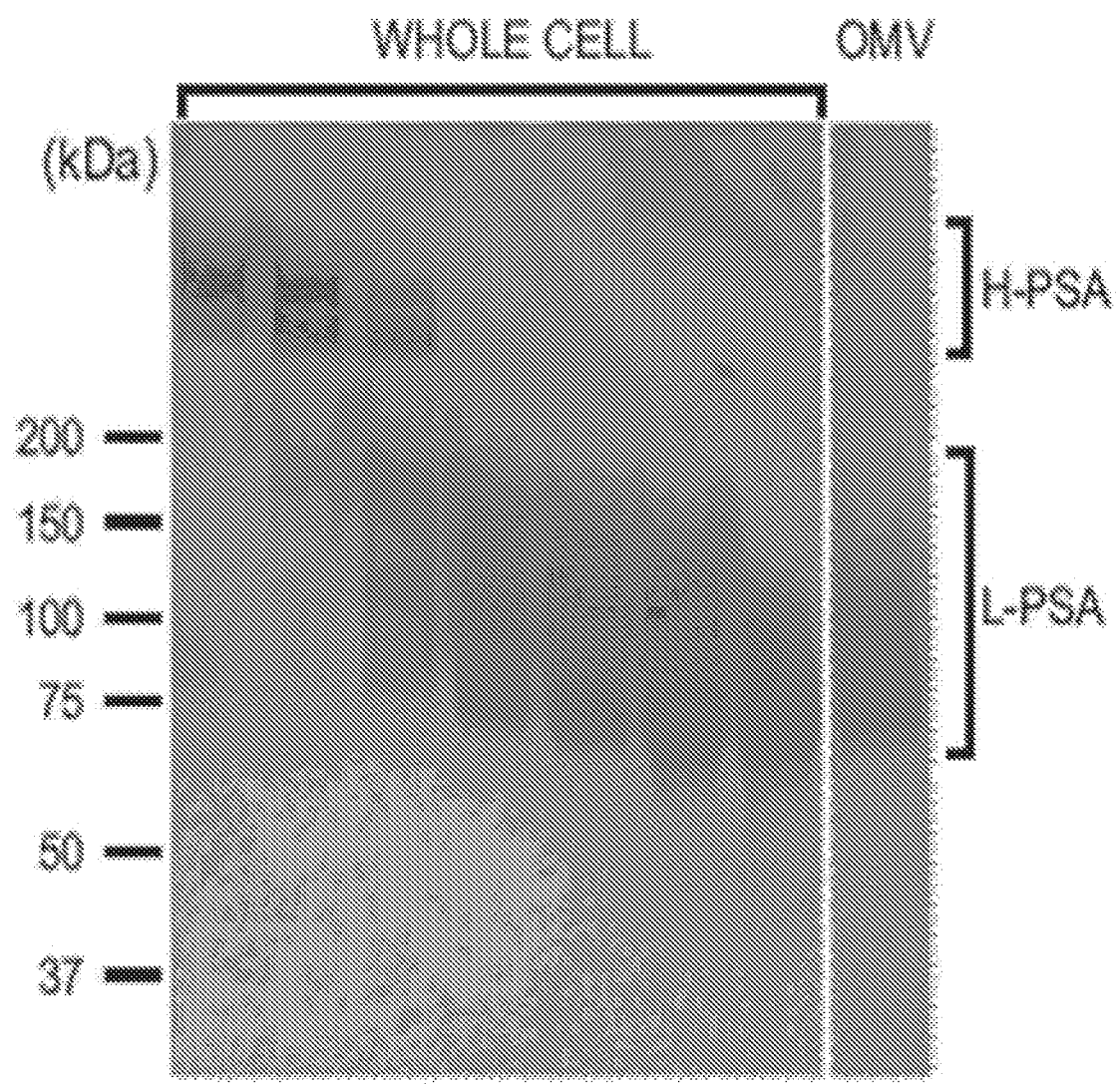

The relevant results illustrated in FIG. 1d surprisingly show that only the low molecular weight species, L-PSA, is associated with OMVs, illustrating specificity of PSA packaging into vesicles. In particular, the results of FIG. 1d show that only low molecular weight PSA (L-PSA) is packaged into vesicles unlike the high molecular weight (H-PSA) species that remains associated with the bacterial cell envelope.

Together, the above results reveal that the immunomodulatory capsular polysaccharide PSA is actively sorted into OMVs of B. fragilis.

Example 2

OMVs Protect Animals From Experimental Colitis and Intestinal Inflammation in a PSA-Dependent Manner To investigate if OMVs can ameliorate clinical symptoms of disease, mice were treated by gavage with OMVs during the induction of TNBS (2,4,6-trinitrobenzene sulfonic acid) colitis.

Figure 2A:
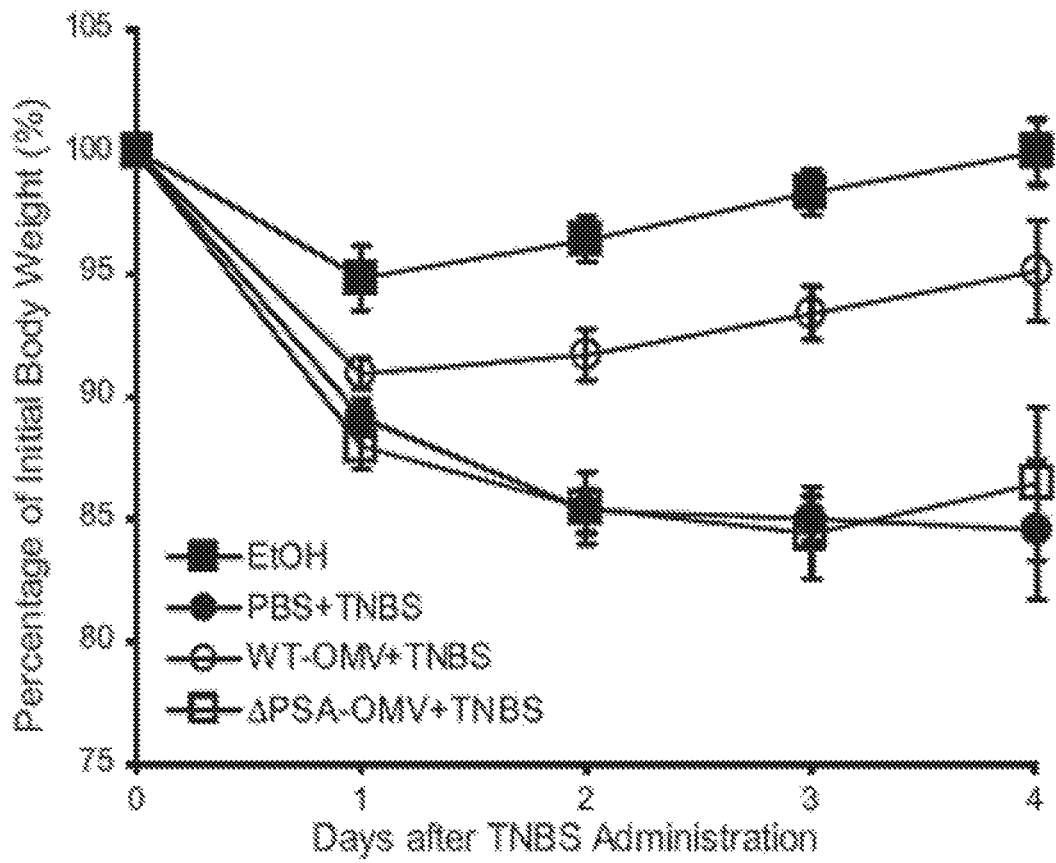

The results illustrated in FIG. 2a indicate that control animals rapidly lost weight following rectal administration of TNBS (FIG. 2a; TNBS+PBS), which did not recover compared to vehicle treated mice (FIG. 2a; ETOH+PBS). Remarkably, OMVs given orally to TNBS animals significantly protected from weight loss (FIG. 2a; TNBS+WT-OMV). Most importantly, when OMVs from B. fragilis ΔPSA were administered, weight loss was indistinguishable from TNBS animals (FIG. 2a; TNBS+ΔPSA-OMV), demonstrating that PSA is responsible for preventing wasting disease.

Our efforts to detect intact vesicles in the colon after intra-gastric gavage were confounded by observations of host-derived vesicles, even in germ-free (sterile) mice as previously reported (data not shown).

Since reduction in colon length is a hallmark of TNBS colitis detection of colon length was performed in unmanipulated colons immediately following resection from cecum to rectum and quantification of length (graph) from vehicle treated (EtOH) and TNBS groups (n=4 animals/group). In particular, measurement were performed at time of sacrifice (day 4 following disease induction).

Figure 2B:
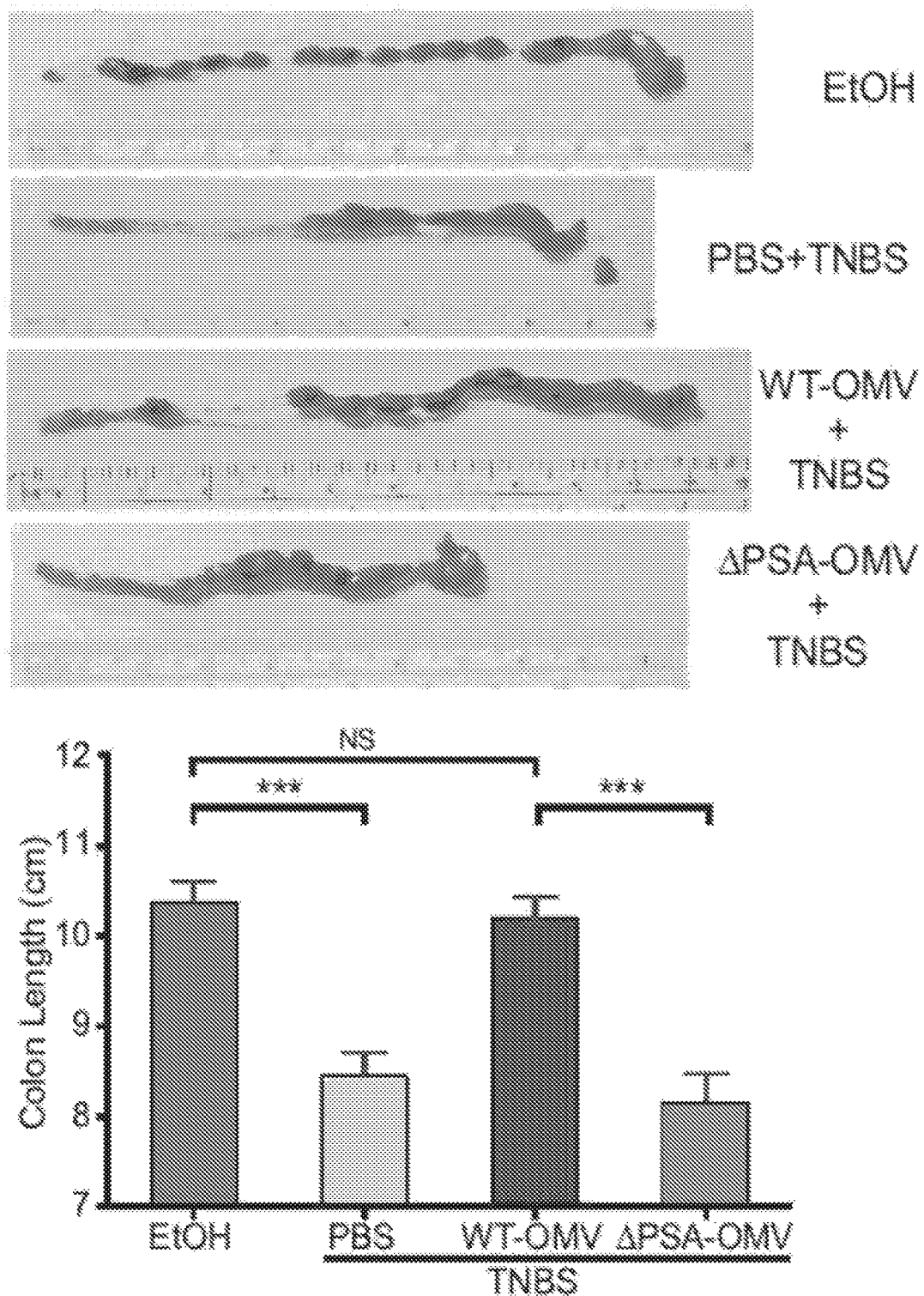

The results illustrated in FIG. 2b showed normal intestinal lengths in animals treated with PSA-containing vesicles, but not in animal treated with OMVs deficient in PSA (FIG. 2b).

Figure 2C:
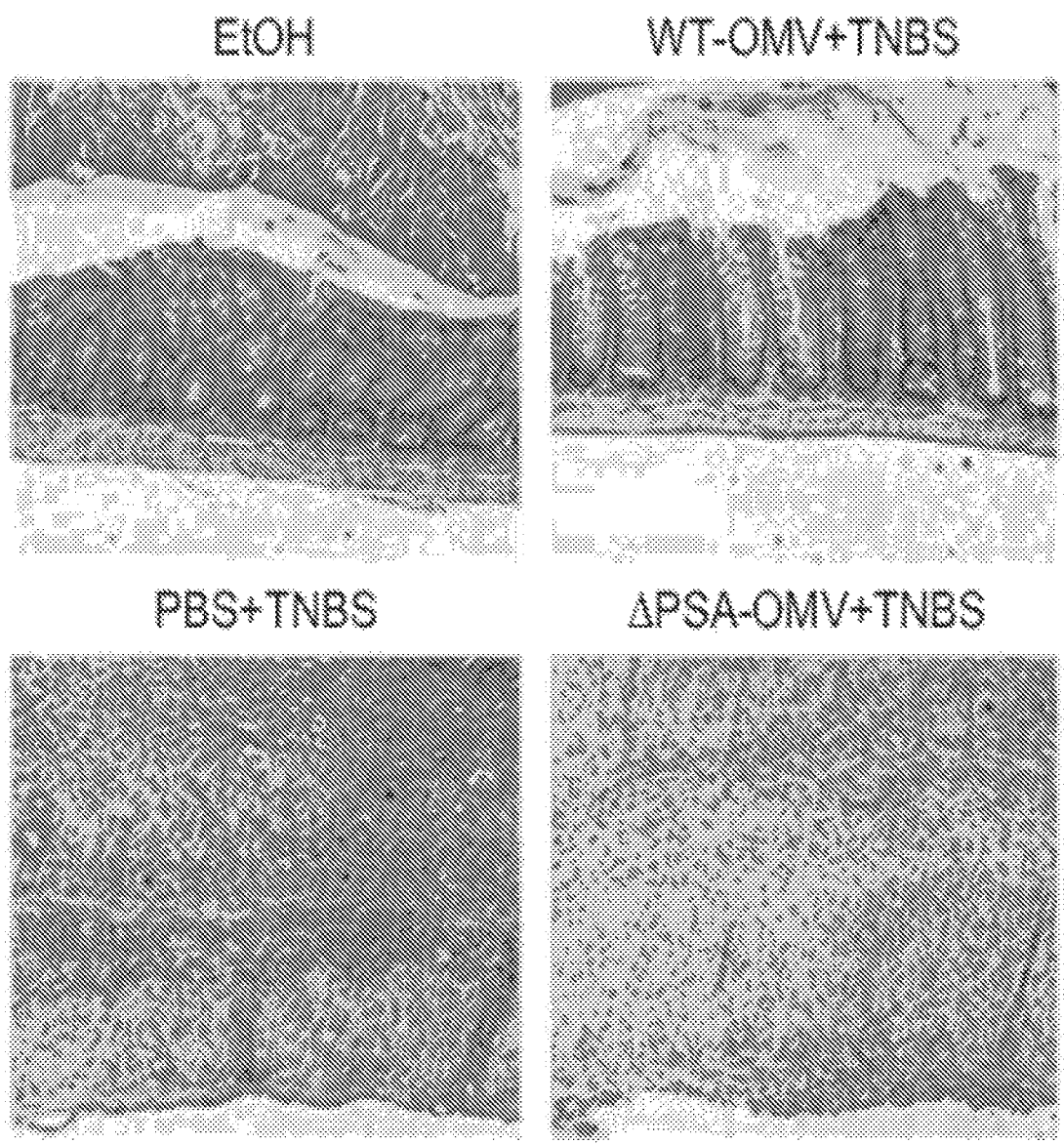

Experimental colitis results in severe pathological alterations in intestinal architecture. Accordingly, hematoxylin and eosin (H & E) stained colon sections representative of each treatment group were provided and are shown in FIG. 2c. The images of FIG. 2c show that upon histological analysis of colonic tissues, a significant disease was observed in TNBS treated animals that were ameliorated by oral administration of PSA-containing vesicles.

Figure 2D:
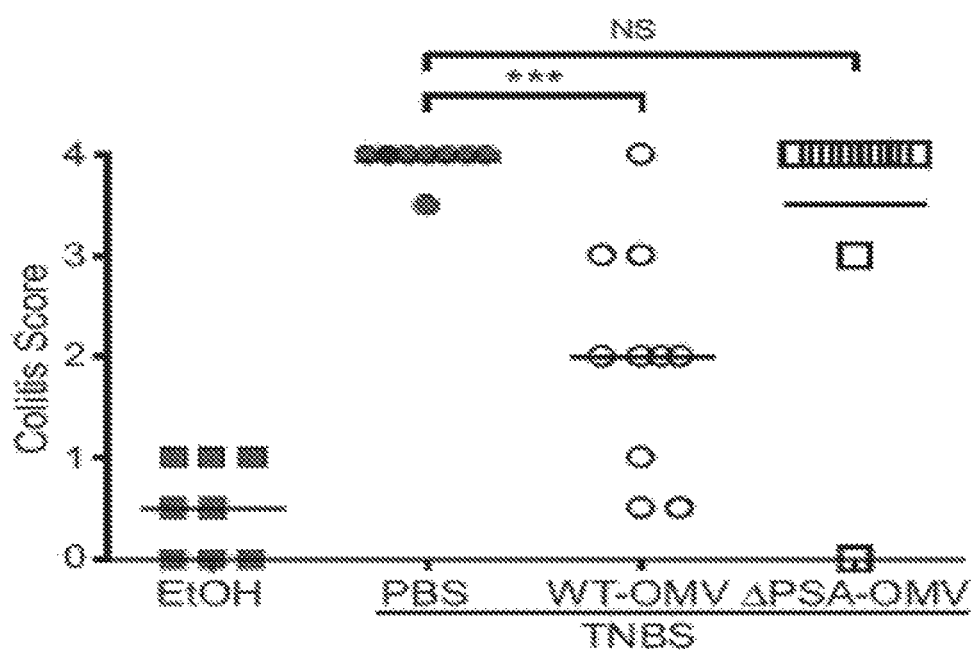

The results of FIG. 2c were confirmed by colitis scores from animals assigned by a blinded pathologist TNBS colitis manifests itself in focal lesions throughout the colon which mimic the pathology observed in Crohn's disease. To quantitatively assess disease, clinical symptoms were evaluated by a blinded pathologist using a standard scoring system (Scheiffele and Fuss. (2001) Induction of TNBS colitis in mice. Current Protocols in Immunology.15.19.1-15.19.14.) The results illustrated in FIG. 2d, indicate that while all TNBS and ΔPSA-OMV treated animals were severely affected, WT-OMVs significantly reduced disease in most animals. Animals treated with OMVs from wild-type bacteria had much fewer focal sights of pathology, and when lesions were observed, they were smaller and retained considerably normal tissue architecture compared to animals given ΔPSA-OMV.

The above results establish that PSA is required for the disease protective activity of OMVs.

Example 3

PSA Containing OMVs Inhibits TNF-α/IL-17, Enhances IL-10 Expression

The production of canonical pro- and anti-inflammatory cytokines associated with colitis was measured in mice treated as exemplified in Example 2. In particular, cytokine transcript analysis was performed by qRT-PCR from RNA recovered from whole colons or purified CD4+ T cell from mesenteric lymph nodes.

Figure 2F:
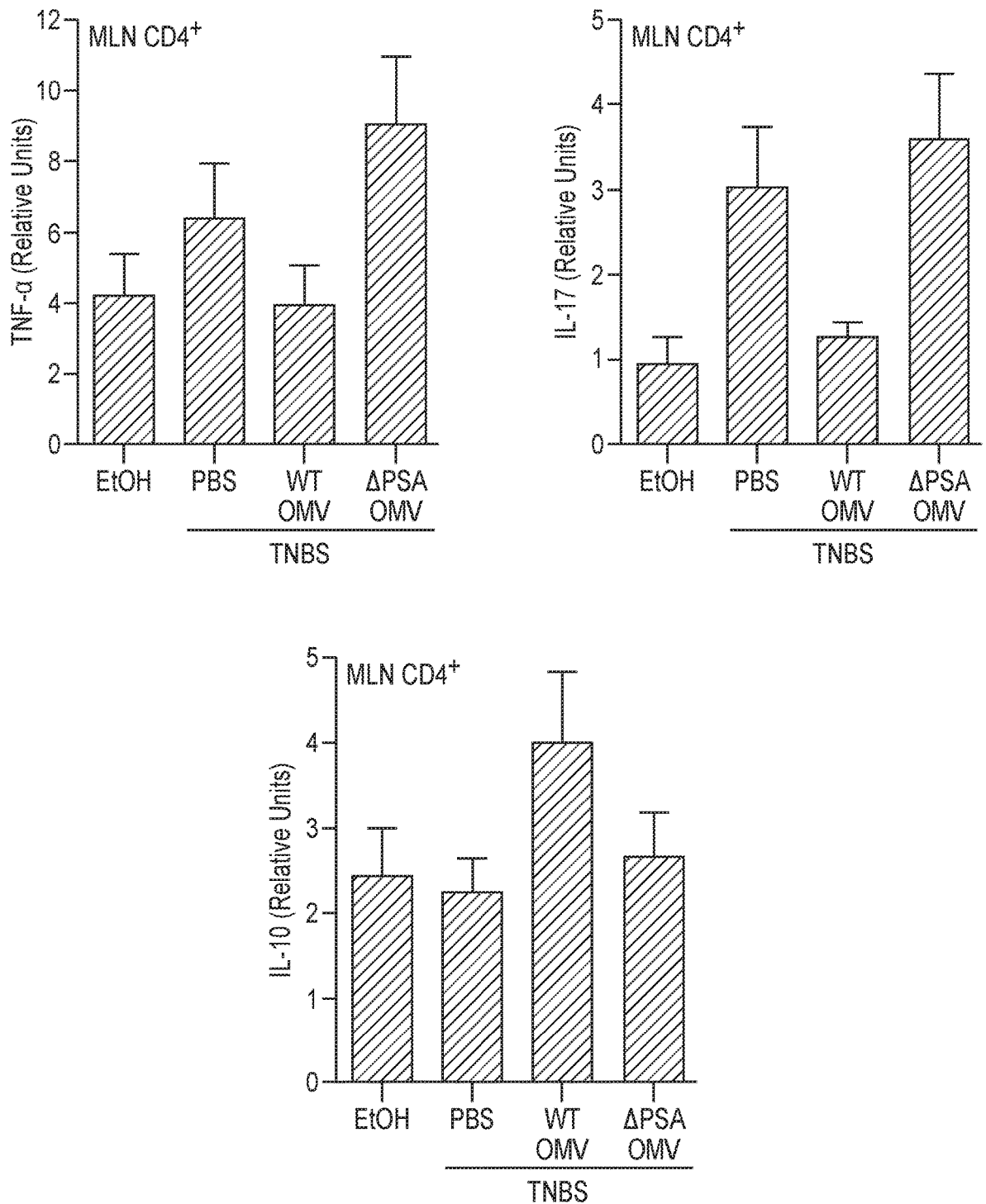

The relevant results representative of 3 independent trials are reported in FIG. 2e (whole colons) and FIG. 2f (purified CD4+ T cell from mesenteric lymph nodes). Those results show that transcript levels of pro-inflammatory biomarkers/cytokines tumor necrosis factor (TNF-α) and IL-17A were elevated in TNBS-treated animals, but reduced by OMV administration in a PSA-dependent manner (FIG. 2e). Consistent with protection from pathology, OMVs elicited the production of increased anti-inflammatory biomarkers/cytokines IL-10 levels compared to animals orally given ΔPSA-OMV (FIG. 2f). Analysis of cytokine production by purified CD4+ T cells from mesenteric lymph nodes (MLNs) confirmed that IL-10 was indeed being produced by T cells in response to PSA (FIG. 2f). Infiltration of Th17 cells, which are required for disease, were significantly reduced by OMVs, as were levels of the potent pro-inflammatory marker TNF-α (FIG. 2f). We conclude that PSA packaging into OMVs of *B. fragilis* protects animals from the pathological and immunological manifestations of experimental colitis.

Example 4

PSA Containing OMVs from *B. fragilis* Induce Dendritic Cell Responses

Dendritic cells (DCs) extend protrusions into the gut lumen and sample intestinal particles, and subsequently migrate to MLNs in order to initiate T cell reactions. Indeed, PSA administered orally to animals is associated with CD11c+ DCs in the MLN. Accordingly, Applicants sought to test whether OMVs containing PSA can also be taken up by DCs.

Figure 3A:
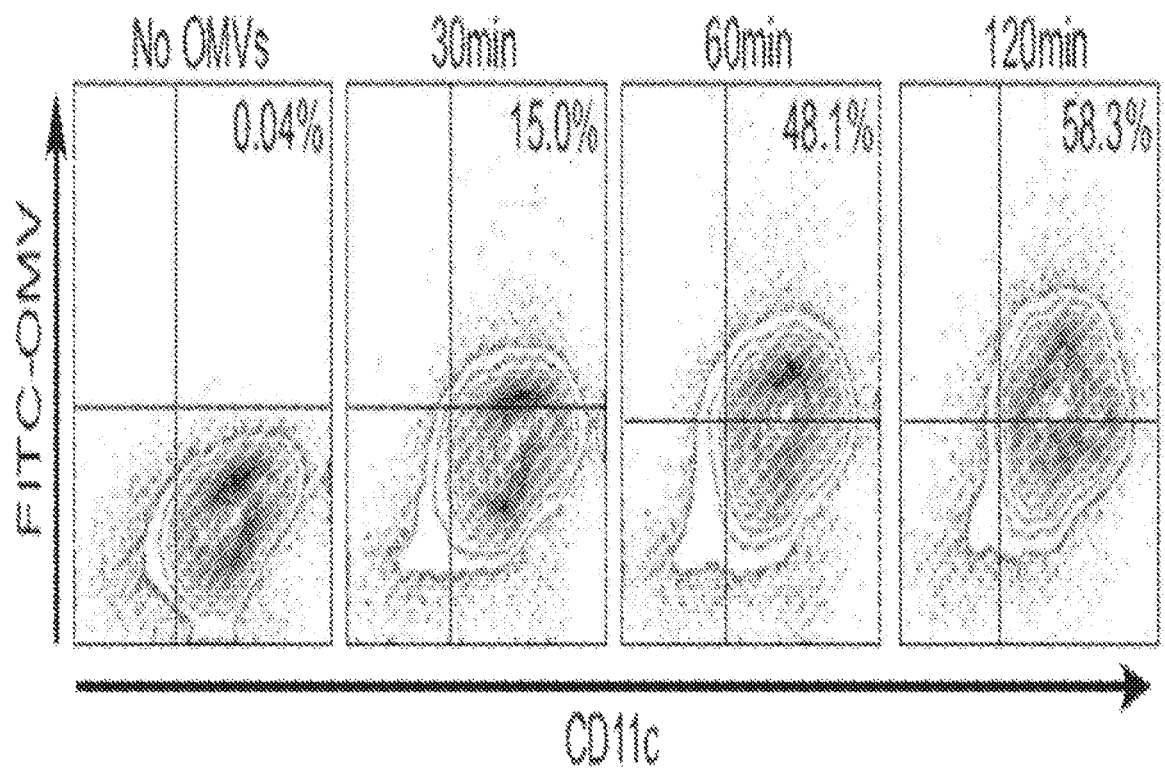
Figure 8:
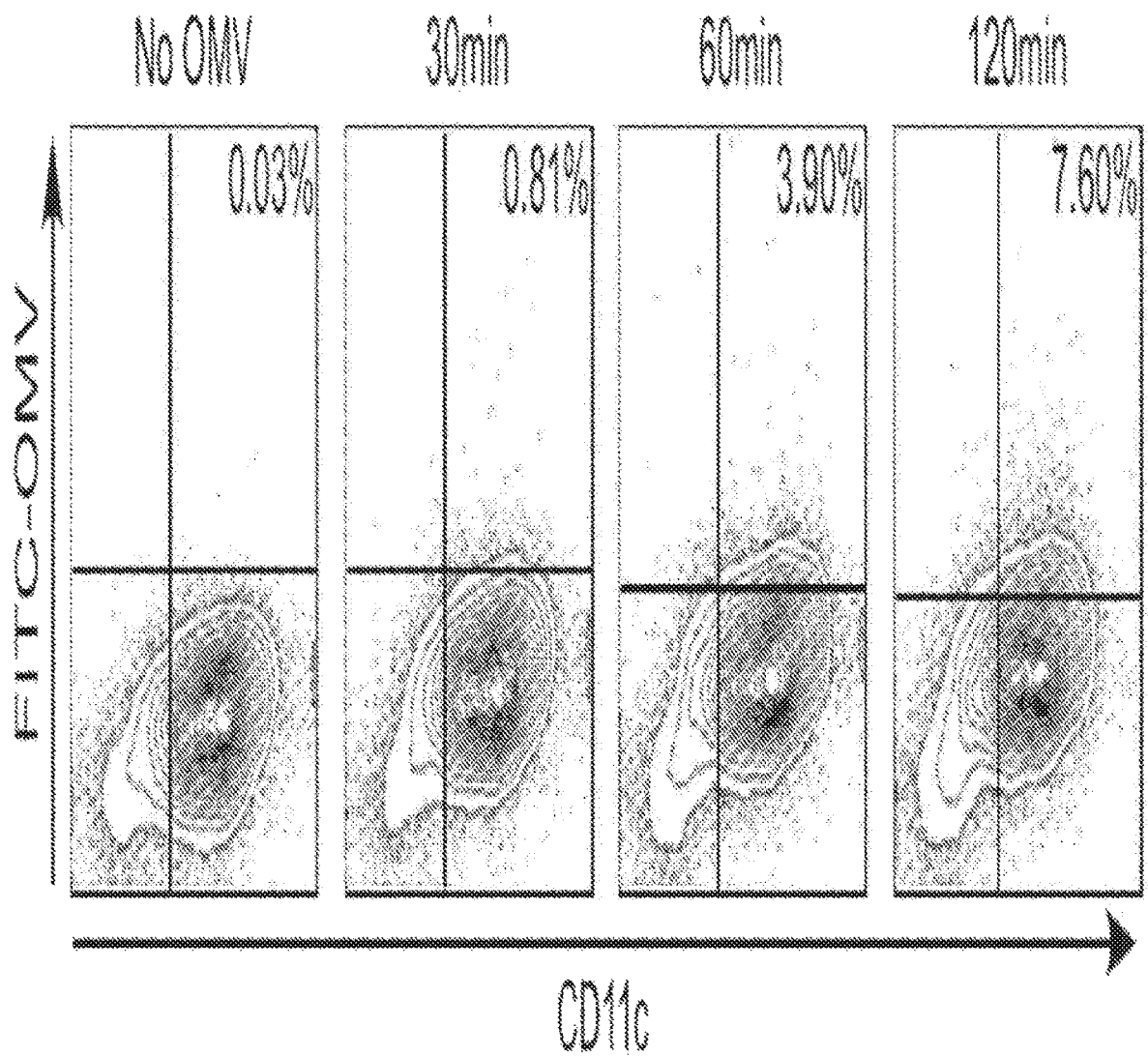
FIG. 8 shows actin polymerization is required for OMV uptake by DCs. Flow cytometry analysis of OMV internalization by DCs pre-treated with Cytochalasin D. OMVs were labeled with FITC (Fluorescein isothiocyanate) and incubated with cultured DCs for various times (as indicated). Cells were stained with anti-CD11c. Percentages show CD11C+OMV+ populations.
Figure 9:
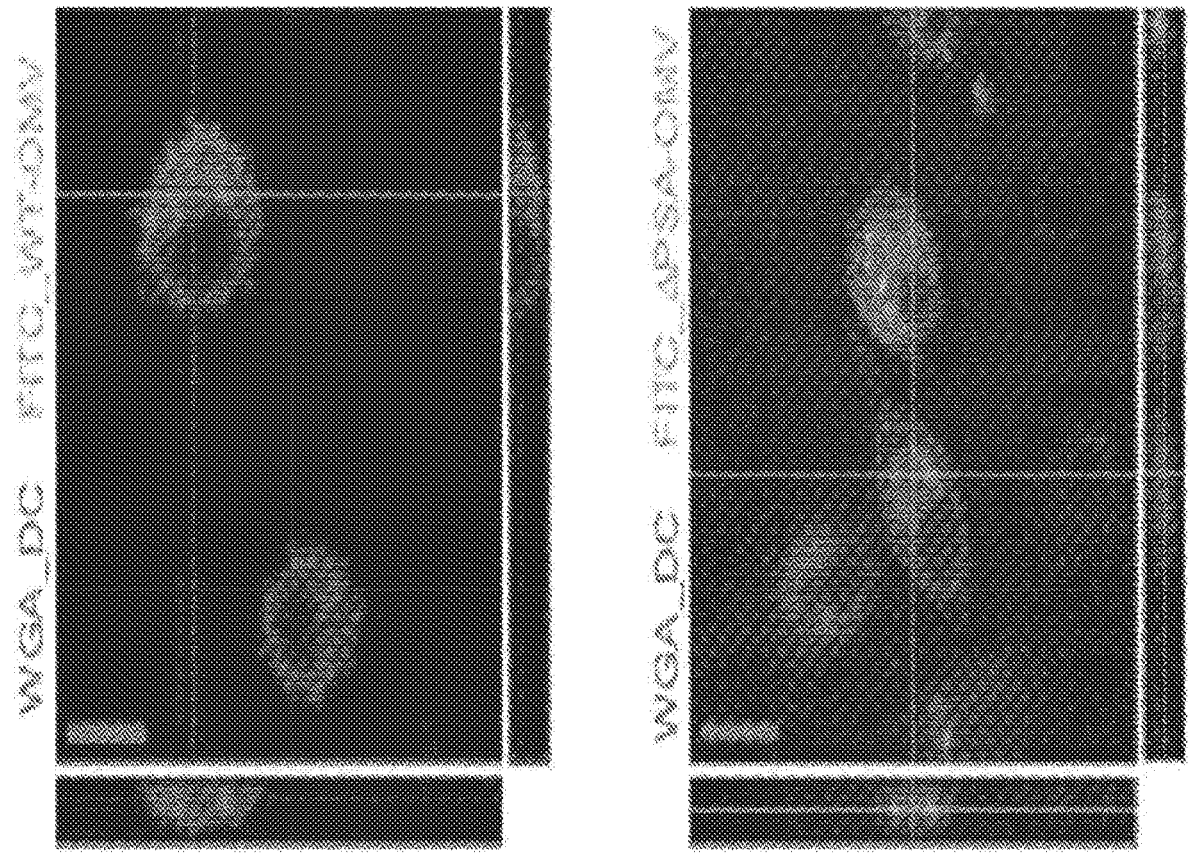
FIG. 9 shows WT-OMVs or ΔPSA-OMVs are internalized and localized in the cytoplasm of DCs. Fluorescent micrographs of OMV (WT or ΔPSA) internalization by DCs. OMVs were labeled with FITC (gray arrow) and incubated with cultured DCs for 2 hrs. Cells were fixed and cell membrane was stained with Wheat Germ Agglutinin (WGA)-tetramethylrhodamine (black arrow). Scale bar: 7.5 μm.

The results illustrated in FIG. 3a show that bone-marrow derived DCs rapidly internalized OMVs in an actin-dependent manner as treatment of cells with cytochalasin D significantly inhibited vesicle uptake (FIG. 3a and FIG. 8). Intracellular localization was confirmed by confocal microscopy (FIG. 9).

Figure 3B:
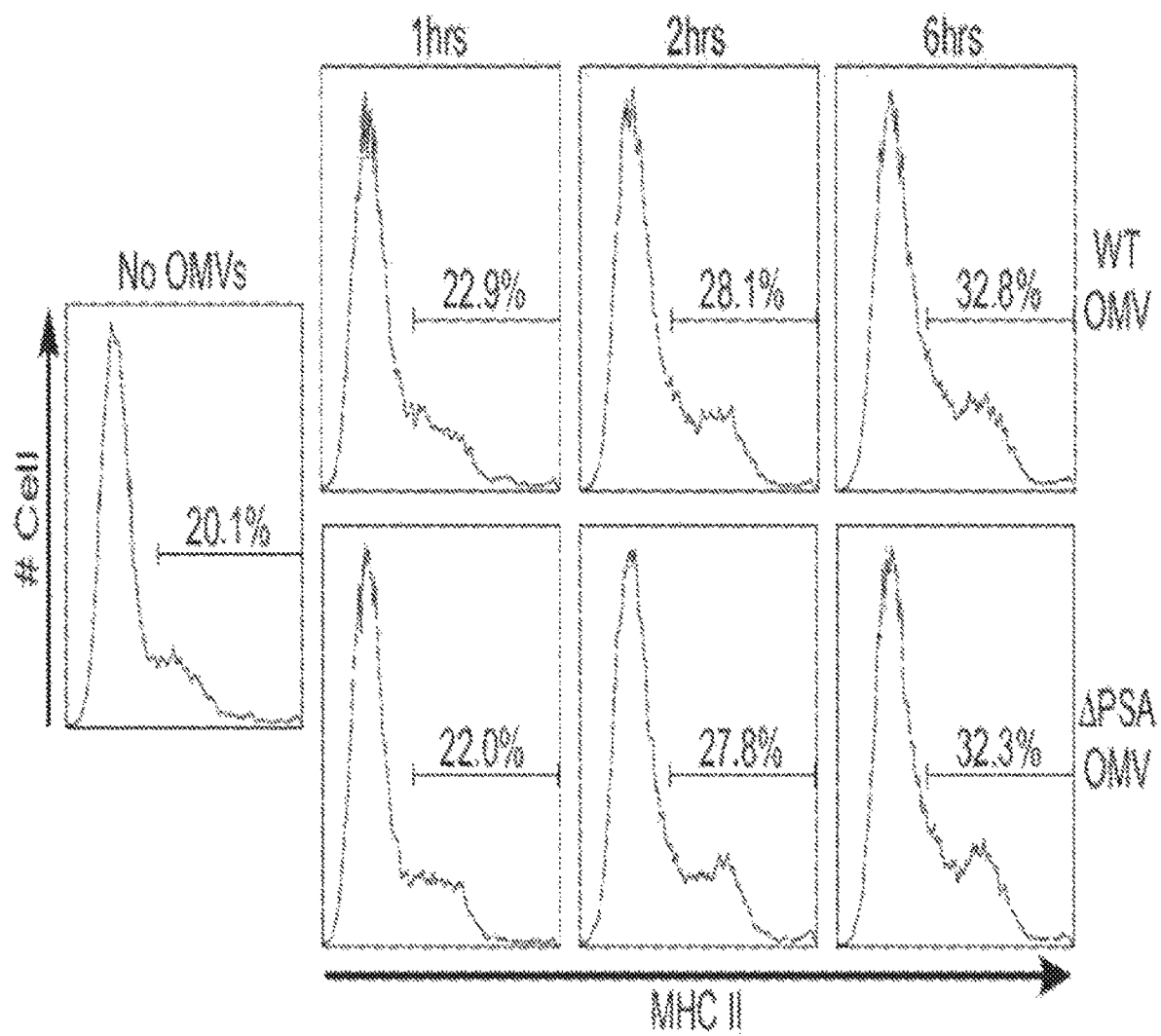
Figure 10:
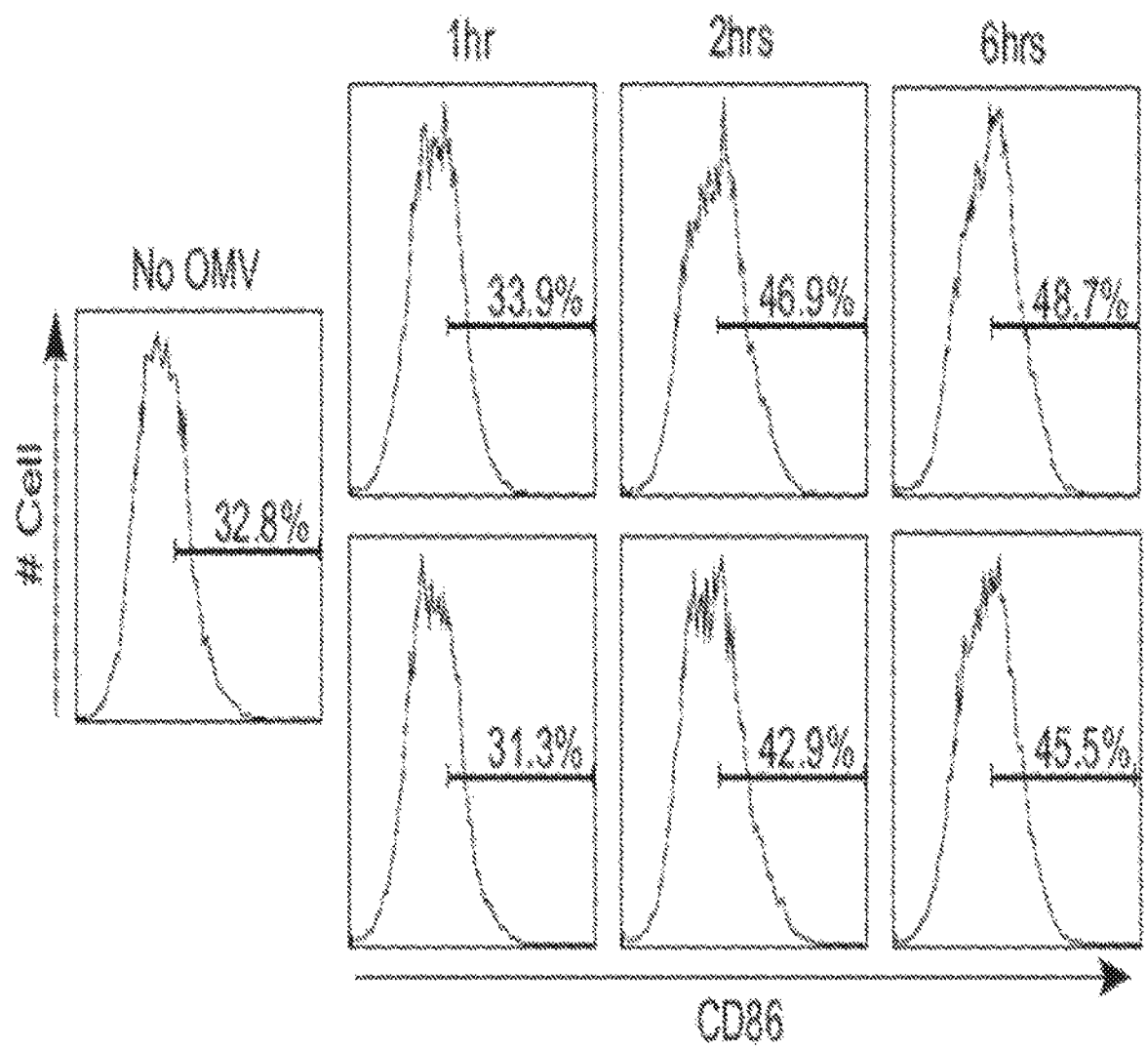
FIG. 10 shows WT-OMVs and ΔPSA-OMVs upregulate co-stimulatory molecule for DC activation. FC plots of DCs incubated with WT-OMVs and ΔPSA-OMVs for various times (as indicated) and stained with anti-CD11c and anti-CD86. Percentages show CD86+ populations among CD11c+ cells.

PSA mediated induction in the DCs of T cell activation markers was also investigated. The results illustrated in FIG. 3b indicated that expression of T cell activation markers (MHCII, CD86) was elevated equally following internalization of both WT-OMVs and ΔPSA-OMVs (FIG. 3b and FIG. 10). Increased expression of MHC and co-stimulatory molecules indicate that PSA containing OMVs from *B. fragilis* can influence T cell responses.

Example 5: PSA containing OMVs induce IL-10 expression in CD4+ T cell through DCs IL-10 expression.

In light of PSA containing OMVs protective role in colitis shown with experiments exemplified in Examples 1 to 3, the biological effects of OMVs on the induction of suppressive T cell responses were tested. In particular, as various regulatory T cell (Treg) populations are known to inhibit colitis, OMVs' ability to promote Treg development was examined.

Figure 3C:
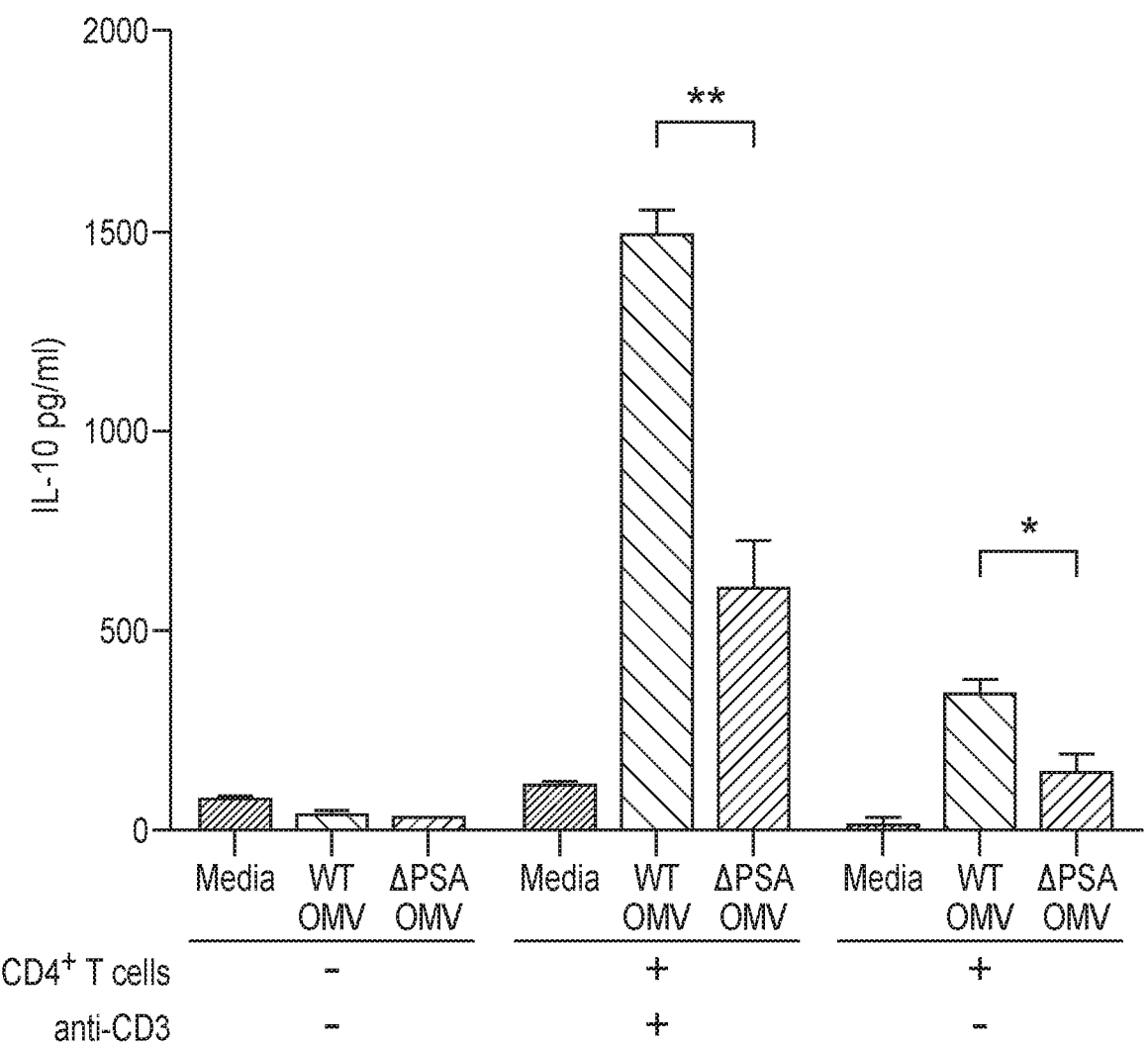

The results illustrated in FIG. 3c indicate that WT-OMVs induced the expression of IL-10 from in vitro DC-T cell co-cultures, while no IL-10 was produced from DCs alone under these conditions. Vesicles purified from *B. fragilis* ΔPSA induced significantly less IL-10 than WT-OMVs, although an increase was detected over media controls. The production of IL-10 from DCs is known to support CD4+ IL-10+ T cell development in vivo and in vitro.

Accordingly, ELISA analysis similar to the one whose results are illustrated in FIG. 3c, was performed also including DCs differentiated from IL-10–/– animals.

The results illustrated in FIG. 3d (left panel) show a greatly reduced IL-10 production in DC-T cell co-cultures when IL-10–/– DCs were treated with wild type OMVs, suggesting IL-10 expression by DCs is required to induce IL-10 from CD4+ T cell in a paracrine manner.

Example 6

PSA Containing OMVs Programs DCs to Direct Foxp3 Treg Development and/or Expansion Microbial ligands are sensed by several classes of pattern recognition receptors, and PSA has been shown to signal through toll-like receptor 2 (TLR2) to elicit Th1 cytokine production. A series of experiments were therefore performed to test whether TLR2 is required for induction of IL-10 by wild-type OMVs (containing PSA), as recent reports have shown that Treg function and IL-10 expression are influenced by TLR2.

The results illustrated in FIG. 3d (right panel) indicate that compared to wild-type DCs, the absence of TLR2 (DCs from TLR2–/– animals) completely inhibit IL-10 production in response to OMVs. Both DCs responded equally to superantigen (SEA) stimulation, demonstrating a specific defect in PSA sensing and not a general lack of T cell activation by TLR2–/– DCs (FIG. 3d). CD4+CD25+ T cells that express the transcription factor Foxp3 are an important Treg subset. Recent studies have shown that CD4+CD25+ Foxp3+ Tregs can express IL-10, and IL-10 production from Tregs is required to prevent intestinal inflammation.

To determine the source of IL-10 induced by PSA on OMVs, CD4+CD25+ and CD4+CD25-T cells were purified following co-culture with DCs and the expression of IL-10 and Foxp3 were measured by qRT-PCR.

The results illustrated in FIG. 3e indicate that remarkably, PSA-OMV significantly induced IL-10 expression in the CD4+CD25+ Treg population, but not from CD4+CD25-T cells. OMVs purified from *B. fragilis* ΔPSA were unable to promote IL-10 production from either T cell population, with levels identical to media controls. Expression of Foxp3 was also significantly increased exclusively in CD4+CD25+ T cells by OMVs in a PSA-dependent manner (FIG. 3e).

Co-cultures were set up as for experiments illustrated in FIGS. 3c-e, but using CD4+ T cells from Foxp3-GFP mice. Following 4 days of culture with OMV pulsed DCs, cells were stained with anti-CD4 and Foxp3 detected by GFP expression using FC.

Figure 3F:
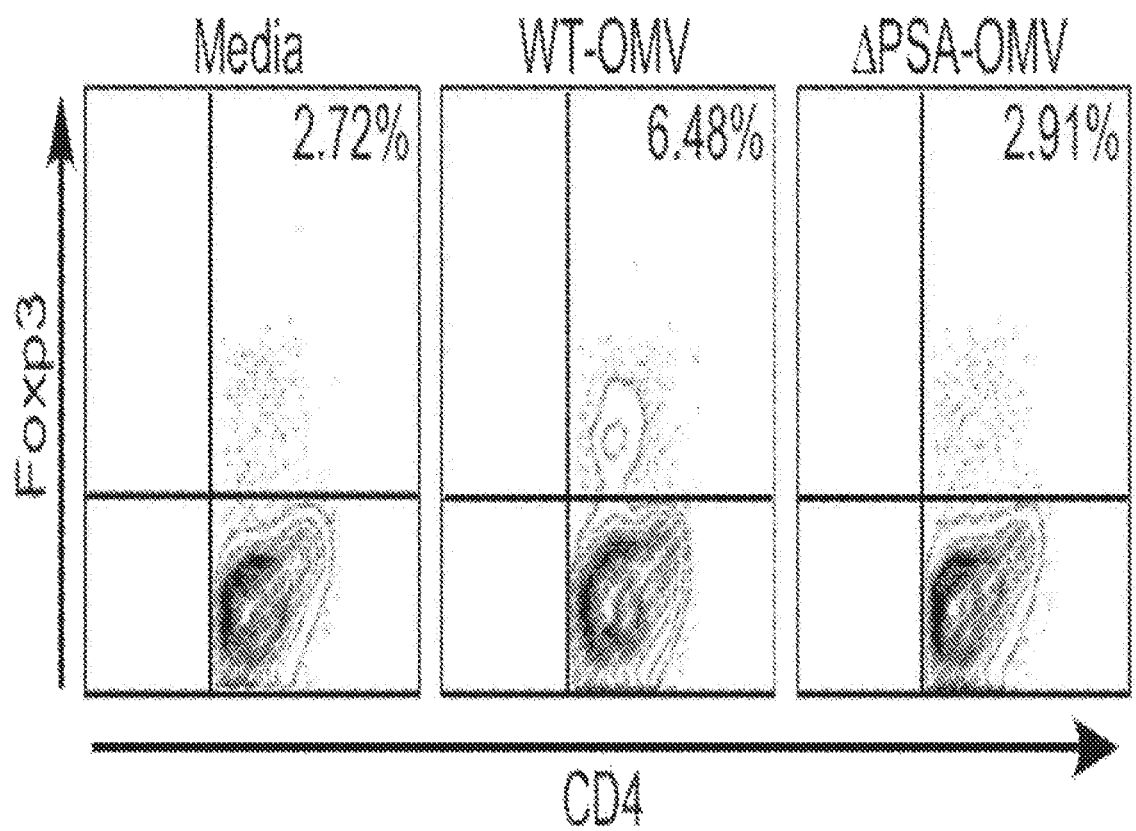

The results representative of 2 independent trials are illustrate in FIG. 3f Consistent with the increased transcription of Foxp3 among CD4+ T cells, proportions of CD4+ Foxp3+ T cells increased in response to WT-OMV but not PSA-OMV treatment (FIG. 3O. Collectively, OMVs containing PSA program DCs to direct Treg development and/or expansion in an entirely in vitro culture system.

Example 7

PSA-Containing OMVs Induce IL10 Mediated Foxp3 Treg Suppressive Function

The use of Tregs as cellular therapies has been proposed for IBD, autoimmunity and allergies. IL-10 expression by CD4+ T cell subsets following 4 day co-culture with DCs treated with OMVs was investigated. Splenic CD4+ T cell were purified from IL-10-GFP mice, stained with anti-CD4 and anti-CD25 following co-culture, and IL-10 expression measured by GFP expression.

Figure 4A:
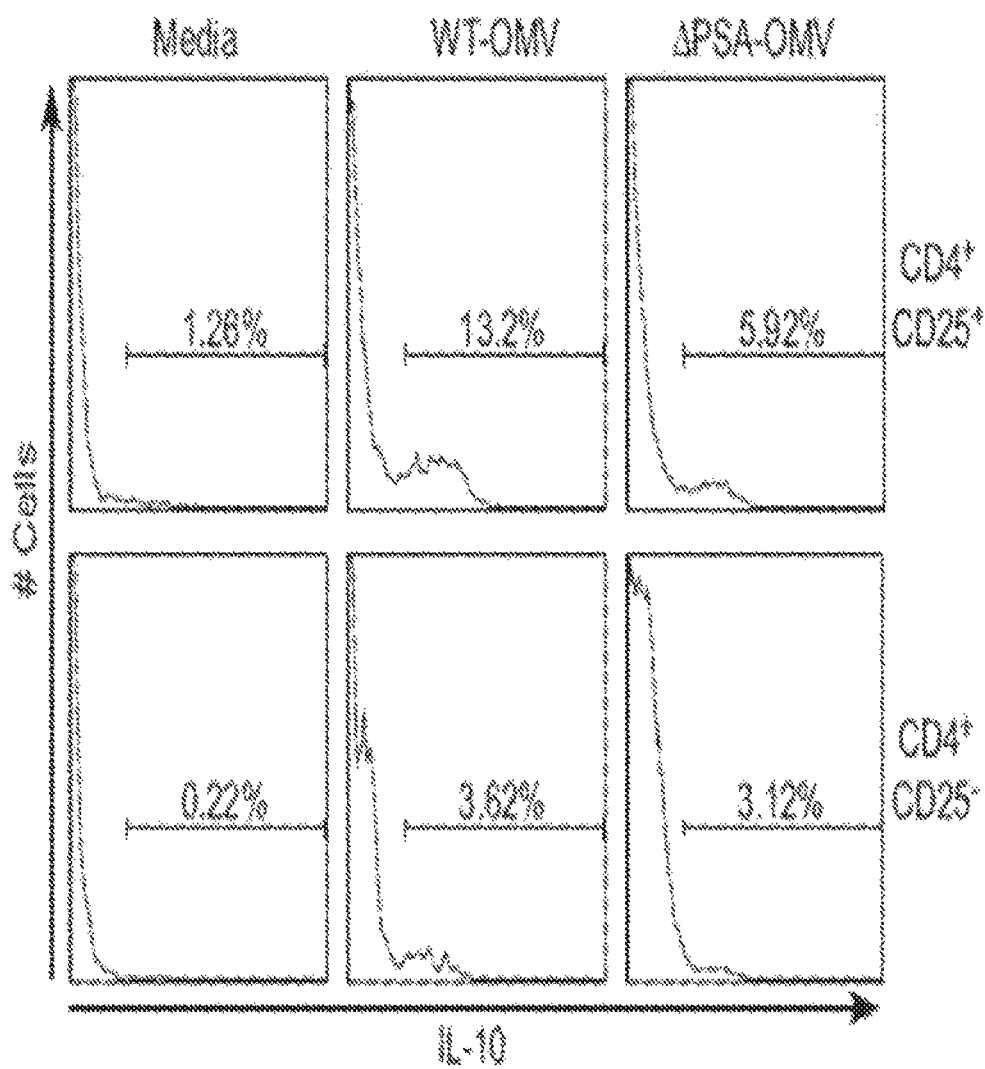
FIG. 4A-4C shows exemplary results indicating in vitro generation of Treg suppressive function by PSA-containing OMVs.

The results of the relevant OMV treatment of purified DCs & T cells illustrate in FIG. 4a indicate that revealed that PSA promotes the specific production of IL-10 from CD4+ CD25+ Tregs.

Based on this finding, the ability of PSA was investigated to promote the suppressive capacity of Tregs ex vivo. in vitro suppression of naïve responder cells by purified CD4+ CD25+ T cells following co-culture with DCs treated with media (control), WT-OMVs and ΔPSA-OMVs. CD4+ CD25-responder cells (effector cells; Teff) were purified from spleens of wild-type mice, pulsed with intracellular dye CFSE (Carboxyfluorescein succinimidyl ester), incubated with Tregs and stimulated with anti-CD3 for 3 days. Cell proliferation was measured by FC of CFSE dilution.

Figure 4B:
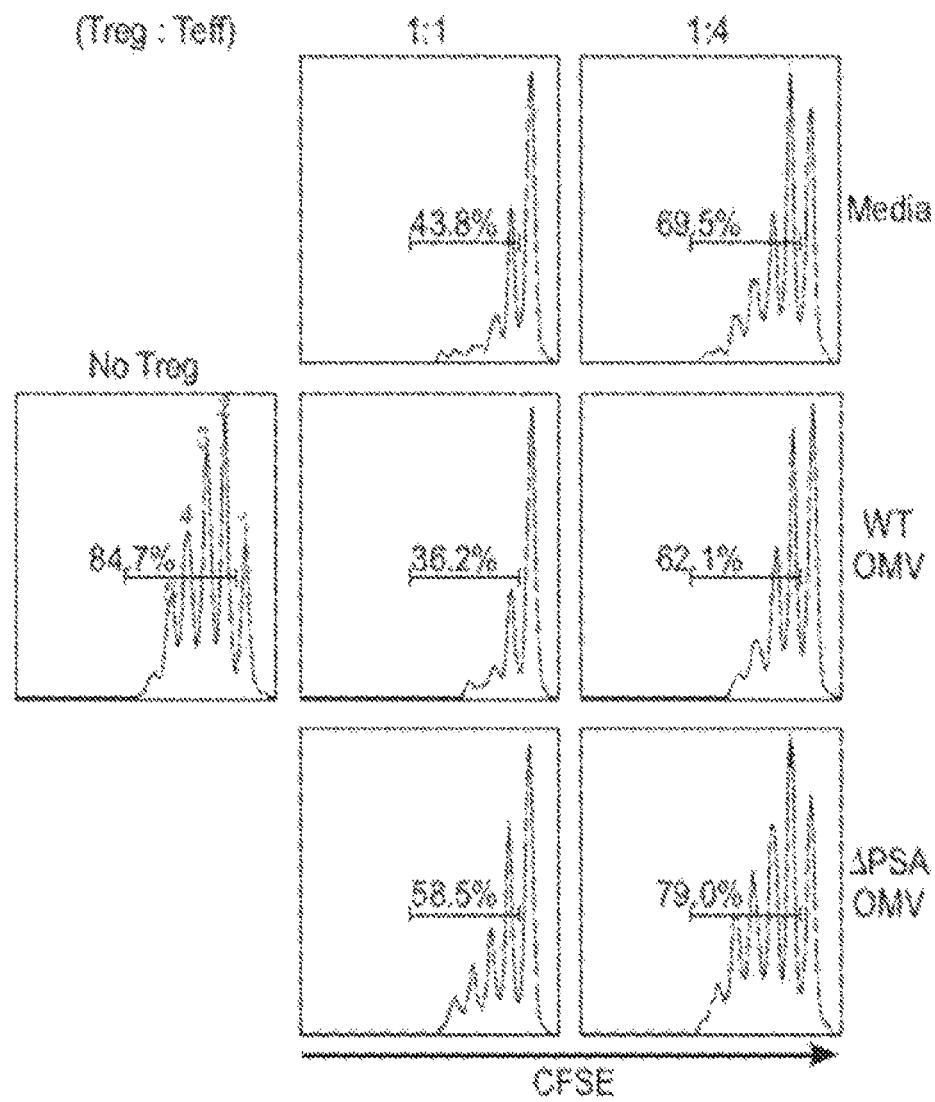
Figure 4C:
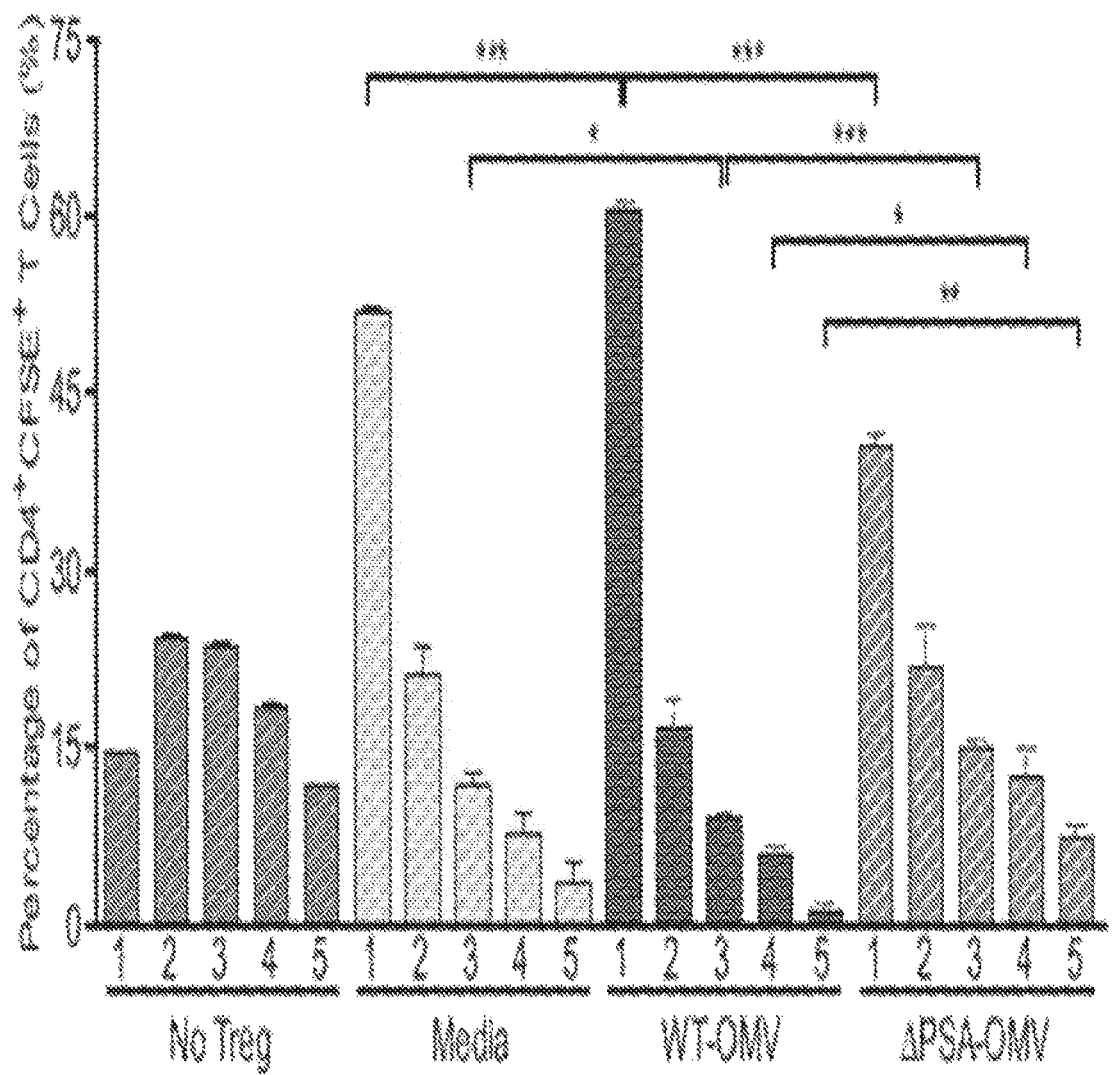

The results illustrated in FIGS. 4b and 4c indicate Tregs recovered from conditions with WT-OMV-treated DCs displayed significantly enhanced suppressive capacity compared to CD4+CD25+ T cells in response to ΔPSA-OMVs.

Therefore, the specific absence of PSA from OMVs that otherwise contain numerous microbial ligands (LPS, lipoproteins, peptidoglycan, etc.) abrogates the ability of *B. fragilis* vesicles to induce functional Tregs.

Example 8

PSA Induce Various Biomarkers Combination in Foxp3 Treg

Foxp3-GFP mice were orally treated with purified PSA every other day for 6 days. MLNs were extracted and CD4+Foxp3+ or the CD4+Foxp3-T cells were purified by FACS based on ±GFP expression (purity >99%). RNA was extracted and used for q-PCR.

Figure 11:
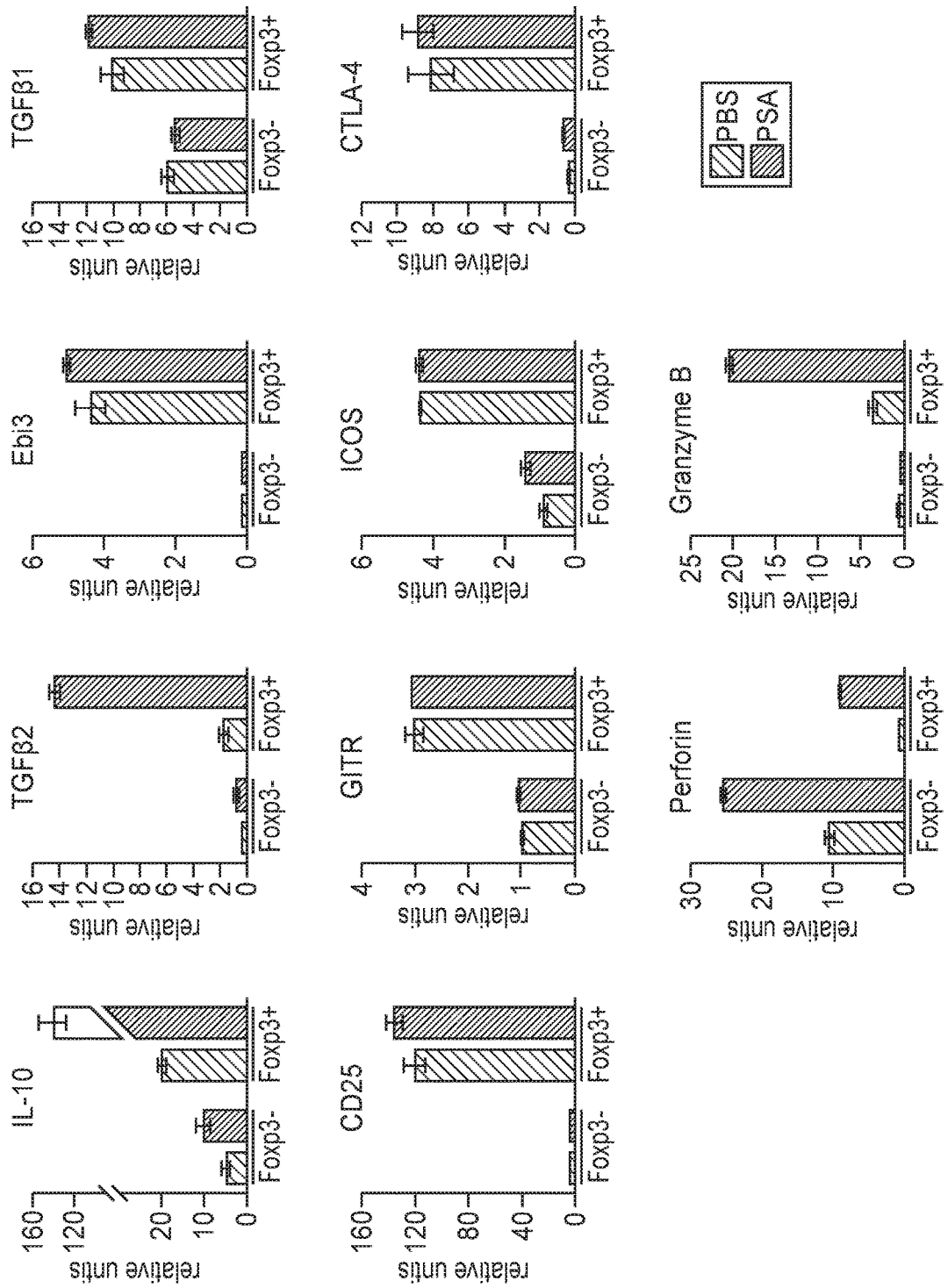
FIG. 11 shows PSA induced expression of biomarkers in an embodiment herein described. The data illustrated in each diagram are representative of three independent experiments. Light bars indicated cells derived from PBS treated mice and dark bars from PSA-treated mice.

The results illustrated in FIG. 11 demonstrate that PSA coordinates induction of multiple anti-inflammatory genes including IL-10, TGF-β, perforin, and granzyme A and the inhibition of TNFα and IL17 (in particular IL17A).

The above results provide a molecular mechanism for the probiotic activity of *B. fragilis*, and reveal a seminal example for a microbial ligand that links innate immune receptor signaling to regulatory T cell development. In particular the above results indicate that PSA is delivered to the host by outer membrane vesicles (OMVs), secretion structures that target bacterial molecules to host cells. OMVs containing PSA are internalized by dendritic cells of the host immune system. Following uptake of OMVs, PSA programs dendritic cells to induce the differentiation of regulatory T cells (Treg) that express Foxp3 and the anti-inflammatory cytokine interleukin-10 (IL-10). Treg development by OMVs requires toll-like receptor 2 (TLR2) expression and IL-10 production by dendritic cells. Remarkably, purified OMVs direct the in vitro differentiation of functional Tregs with potent suppressive activity in a PSA dependent manner. Treatment of animals with OMVs containing PSA prevents experimental colitis and suppresses pro-inflammatory cytokine responses in the gut. These findings reveal that commensal bacteria provide beneficial microbial factors through vesicle secretion, a process that can be engineered into a novel approach for delivery of probiotic therapies for IBD.

In particular, the above results show that Tregs induced by OMVs containing PSA are functionally suppressive and inhibit T cell activation in culture. This is the first demonstration of in vitro Treg development by a microbial ligand, and provides proof-of-principle to the widely-speculated notion that innate immune receptor signaling modulates Treg function. As current therapies for IBD are either ineffective or have severe side effects, probiotics represent promising new treatment options by harnessing well-evolved evolutionary mechanisms for immunmodulation. Given that Tregs suppress immune responses in multiple tissues, our seminal demonstration of in vitro Treg development by PSA suggests the exciting possibility of novel cellular therapies for numerous inflammatory disorders including autoimmunity, asthma and allergies.

To identify molecules made by microorganisms that mediate immunomodulation, fractions of bacterial products can be purified and the same assays performed as above until a pure compound is found which mimics that outcome when whole bacteria are used. Also, the approaches above could be used to screen a mutant library of a microorganism of interest to identify immunomodulatory molecules that have been deleted in a respective clone of a strain which possesses this activity.

Our previous studies have shown that PSA alone can both treat and prevent colitis in mice (Round et al. 2010). Accordingly, given our present results that show wildtype OMV, containing PSA, can prevent colitis in mice, and that this effect with the OMV seems to be PSA dependent we now propose that wildtype OMV will be effective in treating colitis in the same TNBS mice model, and have a beneficial or improved affect on humans with IBD.

It should be noted at the present time that although predictive markers for the onset of inflammatory diseases (such as IBD) are not known, once identified these predictive markers will mean that subjects/humans at risk of developing the disease can be similarly treated with the substances/compositions/OMVs as disclosed herein, to prevent the onset of the disease.

In another embodiment, OMVs (containing PSA) could be altered so that they either do not express or have reduced expression of certain enzymes (for instance. haemagglutinating and enzymic activities (hydrolyzing enzymes such as alkaline and acid phosphatases, esterase lipase. Phosphohydrolyase, glucosaminidase etc.) using molecular or physical methods known to those of skill in the art. Such modified OMVs could then be used to treat or prevent inflammation or inflammatory diseases.

The examples set forth above are provided to give those of ordinary skill in the art a complete disclosure and description of how to make and use the embodiments of the vesicles, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications can be made without departing from the spirit and scope of the present disclosure. Accordingly, other embodiments are within the scope of the following claims.

REFERENCES

1. Xavier, R. J. & Podolsky, D. K. Unravelling the pathogenesis of inflammatory bowel disease. Nature 448, 427-434 (2007).
2. Mazmanian, S. K., Round, J. L. & Kasper, D. L. A microbial symbiosis factor prevents intestinal inflammatory disease. Nature 453, 620-625 (2008).
3. Braun, J. & Wei, B. Body traffic: ecology, genetics, and immunity in inflammatory bowel disease. Annu Rev Pathol 2, 401-429 (2007).
4. Round, J. L. & Mazmanian, S. K. The gut microbiota shapes intestinal immune responses during health and disease. Nat Rev Immunol (2009).
5. Scheiffele and Fuss. (2001) Induction of TNBS colitis in mice. Current Protocols in Immunology. 15.19.1-15.19.14.
6. Mazmanian, Liu, Tzianabos, and Kasper (2005) An Immunomodulatory Molecule of Symbiotic Bacteria Directs Maturation of the Host Immune System. Cell 122:1 107-118
7. M. J. Coyne, A. O. Tzianabos, B. C. Mallory, V. J. Carey, D. L. Kasper and L. E. Comstock, (2001) Polysaccharide biosynthesis locus required for virulence of *Bacteroides fragilis*, Infect. Immun. 69: 4342-4350.
8. Patrick S, Reid J H. (1983) Separation of capsulate and non-capsulate *Bacteriodes fragilis* on a discontinuous density gradient. J Med Microbiol. 16(2): 239-41
9. Amanda L. Horstman and Meta J. Kuehn. (2000) Enterotoxigenic *Escherichia coli* secretes active heat-labile enterotoxin via outer membrane vesicles. J Biol Chem. 275: 12489-12496.
10. Nicole C. Kesty and Meta J. Keuhn. (2004) Incorporation of heterologous outer membrane and periplasmic proteins into *Escherichia coli* outer membrane vesicles. J Biol Chem. 279: 2069-2076.
11. Patrick S, McKenna J P, O'Hagan S, Dermott E. (1996) A comparison of the haemagglutinating and enzymic activities of *Bacteroides fragilis* whole cells and outer membrane vesicles. Microb Pathog. 20(4):191-202.
12. Round et al. (2010) Inducible Foxp3+ regulatory T cell development by a commensal bacterium of the intestinal microbiota. PNAS, 107 (27). 12204-12209.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

The invention claimed is:

1. A method of treating an inflammatory disease or inflammation in an individual, comprising
   administering to an individual in need thereof an effective amount of a pharmaceutical composition comprising an outer membrane vesicle derived from *B. fragilis* comprising a Polysaccharide A (PSA) and a pharmaceutically acceptable carrier to deliver the PSA to a digestive tract of the individual,
   wherein the PSA is L-PSA,
   wherein the composition is in the form of a tablet, granule, powder, solution, emulsion or suspension.

2. The method of claim 1, wherein the individual in need thereof is an individual suffering from an inflammatory disease or inflammation.

3. The method of claim 1, wherein the inflammatory disease is inflammatory bowel disease (IBD).

4. The method of claim 3, wherein treating IBD comprises reducing severity of one or more clinical IBD symptoms, reducing duration of one or more clinical IBD symptoms or reducing risk of developing a malignancy.

5. The method of claim 4, wherein the malignancy comprises colon cancer.

6. The method of claim 1, wherein the inflammatory disease is Crohn's disease.

7. The method of claim 1, wherein the PSA is delivered to a mucous membrane of the digestive tract of the individual.

8. The method of claim 7, wherein the mucous membrane of the digestive tract is intestinal mucosa, gastric mucosa, esophageal mucosa, buccal mucosa, oral mucosa, buccal mucosa, or a combination thereof.

9. The method of claim 1, wherein the outer membrane vesicle comprises a lipid membrane enclosing an aqueous environment.

10. The method of claim 1, wherein the outer membrane vesicle is heterologous to the PSA.

11. The method of claim 1, wherein the pharmaceutical composition is orally administered to the individual in need thereof.

12. The method of claim 1, wherein the outer membrane vesicle isolated from *B. fragilis* does not comprise high molecular weight PSA (H-PSA).

\* \* \* \* \*

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
acggcatgga tctcaaagac                                              20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
gtgggtgagg agcacgtagt                                              20

<210> SEQ ID NO 3
<211> LENGTH: 20
<212> TYPE: DNA
<213> ORGANISM: Artificial Sequence
<220> FEATURE:
<223> OTHER INFORMATION: PCR primer
```

<400> SEQUENCE: 3
ttaaggttct ctcctctgaa                                                                          20

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
tagggagcta aattatccaa                                                                          20

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
ggttgccaag ccttatcgga                                                                          20

<210> SEQ ID NO 6
<211> LENGTH: 19
<212> TYPE: DNA
<213> ORGANISM: Artificial Sequence
<220> FEATURE:
<223> OTHER INFORMATION: PCR primer

<400> SEQUENCE: 6
acctgctcca ctgcttgct                                                                           19

<210> SEQ ID NO 7
<211> LENGTH: 24
<212> TYPE: DNA
<213> ORGANISM: Artificial Sequence
<220> FEATURE:
<223> OTHER INFORMATION: PCR primer

<400> SEQUENCE: 7
gcaatagttc cttcccagag ttct                                                                     24

<210> SEQ ID NO 8
<211> LENGTH: 19
<212> TYPE: DNA
<213> ORGANISM: Artificial Sequence
<220> FEATURE:
<223> OTHER INFORMATION: PCR primer

<400> SEQUENCE: 8
ggatggccca tcggataag                                                                           19

<210> SEQ ID NO 9
<211> LENGTH: 17
<212> TYPE: DNA
<213> ORGANISM: Artificial Sequence
<220> FEATURE:
<223> OTHER INFORMATION: PCR primer

<400> SEQUENCE: 9
ttcgttgccg gtccaca                                                                             17

```
<210> SEQ ID NO 10
<211> LENGTH: 18
<212> TYPE: DNA
<213> ORGANISM: Artificial Sequence
<220> FEATURE:
<223> OTHER INFORMATION: PCR primer

<400> SEQUENCE: 10
accagcgcag cgatatcg                                                18
```